(12) United States Patent
Pages et al.

(10) Patent No.: US 7,414,172 B2
(45) Date of Patent: Aug. 19, 2008

(54) METHOD FOR IMPROVING PLANT TOLERANCE TO ENVIRONMENTAL STRESS

(75) Inventors: Montserrat Pages, Barcelona (ES); Dimosthenis Kizis, Barcelona (ES); Ana Isabel Sanz Molinero, Gentbrugge (BE)

(73) Assignee: Consejo Superior de Investigaciones Cientificas (CSIC), Madrid (ES)

( * ) Notice: Subject to any disclaimer, the term of this patent is extended or adjusted under 35 U.S.C. 154(b) by 550 days.

(21) Appl. No.: 10/472,957

(22) PCT Filed: Mar. 28, 2002

(86) PCT No.: PCT/EP02/03538

§ 371 (c)(1),
(2), (4) Date: Mar. 3, 2004

(87) PCT Pub. No.: WO02/079245

PCT Pub. Date: Oct. 10, 2002

(65) Prior Publication Data

US 2004/0143098 A1    Jul. 22, 2004

Related U.S. Application Data

(60) Provisional application No. 60/301,912, filed on Jun. 29, 2001.

(30) Foreign Application Priority Data

Mar. 28, 2001  (EP)  ................................. 018700690

(51) Int. Cl.
*A01H 5/00*     (2006.01)
*C12N 15/82*    (2006.01)
*C12N 5/14*     (2006.01)
*C12N 15/63*    (2006.01)
*C07H 21/00*    (2006.01)

(52) U.S. Cl. .................... 800/295; 435/468; 435/320.1; 536/23.1; 536/23.6; 800/278; 800/300.1

(58) Field of Classification Search ................. 800/295, 800/278; 435/468, 320.1; 536/23.1, 23.6
See application file for complete search history.

(56) References Cited

U.S. PATENT DOCUMENTS 5,891,859 A * 4/1999 Thomashow et al. ........... 514/44
5,981,729 A * 11/1999 Chun et al. ................. 536/23.6

FOREIGN PATENT DOCUMENTS

| WO | 99 38977 | 8/1999 |
| WO | 99 41974 | 8/1999 |
| WO | 99 55840 | 11/1999 |
| WO | 00 53724 | 9/2000 |

OTHER PUBLICATIONS

Stockinger et al. (PNAS, 94: 1035-1040, 1997).*
Keskin et al. (Protein Science, 13:1043-1055, 2004).*
Thornton et al. (Nature structural Biology, structural genomics supplement, Nov. 2000).*
Moose et al. (NCBI, GenBank, Sequence Accession No. ZMU41466, Published Dec. 15, 1996).*
Liu et al. (The Plant Cell, 10:1391-1406, Aug. 1998).*
Ngo et al. (The Protein Folding Problem and Tertiary Structure Prediction, K. Merz., and S. Le Grand (eds.) pp. 492-495, 1994).*
Wells, (Biochemistry 29:8509-8517, 1990).*
EJ Stockinger et al.: "*Arabidopsis thaliana* CBF1 encodes an AP2 domain-containing transcriptional activator that binds to the C-repeat/DRE, a cis-acting DNA regulatory element that stimulates transcription in response to low temperature water deficit" Proceedings of the National Academy of Sciences of USA, vol. 94, No. 3, pp. 1035-1040, Feb. 4, 1997.
Qiang Liu et al.: "Two transcription factors, BREB1 and DREB2, with an EREBP/AP2 DNA binding domain separtes two cellular signal transduction pathways in drought-and low-temperature responsive gene expression, respectively, in *Arabidopsis*" Plant Cell, vol. 10, No. 8, pp. 1391-1406, Aug. 1998.
J. Okamuro et al.: "The AP2 domain of APETALA2 defines a large new family of DNA binding proteins in *Arabidipsis*" Proceedings of the National Academy of Sciences of USA, vol. 94, No. 13, pp. 7076-7081 Jun. 1997.
RR Finkelstein et al.: "The *Arabidopsis* abscisic acid response locus AB14 encodes an APETALA2 domain protein" Plant Cell, vol. 10, pp. 1043-1054, Jun. 1998.
Database EMBL 'Online!, Feb. 15, 2000 V. Walbot: "Maize ESTs from various cDNA libraries sequenced at the Stanford University", Database accession No. AW438153, XP002185940.
Database EMBL 'Online!, Jan. 11, 2001 V. Walbot: "Maize ESTs from various cDNA libraries sequenced at the Stanford University" Database accession No. BF728697, XP002185941.
Database EMBL 'Online!, Mar. 31, 1999 T Sasaki: "Rice cDNA from mature leaf" Database accession No. AU057740, XP002215825.
Database EMBL 'Online!, Dec. 1, 2001 Database accession No. 0949D4, XP002215826.
D. Kizis et al.: "Role of AP2/EREBP transcription factors in gene regulation during abiotic stress" FEBS Letters, vol. 498, No. 2-3, pp. 187-189, Jun. 8, 2001.
J Medina et al.: "The *Arabidopsis* CBF gene family is composed of three genes encoding AP2 domain-containing proteins whose expression is regulated by low temperature but not by abscisic acid or dehydration" Plant Physiology, vol. 119, No. 2, pp. 463-469, Feb. 1999.

(Continued)

*Primary Examiner*—Phuong T. Bui
*Assistant Examiner*—Vinod Kumar
(74) *Attorney, Agent, or Firm*—Oblon, Spivak, McClelland, Maier & Neustadt, P.C.

(57) ABSTRACT

Provided are DNA sequences encoding a novel type of AP2 domain-containing transcription factor as well as methods for obtaining similar sequences. Also described are methods for obtaining plants with improved growth and enhanced stress tolerance, particularly tolerance to osmotic and dehydration stress, such methods comprising expression of such DNA sequences in a plant or parts thereof. Further described are diagnostic compositions comprising the aforementioned DNA sequences and the use of such sequences in plant breeding and/or agriculture.

31 Claims, 12 Drawing Sheets

OTHER PUBLICATIONS

Peter K. Busk et al.: "Regulation of abscisic acid-induced transcription" Plant Molecular Biology, vol. 37, No. 3, pp. 425-435, Jun. 1998.

PK Busk et al.: "Regulation of abscisic acid and water stress response genes" Genetic and Environmental Manipulation of Horticultural Crop, pp. 143-156, 1998, XP001037254.

Peter Kamp Busk et al.: "Regulatory elements in vivo in the promotor of the abscisic acid response gene rab17 from maize" Plant Journal, vol. 11, No. 6, pp. 1285-1295 1997, XP002137913.

* cited by examiner

|  | 104 |  |  |  |  |  |  |  |  |  |  |  |  |  |  | 119 |
|---|---|---|---|---|---|---|---|---|---|---|---|---|---|---|---|---|
| DBF1 (SEQ. I.D. NO. 17) | R | A | P | L | D | P | A | V | D | A | K | L | Q | A | I | C |
| AAF76898 (SEQ. I.D. NO. 18) | Y | K | P | L | H | S | S | V | N | A | K | L | E | A | I | C |
| AAF87854 (SEQ. I.D. NO. 19) | Y | Q | P | L | Q | S | S | V | D | A | K | L | E | A | I | C |
| T05015 (SEQ. I.D. NO. 20) | F | N | P | L | H | S | S | V | D | A | K | L | Q | E | I | C |

CONSENSUS

P L        V D A K L Q  I C
                                  N     E

| (SEQ. I.D. NO. 21) PZ02_LUPPO | Q | S | S | S | S | K | L | L | S | A | T | L | I | A | K | L |
| DREB1A (SEQ. I.D. NO. 22) | R | L | R | I | P | E | S | T | C | A | K | D | I | Q | K | A |
| CBF1 (SEQ. I.D. NO. 23) | R | L | R | I | P | E | S | T | C | A | K | D | I | Q | K | A |

FIGURE 1B

```
                                    (SEQ.I.D. NO.3) DBF1      (1) ----------------------------------------------------
Translation of AJ307662-cac39058               (1) MLLNPASREVAALDSIRHHLLEEEETPATAPAPTRRPVYCRSSSFGSLV
                                 Consensus     (1)

DBF1      (1) --------------------------------------------------
Translation of AJ307662-cac39058              (51) ADQWSESLPFRPNDAEDMVYGALRDAFSSGWLPDGSFAAVKPESQDSYD
                                 Consensus    (51)

DBF1      (1) MQFIQAQIHLQRNPGLGPRAQPMKPAVPVPPAPAP----Q--RPVKLYP
Translation of AJ307662-cac39058             (101) GSSIGSFLASSSSEAGTPGEVTSTEATVTPGIREGEGEAVAVASRGKHYP
                                 Consensus   (101)              I A L         A   P              A   P      K YR DBF1     (44) GVRQRHWGKWVAETRLR-RNRIRLWLGTFDTAEQAALAYDQAAYRLRGDA
Translation of AJ307662-cac39058             (151) GVRQRPWGKFAAEIRDPAKNGARVWLGTFDSAEEAAVAYDRAAYRMRGSR
                                 Consensus   (151) GVRQR WGKF AEIR P KN  RLWLGTFDSAE  AALAYD AAYRLRG DBF1     (93) ARLNFRDNAESRAPLDPAVDAKLQAICATIAAASSSSKNSKAKSKAMPIN
Translation of AJ307662-cac39058             (201) ALLNFPLRIGS--------ELAAAAAAAGNK-----RPYPDP
                                 Consensus   (201) A LNFP       S                   I A   AAAAA   K   K   P DBF1    (143) ASVLEAAAASPSNSSSDEGSGSGFGSDDEMSSSSPTPVVAPPVADMGQLD
Translation of AJ307662-cac39058             (232) ASSGSSSPSSSSSSSSSSS-------PKRKRGEAAPASMAMALVP
                                 Consensus   (251) AS   AA AS  S  SSS    SGS                    AP        MA  L DBF1    (193) FSEVPWDEDESFVLRKYPSYFIDWDALLSN-
Translation of AJ307662-cac39058             (274) PPPPPAQAPVQLAIPAQPWFAAGPIQQLVS- (SEQ.I.D. NO. 16)
                                 Consensus   (301)            P       L    P F     L
```

FIGURE 7 B

SEQ ID NO 1
Contains three tandem repeats of the DRE2 element (underlined) used as bait in the one hybrid screen (Example 1; Busk et al. 1997)

AATTCCCGGGCC<u>ACCGAC</u>GCACGGCCGC<u>ACCGAC</u>GCACGGCCGGGCC<u>ACCGAC</u>
GCACGG

SEQ ID NO 2
DBF1 nucleotide sequence
1043 nucleotides
DNA sequence
*Zea mays*

GCACGAGCAATCCCCTTCAACAAACGCACCGCACTCCACGGCAGCCAGAAAAC
ACATCCCACGGGGCCCAGACCCGGCGACCCACCTGAGCCCGGCGCAGATGCAG
TTCATCCAGGCCCAGCTCCACCTGCAGCGGAACCCGGGGCTGGGCCCGCGGGC
GCAGCCCATGAAGCCCGCCGTCCCAGTGCCGCCGGCGCCGGCGCCGCAGCGGC
CTGTGAAGCTGTACCGCGGCGTGCGGCAGCGTCACTGGGGCAAGTGGGTGGCC
GAGATCCGGCTCCCCGGAACCGCACCCGCCTGTGGCTCGGGACCTTCGACAC
CGCCGAGCAGGCAGCGCTGGCCTACGACCAGGCGGCGTACCGCCTCCGCGGGG
ACGCGGCGCGGCTCAACTTCCCCGACAACGCGGAGTCCAGGGCGCCGCTCGAC
CCCGCCGTGGACGCCAAGCTGCAGGCCATCTGCGCCACCATCGCCGCCGCGTC
GTCGTCATCCAAGAATTCCAAGGCCAAGAGCAAGGCGATGCCAATCAACGCGT
CCGTTCTGGAAGCGGCAGCGGCGTCTCCGAGCAACAGCTCCTCCGACGAAGGT
TCCGGCTCCGGGTTCGGGTCGGACGACGAGATGTCCTCGTCTTCCCCGACGCC
GGTGGTGGCGCCGCCGGTGGCGGACATGGGACAGTTGGATTTCAGCGAGGTTC
CGTGGGACGAGGACGAGAGCTTCGTGCTCCGCAAGTACCGTCCTACGAGATC
GACTGGGACGCGCTGCTCTCCAACTAGTCGCCCTTCGCCGACAGATGTGCTGT
TGTAGTTCAGTAGTGGCAGTATCTCTGGCCGCCGCAGATGAGGTTTTAGGCAA
TCTGCAGGCCGCCGGCCCATGTGTATTAAGTAGGTTTTGCTCAGTTGTTGGCC
CCGGACTTCGCCGGCGTTTTTGTGACCGGCGTCCCCGAGTGCACTGCATTGGT
GTACTGGTCTGTCTGTAAAAAAAAATGGATCTGTGTACTTCTATAGTGTGTAT
TCAACCATTGTTCTTAAAAAAAAAAAAAAAAAAAAA

FIGURE 8

SEQ ID NO 3
DBF1 amino acid sequence
222 AMINO ACIDS
PROTEIN SEQUENCE
Zea mays MQFIQAQLHLQRNPGLGPRAQPMKPAVPVPPAPAPQRPVKLYRGVRQRHWGKW
VAEIRLPRNRTRLWLGTFDTAEQAALAYDQAAYRLRGDAARLNFPDNAESRAP
LDPAVDAKLQAICATIAAASSSSKNSKAKSKAMPINASVLEAAAASPSNSSSD
EGSGSGFGSDDEMSSSSPTPVVAPPVADMGQLDFSEVPWDEDESFVLRKYPSY
EIDWDALLSN*

SEQ ID 4: 5´-ggggTCGACCGGGCCACCGACGCACCGGCTCGAG-3´

SEQ ID 5: 5´-ggggCTCGAGCCGTGCGTCGGTGGCCCGGTCGA-3´

SEQ ID 6: 5´- ggggTCGACCGGGCCAGAATTCCACCGGCTCGAG-3

SEQ ID 7: 5´-ggggCTCGAGCCGTGGAATTCTGGCCCGGTCGA-3´

SEQ ID 8: 5´-ggggTCGAGAAGAACCGAGACGAAGCGGTCGAG-3´

SEQ ID 9: 5´-ggggCTCGACCGCTTCGTCTCGGTTCTTCTCGA-3´

SEQ ID 10: 5´-ggggTCGAGAAGAACCGACGTGGCGGTCGAG-3´

SEQ ID 11: 5´-ggggCTCGACCGCCACGTCTCGGTTCTTCTCGA-3´

SEQ ID 12: 5´-tggaagcttCGCGCCACGTGGGCATGagatct-3´

SEQ ID 13: 5´-tggagatctCATGCCCACGTGGCGCaagctt-3´

SEQ ID 14:
CONSERVED PEPTIDE SEQUENCE BETWEEN DBF1 AND RELATED
PROTEINS

PLXXXVD/NAKLQ/EXIC (X = ANY NATURAL AMINO ACID)

FIGURE 8 (contin.)

SEQ ID NO 15:
OSDBF1

ATGCTGCTTAATCCGGCGTCGAGAGAGGTGGCCGCGCTGGACAGCATCCGGCA
CCACCTCCTGGAGGAGGAGGAGGAGACGCCGGCGACGGCGCCGGCGCCGACGC
GGCGGCCGGTGTACTGCCGGAGCTCAAGCTTCGGCAGCCTCGTGGCCGACCAG
TGGAGCGAGTCGCTGCCGTTCCGGCCCAACGACGCCGAGGACATGGTCGTGTA
CGGCGCCCTCCGCGACGCCTTCTCCTCCGGCTGGCTCCCCGACGGCTCATTCG
CCGCCGTCAAGCCGGAGTCGCAGGACTCCTACGACGGGTCCTCCATCGGCAGC
TTCCTCGCGTCGTCGTCGTCCGAGGCGGGGACGCCCGGGGAGGTGACGTCGAC
GGAGGCGACGGTGACGCCGGGGATCAGGGAGGGCGAGGGCGAGGCCGTGGCGG
TGGCGTCGAGGGGGAAGCACTACCGCGGGGTGAGGCAGCGGCCGTGGGGCAAG
TTCGCGGCGGAGATCAGGGACCCGGCCAAGAACGGCGCGCGCGTGTGGCTCGG
CACGTTCGACTCCGCCGAGGAGGCCGCCGTGGCGTACGACCGCGCCGCCTACC
GCATGCGCGGCTCCCGCGCGCTCCTCAACTTCCCGCTCCGCATCGGCTCCGAG
ATCGCCGCCGCGGCCGCCGCCGCCGCCGCGGGCAACAAGCGGCCATATCCCGA
CCCGGCGAGCTCCGGCTCTTCTTCCCCTTCATCCTCTTCCTCCTCGTCGTCGT
CTTCCTCCTCCGGGTCACCGAAGCGGAGGAAGAGAGGCGAGGCCGCGCCCGCG
TCCATGGCCATGGCACTGGTTCCACCACCGCCACCACCGGCGCAGGCACCGGT
GCAGCTCGCCCTCCCGGCCCAGCCATGGTTCGCCGCCGGTCCGATCCAGCAGC
TGGTGAGCTAA

SEQ ID NO 16:
OSDBF1

MLLNPASREVAALDSIRHHLLEEEEETPATAPAPTRRPVYCRSSSFGSLVADQ
WSESLPFRPNDAEDMVVYGALRDAFSSGWLPDGSFAAVKPESQDSYDGSSIGS
FLASSSSEAGTPGEVTSTEATVTPGIREGEGEAVAVASRGKHYRGVRQRPWGK
FAAEIRDPAKNGARVWLGTFDSAEEAAVAYDRAAYRMRGSRALLNFPLRIGSE
IAAAAAAAAGNKRPYPDPASSGSSSPSSSSSSSSSSSGSPKRRKRGEAAPA
SMAMALVPPPPPAQAPVQLALPAQPWFAAGPIQQLVS

FIGURE 8 (contin.)

METHOD FOR IMPROVING PLANT TOLERANCE TO ENVIRONMENTAL STRESS

CROSS REFERENCE TO RELATED APPLICATIONS

This application claims priority to International Application Number PCT/EP20/03583, filed on Mar. 28, 2002, to European Patent Office Application Number EP 01870069.0, filed Mar. 28, 2001, and to U.S. Provisional Application No. 60/301,912, filed on Jun. 29, 2001, all of which are incorporated, by reference, in their entireties.

FIELD OF THE INVENTION

The present invention relates generally to a method of improving the tolerance of plants to environmental stress, including but not limited to drought, and/or salt, and/or dehydration, and/or heat, and/or cold, and/or freezing, and/or water logging, and/or wounding, and/or mechanical stress, and/or oxidative stress, and/or ozone, and/or high light, and/or heavy metals, and/or nutrient deprivation, and/or toxic chemicals and/or pathogen (including viruses, bacteria, fungi, insects and nematodes) and/or combinations of these, said method comprising expressing an abscicic acid (ABA)-regulated, DRE-binding protein of the AP2/EREBP transcription factor family, such as maize DBF1, in the plant, operably under the control of a constitutive or regulatable promoter sequence such as a stress-inducible promoter, cell-specific promoter, tissue-specific promoter, or organ-specific promoter sequence. Preferably, the characteristics modified by the present invention relate to growth, and/or yield, and/or survival under suboptimal growing conditions. The present invention extends to genetic constructs, which are useful for performing the inventive method and to transgenic plants produced therewith having altered growth, and/or yield, and/or survival properties compared to their otherwise isogenic counterparts.

BACKGROUND TO THE INVENTION

Growth, biomass production, yield, development, morphology, and survival of plants is determined by the growing conditions. Factors affecting these agriculturally important characteristics include, among others, availability of water, minerals and nutrients, temperature, light intensities, presence of competitors or pathogens, and occurrence of soil or air pollution. In agriculture, suboptimal growing conditions can often be remedied. For example, dry soils are irrigated, poor soils are fertilized, while pesticides and herbicides are applied to control pathogen infestations and competitors, respectively. Yet, the growing concern for sustainable and environmental friendly agriculture demands for changes in farming practices. Massive irrigation of farmland, commonly used for the cultivation of cotton and other crops, are being increasingly opposed because they lead to salinization of soils and a reduction in water levels in downstream areas. Similarly, the intensified use of agrochemicals is heavily criticized, because of suspected negative effects on the well being of humans and animals. At the same time, the growing world population is forcing agriculture into the use of marginal land, thus expanding the range of environments in which crops are cultivated. As a result, the production of stress-tolerant varieties has become a worldwide priority for most important crops.

Although conventional plant-breeding programs have improved yields for crops grown in stressful environments, there is a growing belief that further gains will mostly be achieved through targeted manipulation of genes involved in stress tolerance. Many stress-inducible genes have been identified over the past years, some of which were shown to confer a certain increase in stress tolerance, when overexpressed in transgenic, plants. However, from these studies the notion emerged that tolerance to environmental stress is highly complex, requiring the coordinated activation of multiple genes. This has led to the adoption of transgenic strategies that make use of signal transduction components controlling the expression or activity of stress defense proteins, rather than of stress defense proteins themselves.

Successful examples of this kind are the overexpression of AP2 domain transcription factors CBF1 and DREB1A, and of the heat-shock factors HSF1 and 3 in *Arabidopsis*. CBF1 was shown to enhance freezing tolerance (Jaglo-Ottosen et al., Science 280:104-106, 1998; Thomashow, U.S. Pat. No. 5,929,305), while DREB1A induced tolerance to cold and drought stress (Kasuga et al., Nature Biotechnol 19:287-291, 1999) in *Arabidopsis*. HSF1 and 3 both conferred thermotolerance in transgenic plants (Lee and Schöffl, Plant J 8:603-612, 1995; Prandl et al., Mol Gen Genet 258:269-278, 1998).

SUMMARY OF THE INVENTION

The present invention embodies ah isolated DNA sequence with nucleotide sequence as given in SEQ ID NO 2, encoding transcription factor with amino acid sequence as given in SEQ ID NO 3, which is capable of binding to the DRE2 cis regulatory element of the Rab17 promoter of maize. This transcription factor belongs to a novel type of AP2 domain-containing transcription factors and is denominated further on as DBF1. DBF1 and the DRE2 element are shown in the present invention to mediate abscisic acid (ABA) responses in plants. ABA is a plant hormone involved in many plant processes, among which the induction of stress tolerance. It is the first time that a link between an ABA responsive protein or ABA responsive pathway and a DRE cis-element is established. Moreover this link is established by the identification of a DRE binding protein that surprisingly belongs to the AP2 domain containing protein class, of which formerly known members are all involved in an ABA-independent way.

The present invention includes also methods to identify proteins from maize and other plants which can bind the DRE2 regulatory element, as well as methods to identify proteins and compounds that interact with DBF1.

A first embodiment of the current invention comprises an isolated nucleic acid sequence encoding a polypeptide and/or functional fragment thereof, said polypeptide selected from the group consisting of:
  (a) polypeptide sequences comprising at least part of the protein sequence, as to given in SEQ ID NO 3,
  (b) polypeptide sequences consisting of a protein or fragment thereof that binds to a cis regulatory DNA sequence SEQ ID NO 1,
  (c) polypeptide sequences constituting an AP2/EREBP domain-containing transcription factor or fragment thereof that binds to a cis regulatory DNA sequence and for which the intensity of such binding is regulated by ABA,
  (d) polypeptide sequences constituting an AP2/EREBP domain-containing transcription factor or fragment thereof that binds to a cis regulatory DNA sequence and that activates the transcription of the sequences regulated by this cis regulatory element in response to ABA,
  (e) polypeptide sequences constituting an AP2/EREBP domain-containing transcription factor or fragment thereof which contain a peptide that is at least 50% and preferably 70% identical, or more, to SEQ ID NO 14, (f), protein sequences constituting a full-length AP2/ EREBP domain-containing transcription factor which are at least 35% or 37% identical, more preferable 40%, and most preferable 45% identical, or more, to the amino acid sequence of SEQ ID NO 3.

Embodied in the present invention are also methods for modifying growth, yield, and stress tolerance of plants, comprising the modification of expression in particular cells, tissues, or organs of a plant, of a nucleic acid sequence as defined above, expressed under control of a constitutive and/ or ubiquitous or regulated promoter. The regulated promoter may be controlled by stress-responsive or cell/tissue/organ-specific factors. The present invention relates also to a cell or plant containing said genetic construct.

The present invention furthermore encompasses methods for modifying growth, yield, and stress tolerance of plants, comprising the modification of expression of DBF1 or DBF1-like sequences as described above, in combination with the modification of expression of other signal proteins involved in ABA signaling.

DETAILED DESCRIPTION OF THE INVENTION

Dehydration stress is probably the most important abiotic stress in agriculture. A cell undergoes dehydration stress when it experiences a shortage of water. Most commonly, this situation arises as a consequence of drought. Yet, also salt and cold (in particularly freezing) stress lead to dehydration stress at the cellular level. In addition, any tissue injury (as a consequence of wounding, mechanical stress, pathogens), as well as heat, can lead to enhanced water evaporation and thus to dehydration stress. Water loss at the cellular level can also occur as the result of membrane damage, for example as a consequence of lipid peroxidation during oxidative stress.

The plant hormone abscisic acid (ABA) plays an important role in the protection of plants against dehydration stress. ABA stimulates stomatal closure, and, at the cellular level, induces the synthesis of proteins that protect cellular components against dehydration injury. The invention described herein enhances the synthesis of such protective proteins in plants. By using the methods of the present invention, such protective proteins are synthesized without inducing all the pleiotropic effects of ABA in the plant, since these methods do not involve the application of ABA itself.

Induction of defense responses by ABA has been shown to involve two signaling pathways, one involving MYC/MYB transcription factors (Urao et al., Plant Cell 5:1529-1539, 1993), and the second involving bZIP factors, that bind to ABREs (ABA-responsive elements; Guiltinan et a/, Science 250:267-271, 1990). Single ABRE elements have also been identified as cis-acting elements in promoters of genes that are not regulated by ABA. Yet, it has been demonstrated that binding of bZIP factors to ABRE repeats in response to ABA requires repeats of ABRE elements (reviewed by Busk and Pages, Plant Mol. Biol. 37:425-435,1998).

The rab17 (responsive to abscisic acid) gene is a well-known example of an ABA responsive gene in maize. The Rab17 promoter contains 5 putative ABRE elements, and it therefore classifies as a functional bZIP binding cis element, involved in ABA signaling (Busk et al, Plant J 11:1285-1295, 1997). The rab17 promoter also contains DRE elements, of which the core sequence is identical to the DRE (drought-responsive) and CRT (cold-response elements) elements in *Arabidopsis*. DRE/CRT elements are found in the promoters of genes such as rd29A, rd17, cor6.6, cor15a, erd10 and kin1, and the induction of these genes involves the DRE/CRT elements. Yet, it appears that different transcription factors are recruited to these elements, depending on the nature of the stress situation. These transcription factors belong to the AP2/ EREBP (apetala 2/ethylene response element binding protein) type and are designated DREB (DRE binding factor; Liu et al., Plant Cell 10:1391-1406, 1998) or CBF (CRT binding factor; Stockinger et al., Proc Natl Acad Sci 94:1035-1040, 1997). For example, expression of DREB1A is strongly induced by cold and weakly by drought, while DREB2A is mainly responsive to drought (Liu et al., Plant Cell 10:1391-1406, 1998). CBF (identical to DREB1B) is constitutively expressed (Stockinger et al. Proc Natl Acad Sci 94:1035-1040, 1997), while there is some controversy as to whether it is additionally induced by cold (Stockinger et al., Proc. Natl Acad Sci 94:1035-1040, 1997; Liu et al., Plant Cell 10: 1391-1406, 1998).

Interestingly, ABA does not seem to play a role in the activation of DREB/CBF1 in *Arabidopsis*, since control of DRE-mediated transcription occurs in an ABA independent mode. It was surprising therefore to find that the DRE elements in the rab17 promoter of maize take part in the activation of gene expression by ABA (Busk et al., Plant J 11:1285-1295, 1997). This finding prompted us to initiate investigations toward the elucidation of the transcription factors that bind to the DRE2 element in maize and that activate gene expression through DRE2 in response to ABA. The characterization of such a factor forms the basis of this invention.

The present invention relates to an isolated nucleic acid encoding an AP2/EREBP domain-containing transcription factor or encoding an immunologically active and/or functional fragment of such a protein selected from the group of:

(a) nucleic acid comprising at least part of the DNA sequence as given in SEQ ID NO 2, (b) nucleic acid comprising the RNA sequence corresponding to at least part of SEQ ID NO 2, (c) nucleic acid specifically hybridizing with the nucleic acid acid as defined in (a) or (b), (d) nucleic acid encoding a protein having an amino acid sequence which is at least 35%, preferably 37% or 40%, and more preferably 45% or more identical to the amino acid sequence as given is SEQ ID NO 3, (e) nucleic acid encoding a protein comprising the amino acid sequence as given in SEQ ID NO 3 or an immunologically active or functional fragment thereof, (f) nucleic acid encoding a protein comprising the amino acid sequence as given in SEQ ID NO 14 or comprising a sequence which is at least 75% identical to the sequence as represented in SEQ ID NO 14, or an immunologically active or functional fragment of said protein, (g) nucleic acid which is degenerated as a result of the genetic code to a nucleic acid sequence encoding a protein as given in SEQ ID NO 3 or to a nucleic acid as defined in (a) to (f);

(h) nucleic acid which is diverging due to the differences in codon usage between the organisms to a nucleic acid sequence encoding a protein as given in SEQ ID. NO 3 or the nucleic acid as defined in (a) to (f), (i) nucleic acid encoding a protein as given in SEQ ID NO 3 or as defined in (a) to (f), which are diverging due to the differences between alleles, (j) nucleic acid encoding a fragment of a protein as given in SEQ ID NO 3 or consisting of a fragment of a nucleic acid as defined in (a) to (i), (k) nucleic acid encoding a protein as defined in SEQ ID NO 3 interrupted by intervening DNA sequences or nucleic acid as defined in any one of (a) to (j) interrupted by intervening DNA sequences and (l) nucleic acid representing the complement of any of said nucleic acids as defined in (a) tot (k), provided that said nucleic acid is not the nucleic acid as deposited under the GenBank accession numbers AW438153 or BF728697.

The present invention also relates to an isolated nucleic acid as defined above encoding a polypeptide or fragment thereof which binds to a DRE cis regulatory DNA sequence, for instance a DRE sequence as given in SEQ ID NO 1.

The DRE sequence as given in SEQ ID NO 1 comprises three tandem repeats of the DRE2 element.

The present invention also relates to an isolated nucleic acid sequence encoding an AP2/EREBP domain-containing transcription factor or fragment thereof which binds to a cis regulatory DNA sequence and for which the intensity of such binding is regulated by ABA. One example of such a cis regularatory DNA sequence according to the invention is a DRE element, for instance a DRE element as given in SEQ ID NO 1.

The intensity of binding can be measured by several methods known by the person skilled in the art. One example of an in vivo method is the use of the Yeast One-Hybrid technique as described in example 1. Herein the intensity of color produced by the enzyme of the reporter gene is representative for the intensity of binding between the protein to the oligonucleotide. An alternative method is for instance an in vitro protein-DNA binding experiment. Results may be measured via electrophoretic gel shift assay techniques as described in example 6. Further, the intensity of the binding may be measured by competition assays for instance as described in example 6.

The present invention also relates to an isolated nucleic acid encoding an AP2/EREBP domain-containing transcription factor or fragment thereof which binds to a cis regulatory DNA sequence and which activates the transcription of the sequences regulated by said cis regulatory element in response to ABA. One example of such a cis regularatory DNA sequence according to the invention is a DRE element, for instance a DRE element as given in SEQ ID NO 1.

The present invention also relates to an isolated nucleic acid encoding an AP2/EREBP domain-containing transcription factor or an immunologically active or functional fragment thereof comprising a sequence as represented in SEQ ID NO 14, or comprising a sequence which is at least 50%, more preferably 60%, and most preferably at least 70% or 75% identical to SEQ ID NO 14: PLXXXV(D/N)AKL(Q/E)XIC.

The present invention also relates to an isolated nucleic acid of the invention as defined above which is cDNA, DNA, genomic DNA or synthetic DNA, or RNA wherein T is replaced by U.

The present invention also relates to any of the isolated nucleic acids as defined above but which is derived from a monocotyledonous plant.

The present invention also relates to a nucleic acid molecule of at least 15 nucleotides in length hybridizing specifically with a nucleic acid of the invention as described above.

The present invention also relates to a nucleic acid molecule of at least 15 nucleotides in length specifically amplifying a nucleic acid of the invention as described above.

The present invention also relates to a polypeptide encoded by any of the nucleic acids of the invention as described above.

The present invention also relates to a vector comprising any of the nucleic acid sequences of the invention as described above.

The present invention also relates a vector of the invention as described above which is an expression vector wherein said nucleic acid sequence is operably linked to one or more control sequences allowing the expression in prokaryotic and/or eukaryotic host cells.

The present invention also relates to a host cell containing a nucleic acid molecule or a vector of the invention as described above.

The present invention also relates to a host cell of the invention as described above selected from the group consisting of a bacterial, insect, fungal, plant or animal cell.

The present invention also relates to a method for the production of transgenic plants, plant cells or plant tissue comprising the introduction of a nucleic acid of the invention as described above or a vector of the invention as described above into the genome of a plant, plant cell or plant tissue.

The present invention also relates to a method of the invention as described above further comprising regenerating a plant from said plant tissue or plant cell.

The present invention also relates to a transgenic plant cell comprising a nucleic acid of the invention as described above which is operably linked to regulatory elements allowing transcription and/or expression of the nucleic acid sequence in plant cells or obtainable according to the method of the invention as described above.

The present invention also relates to the transgenic plant cell of the invention as described above wherein said nucleic acid sequence or said-vector is stably integrated into the genome of the plant cell.

The present invention also relates to a transgenic plant or a plant tissue comprising plant cells of the invention as described above.

The present invention also relates to homologues, analogues or paralogues of the DBF1 proteins (and nucleic acids) of the invention and to the uses thereof.

One interesting example is a rice DBF1 homologue that clusters closely with DBF1 as shown in FIG. 7. The DNA sequence of the rice homologue is represented in SEQ ID NO 15 and the corresponding protein sequence is represented in SEQ ID NO 16 (see example 8).

The present invention also relates to a method for the production of transgenic plants, said plants characterized as having increased growth and/or yield under stressed and/or non-stressed conditions, said method comprising:

a) introducing a nucleic acid or a vector of the invention as described above into the genome of a plant cell or plant tissue, or, b) introducing a nucleic acid comprising a sequence as represented in SEQ ID NO 15 or a homologure or analogue- or paralogue thereof, or a vector comprising the sequence as represented in SEQ ID NO 15 into a plant cell or plant tissue, c) regenerating plants from said transformed plant cells or plant tissues, and, d) selecting a plant exhibiting said increased growth and/or yield.

The present invention also relates to a method for the production of transgenic plants, said plants characterized as having increased expression of at leas one stress-related protein, said method comprising:

a) introducing a nucleic acid or a vector of the invention as described above into the genome of a plant cell or plant tissue, or b) introducing a nucleic acid comprising a sequence as represented in SEQ ID NO 15, or a homologure or analogue or paralogue thereof, or a vector comprising the sequence as represented in SEQ ID NO 15 into a plant cell or plant tissue c) regenerating plants from said transformed plant cells or plant tissues, and, d) selecting a plant exhibiting said increased expression of said stress-related protein.

The present invention also relates to a transgenic plant obtainable by any of the methods of the invention as described above.

The present invention also relates to a transgenic plant of, the invention as described above or obtainable by any of the methods of the invention as described above wherein said plant is a monocotyledonous plant.

The present invention also relates to plant tissue derived from a plant of the invention as described above or from a plant obtainable by a method of the invention as described above.

The present invention also relates to a harvestable part or propagule derived from a plant of the invention as described above or from a plant obtainable by a method of the invention as described above.

The present invention also relates to the harvestable part of the invention as described above which is selected from the group consisting of seeds, leaves, roots, flowers, fruits, stems, rhizomes, tubers and bulbs.

The present invention also relates to the progeny derived from any of the plants, plant tissues or plant parts of the invention as described above.

The present invention also relates to a method for diagnosing changes in mRNA expression in different cells, tissues, or organs of plants and under different environmental conditions wherein a nucleic acid of the invention as described above or a nucleic acid as represented in SEQ ID NO 15, or a homologue or an analogue or a paralogue thereof, is used.

The present invention also relates to a method for diagnosing inheritance of growth and/or yield-related traits in crop breeding programs wherein a nucleic acid of the invention as described above or a nucleic acid as represented in SEQ ID NO 15, or a homologue or an analogue or a paralogue thereof, is used as molecular marker.

The present invention also relates to a method for identifying allelic variants of such sequences in crop breeding programs wherein a nucleic acid of the invention as described above or a nucleic acid as represented in SEQ ID NO 15, or a homologue or an analogue or a paralogue thereof, is used.

The present invention also relates to a method for identifying chemical compounds that modify growth and/or stress tolerance of plants, comprising:

(a) combining a polypeptide of the invention as described above or a polypeptide comprising a sequence as represented in SEQ ID NO 16, with said compound or mixtures of compounds under conditions suitable to allow complex formation, and, (b) detecting complex formation, wherein the presence of a complex identifies a compound which specifically binds said polypeptide.

The present invention also relates to the use of a compound or a mixture of compounds obtainable by a method of the invention as described above as growth regulator and/or herbicide.

The present invention also relates to a method for identifying polypeptides that interact with a polypeptide of the invention as described above or a polypeptide comprising a sequence as represented in SEQ ID NO 16, comprising a two-hybrid screening assay wherein at least one polypeptide of the invention or a polypeptide comprising a sequence as represented in SEQ ID NO 16, as a bait and a cDNA library of a plant or plant part as prey are expressed.

The present invention also relates to a method for identifying and obtaining nucleic acids encoding DRE(2) binding polypeptides comprising a one hybrid screening assay wherein a DRE element, such as a sequence as represented in SEQ ID NO 1 comprising one or to more DRE elements, as a bait and a cDNA library of a monocotyledonous plant or plant part as prey are expressed.

The present invention also relates to a method for identifying and containing nucleic-acids encoding DNA-binding polypeptides that modify ABA- and stress-related responses in plants comprising a one hybrid screening assay wherein a DRE element, such as a sequence as represented in n SEQ ID NO 1 comprising one or more DRE elements, or a sequence which is at least 70% identical to SEQ ID NO 1 is used as a bait and a cDNA library of a monocotyledonous plant or plant part as prey are expressed.

The present invention also relates to an isolated polypeptide obtainable by any of the methods of the invention as described above.

The present invention also relates to an antibody specifically recognizing the nucleic acid sequence as given in SEQ ID NO 1.

The present invention also relates to an antibody specifically recognizing a polypeptide of the invention as described above dr a specific epitope thereof.

The present invention also relates to a nucleic acid encoding at least one antibody polypeptide of the invention as described above.

The present invention also relates to a vector comprising a nucleic acid encoding at least one of the antibodies of the invention as described above.

The present invention also relates to the vector of the invention as described above which is an expression vector wherein said nucleic acid is operably linked to one or more control sequences allowing the expression in prokaryotic and/or eukaryotic host cells.

The present invention also relates to a method for the production of transgenic monocotyledonous plants, said plants characterized as having, increased expression of at least one stress-related protein, and/or showing improved stress tolerance, and/or giving higher yield and better growth, said method comprising:

(a) introducing a nucleic acid or a vector of the invention as described above into the genome of a plant cell or plant tissue, (b) regenerating plants from said transformed plant cells or plant tissues, and (c) selecting a plant exhibiting said increased expression.

Surprisingly, the present inventors found that the rab17 promoter of maize is not inducible anymore by ABA when it is expressed in *Arabidopsis*, which demonstrates that the signaling components involved in ABA control of DRE2 elements are either absent in *Arabidopsis* or are functionally not conserved between *Arabidopsis* and maize.

Alternatively, the signaling components involved in ABA control of DRE2 elements are present in *Arabidopsis*, but the context of the maize rab17 promoter is not the appropriate context to allow binding of these orthologous *Arabidopsis* proteins as identified in the present invention in the genome of *Arabidopsis* to the DRE element.

Therefore, in an interesting embodiment of the present invention, the nucleic acids or the polypeptides of the present invention are derived from a monocotyledonous plant; the host cells and transgenic plants of the present invention are monocotyledonous cells or plants; and the methods of the present invention are to be used in monocotyledonous cells, tissues or plants.

Alternatively in a related particular embodiment of the present invention, the nucleic acids of the present invention or the polypeptides are derived from a dicot, the host cells and transgenic plants of the present invention are a dicot, or the methods of the present invention are to be used in dicots.

Footprinting experiments revealed that protein binding to the DRE2 element occurred both in maize embryos and leaves under non-stressed conditions, but that binding increased and/or intensified after water stress or ABA application (Busk et al., Plant J. 11:1285-1295, 1997). In order to characterize the proteins binding to the DRE2 element, yeast one-hybrid screenings were performed using three tandem repeats of the 19 bp DRE2 element (SEQ ID NO 1) as bait (see Example 1). Two different clones that bind to DRE2 were identified from a cDNA library of water-stressed leaves. Each of these clones was isolated several times from an independent experiment, which supports the validity of the interaction. This result demonstrates that the DRE2 element constitutes a functional cis-acting promoter element for gene expression and teaches how to isolate proteins binding DRE2 from maize or other species. The identification of DRE2 as a regulatory cis element involved in ABA responses also allows to screen promoters of other genes for sequences that are identical or highly similar to DRE2 and to isolate polypeptides binding to such elements. Therefore, in one embodiment of the invention, a method is claimed for identifying and obtaining DRE-2-binding polypeptides comprising a one hybrid screening assay wherein SEQ ID NO 1 as a bait and a cDNA library of a monocotyledonous plant or plant part as a prey are used. Similarly, a me hod is claimed for identifying and obtaining DNA-binding polypeptides that modify ABA- and stress-related responses in plants comprising a one hybrid screening assay wherein a sequence that is at least 70% identical to SEQ ID NO 1 is used as a bait and a cDNA library of a monocotyledonous plant or plant part is used as a prey.

One of the DRE2 binding clones was designated DBF1, which stands for DRE-Binding Factor 1. The DNA and amino acid sequences of DBF1 are given in SEQ ID NO 2 and SEQ ID NO 3 (see Example 2). DBF1 contains a sixty amino acid region that constitutes a DNA binding domain, the AP2 domain, which is highly conserved in the members of the AP2/EREBP family of plant transcription factors (FIG. 1). Remarkably, the amino acid sequences of DBF1 shows no significant homology outside this region with the reported members of the AP2/EREBP family, including CBF1, DREB1A, and DREB2A, which bind DRE/CRT elements in *Arabidopsis*. This implies that the role of DBF1 as DRE2 binding protein and as a signal protein in ABA responses (see below) cannot simply be inferred from DNA or amino acid sequence similarity to known AP2/EREBP family members. This is further illustrated by a Blast search for sequence similarity against a non-redundant protein database (Example 3): highest similarities with DBF1 were found with 6 *Arabidopsis* AP2/EREBP proteins of unknown function (E values of $e^{-44}$ to $e^{-39}$). All AP2/EREBP proteins of known function had similarity scores of $e^{-20}$ or lower. The CBF1, DREB1A, and DREB2A had E values of $e^{-16}$ to $e^{-15}$ and there were about 50 other proteins of the AP2/EREBP family in *Arabidopsis* that had similarity values to DBF1 that fall within the same range. Most of these are of unknown function, while some others have been implicated in hormone responses, primarily to ethylene. Only one of these, named ABI4, has previously been implicated in ABA responses, but its precise function or mode of action remains currently unknown (Finkelstein et al., Plant Cell 10:1043-1054, 1998). ABI4 has an E value of $e^{-19}$, and thus is not particularly closely related in structure to DBF1.

The role of DBF1 in ABA responses and dehydration stress was further substantiated by the following data. First, the expression pattern of DBF1 is in line with such a role (Example 4). DBF1 was strongly transcribed after dehydration treatment in all vegetative parts and was also induced by salt and ABA, with highest expression levels in roots (FIG. 2). This expression pattern is similar to that of rab17, in accordance with a role of DBF1 upstream of rab17. Analysis of the kinetics of this induction showed that DBF1 mRNA levels increased in less than one hour (FIG. 3). DBF1 was also expressed strongly in maize embryos and this expression was also inducible by ABA. Dehydration-related genes, including rab17, are also expressed during embryogenesis, in order to protect the embryo during seed desiccation. Therefore, these data indicate that DBF1 not only controls dehydration responses during environmental stress but also during development of DBF1 protein profiles, detected using antibodies raised against the DBF1 protein, were congruent with the above-mentioned DBF1 mRNA patterns (FIG. 4).

Second, overexpression of DBF1 was shown to potentiate the ABA response in maize callus cells (Example 5). A rab17 promoter-GUS fusion was expressed in maize callus cells, half of which were cultured in the presence of ABA and half without. DBF1 expression induced promoter activity, both in the presence and absence of ABA (FIG. 5). Furthermore, mutation of the DRE2 element in the rab17 promoter-GUS fusion reduced promoter activity and its responsiveness to ABA. Taken together, these data demonstrate that DBF1, through binding with the DRE2 element, regulates ABA responses and stress defense mechanisms.

Apart from binding to DRE2, other modes of action of DBF1 are not excluded. DBF1 does not bind to DRE1 or ABRE elements (FIG. 6, Example 6), which are also located in the rab17 promoter. Yet, it is proposed that DBF1 may promote binding and/or activity of factors binding to DRE1, ABRE or other rab17 promoter elements. In accordance with such a model, interactions between b-ZIP factors, which bind ABRE elements, and AP2/EREBP domain proteins have been demonstrated in relation to other cis regulatory elements (Büttner and Singh, Proc. Natl. Acad. Sci. USA 94: 5961-5966, 1997). Thus, without being bound to a mode of action, we propose that DBF1 takes part in the control of ABA responses and activation of stress defense mechanisms in maize.

It is however not excluded that DBF1 is able to bind also other cis elements than DRE2. Taken together, the data presented herein are the first to show that ABA regulation of DRE cis elements in maize involves AP2/EREBP domain transcription factors. The data of this invention are also the first to describe the DNA and protein sequence of an AP2/EREBP domain transcription factor with a function in ABA signaling and to show that this protein is structurally quite divergent from AP2/EREBP domains of known function. Both the role of AP2/EREBP domain transcription factors in ABA signaling and the specific sequence of an AP2/EREBP domain transcription factor with such function were hitherto unknown and, as a consequence, the presented invention and its embodiments could not be envisaged.

Given the close phylogenetic relationship of cereal species, a person skilled in the art will be able to identify proteins with a function similar to DBF1 from other cereals, or from other monocots. In addition, DRE-binding factors in *Arabidopsis* are part of gene families, therefore, it is likely that maize and other cereals contain several genes which code for proteins that are structurally and functionally related to DBF1. Methods to identify homologs of DBF1 from the same or other species include, but are not limited to, sequence alignment, DNA or RNA hybridizations, one hybrid screens with the DRE1 element or protein affinity purification with the DRE1 element.

The sequence of the DBF1 protein, functional in the invention, need therefore not to be identical to that described herein. It is envisaged that other proteins with a highly similar structure as DBF1 can also be used for the purpose of this invention. The embodiments described below refer to polypeptides selected from the group consisting of:

(a) polypeptide sequences comprising at least part of the protein sequence, as given in SEQ ID NO 3, (b) polypeptide sequences constituting a protein or fragment thereof that binds to a cis regulatory DNA sequence as given in SEQ ID NO 1, (c) polypeptide sequences constituting an AP2/EREBP domain-containing transcription factor or fragment thereof that binds to a cis regulatory DNA sequence and for which the intensity of such binding is regulated by ABA, (d) polypeptide sequences constituting an AP2/EREBP domain-containing transcription factor or fragment thereof that binds to a cis regulatory DNA sequence and that activates the transcription of the sequences regulated by this cis regulatory element in response to ABA, (e) polypeptide sequences constituting an AP2/EREBP domain-containing transcription factor or fragment thereof which contain a peptide that is at least 50% and preferably 70% identical, or more, to SEQ ID NO 14, (f) protein sequences constituting a full-length AP2/EREBP domain-containing transcription factor which are at least 35% or 37% identical, more preferable 40%, and most preferable 45% identical, or more, to the amino acid sequence of SEQ ID NO 3.

In one embodiment of the invention, modified expression of DBF1, or another polypeptide according to the above description, in transgenic plants will provide such plants with a trait of commercial value. Modification of DBF1 expression, or of another polypeptide according to the above description is preferentially accomplished by fusing the polypeptide coding sequence to a heterologuous promoter and transforming such fusion in a expressable mode in transgenic plants. The plant is preferably a cereal, such as maize, wheat, rice, barley, or sorghum.

In another embodiment of the invention, a method is claimed for the production of transgenic monocotyledonous plants, said plants characterized as having increased expression of at least one stress-related protein, such as Rab17, said method comprising the transformation of a nucleic acid encoding DBF1 or another polypeptide according to the above description in an expressable form into a transgenic plant, preferable a cereal, such as maize, wheat, rice, barley, or sorghum.

In another embodiment of the invention, expression of DBF1, or another polypeptide according to the above description, under control of a strong constitutive promoter will enhance the tolerance of plants to environmental stress, in particular dehydration stress. The plant is preferably a cereal, such as maize, wheat, rice, barley, or sorghum.

In another embodiment of the invention, expression of DBF1, or another polypeptide according to the above description, under control of a stress-inducible promoter will enhance the tolerance of plants to environmental stress, in particular dehydration stress. The plant is preferably a cereal, such as maize, wheat, rice, barley, or sorghum.

In another embodiment of the invention, expression of DBF1, or another polypeptide according to the above description, under control of a tissue-specific promoter will enhance the tolerance of plant organs that are particularly prone to environmental stress, in particular dehydration stress. The plant is preferably a cereal, such as maize, wheat, rice, barley, or sorghum. The promoter is preferably expressed either in roots, shoots or anthers.

In another embodiment of the invention, expression of DBF1, or another polypeptide according to the above description, under control of a developmentally controlled promoter will enhance the tolerance of plants at specific developmental stages that are particularly prone to environmental stress, in particular dehydration stress. The plant is preferably a cereal, such as maize, wheat, rice, barley, or sorghum. The promoter is preferably expressed either in pollen, ovules, or seeds.

In another embodiment of the invention, expression of DBF1, or another polypeptide according to the above description, under control of a DRE1 containing promoter will enhance the tolerance of plants against environmental stress, in particular dehydration stress. The plant is preferably a cereal, such as maize, wheat, rice, barley, or sorghum. Interestingly, the present results showed that mutation of the DRE2 element does not completely abolish Rab17 promoter activity or ABA responsiveness, although it does annul binding of DBF1. This indicates that Rab17 promoter activity and ABA responsiveness is a superposition of several regulatory pathways which exert additive effects. It is proposed therefore that combined overexpression of DBF1 with transcription factors mediating ABA responses through cis elements other than DRE, will have stronger effects on the expression of stress response proteins, such as Rab17, than overexpression of DBF1 alone. Candidate proteins for coexpression with DBF1 are molecules that are known in the existing art as signaling molecules of the ABA responsive pathway to stress such as ABRE binding factors of the b-zip family, such as EmBP-1 (Guiltinan et at., Science 250:267-271, 1990; Gupta et al., Plant Mol. Biol. 37:629-637, 1998) and MYB/MYC proteins involved in ABA signaling (Abe et al, Plant Cell 9:1859-1868, 1999). Since binding of bZIP factors to ABRE elements is enhanced by interaction with C2H2 type zinc finger proteins, such as SCOF-1 (Jong et al, Abstract S31-46, Book of Abstracts of the ISPMB meeting in Quebec, June 18-24, 2000, Supplement to Reporter 18:2), even higher expression levels of, stress-responsive genes, such as Rab17, are proposed when overexpression of DBF1, b-zip factors and C2H2-type zinc finger proteins, is combined in a single plant.

Preferred embodiments of the invention therefore also include the overexpression of DBF1 in combination with signaling proteins of other ABA pathways controlling gene activation.

In another embodiment of the invention, modified expression of DBF1, or another polypeptide according to the above description, combined with modified expression of an ABRE binding factor of the bZIP family, in transgenic plants will enhance the tolerance of plants against environmental stress, in particular dehydration stress. The plant is preferably a cereal, such as maize, wheat, rice, barley, or sorghum. The promoters used for driving expression of these proteins are preferentially either constitutive and/or ubiquitous, stress-inducible, tissue-specific or developmentally controlled.

In another embodiment of the invention, modified expression of DBF1, or another polypeptide according to the above description, combined with modified expression of a MYC factor that is inducible by ABA, in transgenic plants will enhance the tolerance of plants against environmental stress, in particular dehydration stress. The plant is preferably a cereal, such as maize, wheat, rice, barley, or sorghum. The promoters used for driving expression of these proteins are preferentially either constitutive and/or ubiquitous, stress-inducible, tissue-specific or developmentally controlled.

In another embodiment of the invention, modified expression of DBF1, or another polypeptide according to the above description, combined with modified expression of a C2H2-type zinc finger protein that binds ABRE binding factors of the bZIP family, in transgenic plants will enhance the tolerance of plants against environmental stress, in particular dehydration stress. The plant is preferably a cereal, such as maize, wheat, rice, barley, or sorghum. The promoters used for driving expression of these proteins are preferentially either constitutive and/or ubiquitous, stress-inducible, tissue-specific or developmentally controlled.

In another embodiment of the invention, modified expression of DBF1, or another polypeptide according to the above description, combined with modified expression of a MYB factor that is inducible by ABA, in transgenic plants will enhance the tolerance of plants against environmental stress, in particular dehydration stress. The plant is preferably a cereal, such as maize, wheat, rice, barley, or sorghum. The promoters used for driving expression of these proteins are preferentially constitutive, stress-inducible, tissue-specific or developmentally controlled.

In another embodiment of the invention, modified expression of proteins of the following classes in a single transgenic plant will enhance the tolerance against environmental stress, in particular dehydration stress: DBF1, or another polypeptide according to the above description, combined with an ABRE binding factor of the bZIP family, combined with a C2H2-type zinc finger protein that binds ABRE binding factors of the bZIP family. The plant is preferably a cereal, such as maize, wheat, rice, barley, or sorghum. The promoters used for driving expression of these proteins are preferentially either constitutive and/or ubiquitous, stress-inducible, tissue-specific or developmentally controlled.

In another embodiment of the invention, modified expression of proteins of the following classes in a single transgenic plant will enhance the tolerance against environmental stress, in particular dehydration stress: DBF1, or another polypeptide according to the above description, combined with a MYC factor of which the expression is inducible by ABA, combined with a MYB factor of which the expression is inducible by ABA. The plant is preferably a cereal, such as maize, wheat, ride, barley, or sorghum. The promoters used for driving expression of these proteins are preferentially either constitutive, stress-inducible, tissue-specific or developmentally controlled.

In another embodiment of the invention, modified expression of proteins of the following classes in a single transgenic plant will enhance the tolerance against environmental stress, in particular dehydration stress: DBF1, or another polypeptide according to the above description, combined with an ABRE binding factors of the bZIP family, combined with a C2H2-type zinc finger protein that binds ABRE binding factors of the bZIP-family, combined with a MYC factor of which the expression is inducible by ABA, combined with a MYB factor of which the expression is inducible by ABA. The plant is preferably a cereal, such as maize, wheat, rice, barley, or sorghum. The promoters used for driving expression of these proteins are preferentially either constitutive, stress-inducible, tissue-specific or developmentally controlled.

Alternatively, the expression of DBF1 is combined with the expression with (at least one) other signaling molecule of the ABA-independent pathway (such as DRE binding proteins) in order to potentiate the effect on expression of genes carrying in their promoter a DRE element, such as stress responsive genes (rd29A or Rab17 etc). Examples of such DRE binding proteins to be combined with the DBF1 protein of the present invention are: CBF1-like proteins (Stockinger et al, Proc Natl Acad Sci 94:1035-1040, 1997) or DREB1 A or DREB2A (Liu et al., Plant Cell 10:1391-1406, 1998).

Furthermore in a particular embodiment of the present invention it is the purpose to combine both known stress responsive pathways together, i.e. to combine the ABA-dependent pathway and ABA-independent pathway. This is particularly done by combining the expression of signaling molecules involved in these pathways, examples of which are described above. Accordingly in a particular embodiment of the present invention, the expression of the DBF1 molecule is combined with a signaling molecule of the ABA-dependent pathway as well as with a signaling molecule of the ABA-independent pathway.

The zmDBF1 protein as identified in the present invention also has homologues in other plant species. The inventors were able to identify the closest *Arabidopsis* homologues: AAF87854 and T02511, the closest *Atriplex hortensis* homologue: AAF76898 and the closest *Lupinus polyphyllis* homologue PZ02-LUPPO. As for monocotyledonous plants, more particularly crop plants, also sugar cane DBF1 homologues and rice DBF1 homologues were found. One example of a rice DBF1 homologue that clusters closely with DBF1 is shown in FIG. 7. The DNA sequence of the rice homologue is represented in SEQ ID NO 15 and the corresponding protein sequence is represented in SEQ ID NO 16 (see example 8).

Accordingly in an interesting embodiment, the present invention relates to the use of homologues of the ZmDBF1 nucleic acids and proteins for all the applications described for ZmDBF1 nucleic acids and proteins but with said nucleic acids and proteins derived from other plant species.

A more particular embodiment of the present invention relates to the use of the rice DBF1 homologues as presented in SEQ ID NO 15 for instance in a vector according to the present invention and/or in the host cells and the transgenic plants of the present invention and/or in the methods as described in the present invention.

The invention thus also relates to a vector, a host cell or a transgenic cell, issue or plant comprising a nucleic acid having a sequence as represented in SEQ ID NO 15.

The invention further relates to the use of any of the sequences as represented in SEQ ID NO 15 or 16, or a vector or a host cell comprising said any of said sequences in any of the methods herein described.

The genes and the methods of the present invention are particularly useful for the production of host cells or host organisms with modulated (e.g. increased) growth and/or yield under stressed and/or non-stressed conditions. This can be achieved by directly influencing the level of expression and/or the level of activity of the DBF1 genes or DBF1 proteins of the present invention and the homologues thereof in said host cell or host organism. More in particular influencing the level of expression and or activity of DBF1 may be achieved by using the endogenous DBF1 gene or DBF1 protein of the host cell, or by using a DBF1 transgene, or by using an exogenous DBF1 protein.

Alternatively, modulating growth and/or yield with the genes and methods of the present invention can also be achieved indirectly by influencing the level of expression and/or activity of other genes of interest, for example other stress tolerance or stress-inducible genes, or other growth regulatory genes. This may be done by making a construct in which that particular gene is put under the control of a promoter containing at least one DRE element, and simultaneously introducing that construct into a host cell together with the DBF1 protein of the present invention. The effect is that the DBF1 protein may be able to activate the expression of said gene and to confer altered growth characteristics to that host cell.

The simultaneous introduction of the DBF1 protein with said construct may be achieved in alternative ways: the endogenous DBF1 gene or protein of the host cell may be activated, a DBF1 encoding transgene may be introduced in the host cell, or the DBF1 protein may be administered to the host cell.

Definitions and Elaborations to the Embodiments

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any or more of said steps or features.

Throughout this specification, unless the context requires otherwise the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source.

The terms "protein(s)", "peptide(s)" or "oligopeptide(s)", when used herein refer to amino acids in a polymeric form of any length. Said terms also include known amino acid modifications such as disulphide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamines, deoxyhexoses, hexoses, sialic acid etc.), acylation and radiolabels (e.g. $^{125}$I, $^{131}$I, $^{35}$S, $^{14}$C, $^{32}$P, $^{33}$P, $^{3}$H) as well as non-naturally occurring amino acid residues, L-amino acid residues and D-amino acid residues.

TABLE 1

Properties of naturally occurring amino acids.

| Charge properties/ hydrophobicity | Side group | Amino Acid |
|---|---|---|
| nonpolar hydrophobic | aliphatic | Ala, Ile, Leu, Val |
| | aliphatic, S-containing | Met |
| | aromatic | Phe, Trp |
| | imino | Pro |
| polar uncharged | aliphatic | Gly |
| | amide | Asn, Gln |
| | aromatic | Tyr |
| | hydroxyl | Ser, Thr |
| | sulfhydryl | Cys |
| positively charged | basic | Arg, His, Lys |
| negatively charged | acidic | Asp, Gly |

"Homologues" or "Homologs" of a protein of the invention are those peptides, oligopeptides, polypeptides, proteins and enzymes which contain amino acid substitutions, deletions and/or additions relative to the said protein with respect to which they are a homologue without altering one or more of its functional properties, in particular without reducing the activity of the resulting. For example, a homologue of said protein will consist of a bioactive amino acid sequence variant of said protein. To produce such homologues, amino acids present in the said protein can be replaced by other amino acids having similar properties, for example hydrophobicity, hydrophilicity, hydrophobic moment, antigenicity, propensity to form or break α-helical structures or β-sheet structures, and so on. An overview of physical and chemical properties of amino acids is given in Table 1.

Two special forms of homology, orthologous and paralogous, are evolutionary concepts used to describe ancestral relationships of genes. The term " paralogous" relates to gene-duplications within the genome of a species leading to paralogous genes. The term "orthologous" relates to homologous genes in different organisms due to ancestral relationship. The present invention thus also relates to homologues, paralogues and orthologues of the proteins according to the invention.

Substitutional variants of a protein of the invention are those in which at, least one residue in said protein amino acid sequence has been removed and a different residue inserted in its place. Amino acid substitutions are typically of single residues, but may be clustered depending upon functional constraints placed upon the polypeptide; insertions will usually be of the order of about 1-10 amino acid residues and deletions will range from about 1-20 residues. Preferably, amino acid substitutions will comprise conservative amino acid substitutions, such as those described supra.

Insertional amino acid sequence variants of a protein of the invention are those in which one or more amino acid residues are introduced into a predetermined site in said protein. Insertions can comprise amino-terminal and/or carboxy-terminal fusions as well as intra-sequence insertions of single or multiple amino acids. Generally, insertions within the amino acid sequence will be smaller than amino or carboxyl terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)$_6$-tag, glutathione S-transferase, protein A, maltose-binding protein, dihydrofolate reductase, Tag•100 epitope (EETARFQPGYRS) (SEQ ID NO: 17), c-myc epitope (EQKLISEEDL) (SEQ ID NO: 18), FLAG®-epitope (DYKDDDK) (SEQ ID NO: 19), lacZ, CMP (calmodulin-binding peptide), HA epitope (YPYDVPDYA) (SEQ ID NO: 20), protein C epitope (EDQVDPRLTDGK) (SEQ ID NO: 21) and VSV epitope (YTDIEMNRLGK) (SEQ ID NO: 22).

Deletional variants of a protein of the invention are characterised by the removal of one or more amino acids from the amino acid sequence of said protein.

Amino acid variants of a protein of the invention may readily be made using peptide synthetic techniques well known in the art, such as solid phase peptide synthesis and the like, or by recombinant DNA manipulations. The manipulation of DNA sequences to produce variant proteins, which manifests as substitutional, insertional or deletional variants are well known in the art. For example, techniques for making substitution mutations at predetermined sites in DNA having known sequence are well known to those skilled in the art, such as by M13 mutagenesis, T7-Gen in vitro mutagenesis kit (USB, Cleveland, Ohio), QuickChange Site Directed mutagenesis kit (Stratagene, San Diego, Calif.), PCR-mediated site-directed mutagenesis or other site-directed mutagenesis protocols. Another alternative to manipulate DNA sequences to produce variant proteins, which manifest as substitutional, insertional or deletional variants comprises targeted in vivo gene modification which can be achieved by chimeric RNA/DNA oligonucleotides as described by e.g. (Palmgren 1997; Yoon et al. 1996).

The "E-value" is used to indicate the expectation value. The number of different alignments with scores equivalent to or better than S that are expected to occur in a database search by chance. The lower the E value, the more significant the score.

"Derivatives" of a protein of the invention are those peptides, oligopeptides, polypeptides, proteins and enzymes which comprise at least about five contiguous amino acid residues of said polypeptide but which retain the biological activity of said protein. A "derivative" may further comprise additional naturally-occurring, altered glycosylated, acylated or non-naturally occurring amino acid residues compared to the amino acid sequence of a naturally-occurring form of said polypeptide. Alternatively or in addition, a derivative may comprise one or more non-amino acid substituents compared to the amino acid sequence of a naturally-occurring form of said polypeptide, for example a reporter molecule or other ligand, covalently, or non-covalently bound to the amino acid sequence such as, for example, a reporter molecule which is bound thereto to facilitate its detection.

With "immunologically active" is meant that a molecule or specific fragments thereof such as epitopes or haptens are recognised by, i.e. bind to antibodies.

In the context of the current invention are embodied homologous, derivatives and/or immunologically active fragments of any of the inventive DRE-binding factor (DBF1) or homologue, derivative or fragment thereof as defined supra.

"Antibodies" include monoclonal, polyclonal, synthetic or heavy chain camel antibodies as well as fragments of antibodies such as Fab, Fv or scFv fragments. Monoclonal antibodies can be prepared by the techniques as described previously e.g. (Liddle & Cryer 1991) which comprise the fusion of mouse myeloma cells to spleen cells derived from immunised animals. Furthermore, antibodies or fragments thereof to a molecule or fragments thereof can be obtained by using methods as described in e.g. (Harlow & Lane 1988). In the case of antibodies directed against small peptides such as fragments of a protein of the invention, said peptides are generally coupled to a carrier protein before immunisation of animals. Such protein carriers include keyhole limpet hemocyanin (KLH), bovine serum albumin (BSA), ovalbumin and Tetanus toxoid. The carrier protein enhances the immune response of the animal and provides epitopes for T-cell receptor binding sites. The term "antibodies" furthermore includes derivatives thereof such as labelled antibodies. Antibody labels include alkaline phosphatase, PKH2, PKH26, PKH67, fluorescein (FITC), Hoechst 33258, R-phycoerythrin (PE), rhodamine (TRITC), Quantum Red, Texas Red, Cy3, biotin, agarose peroxidase, gold spheres and radiolabels (e.g. $^{125}$I, $^{131}$I, $^{35}$S, $^{14}$P, $^{32}$P, $^{33}$P, $^{3}$H). Tools in molecular biology relying on antibodies against a protein include protein gel blot analysis, screening of expression libraries allowing gene identification, protein quantitative methods including ELISA and RIA, immunoaffinity purification of proteins, immunoprecipitation of proteins e.g. (Magyar et al. 1997) and immunolocalization. Other uses of antibodies and especially of peptide antibodies include the study of proteolytic processing (Loffler et al. 1994; Woulfe et al. 1994), determination of protein active suites (Lerner 1982), the study of precursor and post-translational processing (Baron & Baltimore 1982; Lerner et al. 1981; Semler et al. 1982), identification of protein domains involved in protein-protein interactions (Murakami et al. 1992) and the study of exon usage in gene expression (Tamura et al. 1991).

Embodied in the current invention are antibodies recognising a DRE-binding factor such as DBF1 or homologue, derivative or fragment thereof as defined supra.

The terms "gene(s)", "polynucleotide(s)", "nucleic acid, sequence(s)", "nucleotide sequence(s)", "DNA sequence(s)" or "nucleic acid molecule(s)", when used herein refer to nucleotides, either ribonucleotides or deoxyribonucleotides or a combination of both, in a polymeric form of any length. Said terms furthermore include double-stranded and single-stranded DNA and RNA. Said terms also include known nucleotide modifications such as methylation, cyclization and 'caps' and substitution of one or more of the naturally occurring nucleotides with an analogue such as inosine. Modifications of nucleotides include the addition of acridine, amine, biotin, cascade blue, cholesterol, Cy3®, Cy5®, Cy5.5® Dabcyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S®, SE, BODIPY®, Marina Blue®, Pacific Blue®, Oregon Green®, Rhodamine Green®, Rhodamine Red®, Rhodol Green® and Texas Red®. Polynucleotide backbone modifications include methylphosphonate, 2'-OMe-methylphosphonate RNA, phosphorothioate, RNA, 2-OMeRNA. Base modifications include 2-amino-dA, 2-aminopurine, 3'-(ddA), 3'-dA(cordycepin), 7-deaza-dA, 8-Br-dA, 8-oxo-dA, N$^6$-Me-dA, abasic site (dSpacer), biotin dT, 2'-OMe-5Me-C, 2'-OMe-propynyl-C, 3'-(5-Me-dC), 3'-(ddC), 5-Br-dC, 5-I-dC, 5-Me-dC, 5-F-dC, carboxy-dT, convertible dA, convertible dC, convertible dG, convertible dT, convertible dU, 7-deaza-dG, 8-Br-dG, 8-oxo-dG, O$^6$-Me-dG, S6-DNP-dG, 4-methyl-indole, 5-nitroindole, 2'-OMe-inosine, 2-dl 06-phenyl-dl, 4-methyl-indole, 2'-deoxynebularine, 5-nitroindole, 2-aminopurinei, dP(purine analogue), dK(pyrimidine analogue), 3-nitropyrrole, 2-thio-dT, 4-thio-dT, biotin-dT, carboxy-dT, O$^4$-Me-dT, O$^4$-triazol dT, 2-OMe-propynyl-U, 5-Br-dU, 2'-dU, 5-F-dU, 5-I-dU, O$^4$-triazol dU and radiolabels (e.g. $^{125}$I, $^{131}$I, $^{35}$S, $^{14}$C, $^{32}$P, $^{33}$P, $^{3}$H). Said terms also encompass peptide nucleic acids (PNAs), a DNA analogue in which the backbone is a pseudopeptide consisting of N-(2-aminoethyl)-glycine units rather than a sugar. PNAs mimic the behaviour of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors. With "recombinant DNA-molecule" or "chimeric gene" is meant a hybrid DNA produced by joining pieces of DNA from different sources. With "heterologous nucleotide sequence" is intended a sequence that is not naturally occurring with the promoter sequence. While this nucleotide sequence is heterologous to the promoter sequence it may be homologous, or native, or heterologous, or foreign, to the plant host. "Sense strand" refers to the strand of a double-stranded DNA molecule that is homologous to a mRNA transcript thereof. The "anti-sense strand" contains an inverted sequence, which is complementary to that of the "sense strand".

A "coding sequence" or "open reading frame" or "ORF" is defined as a nucleotide sequence that can be transcribed into mRNA and/or translated into a polypeptide when placed under the control of appropriate regulatory sequences, i.e. when said coding sequence or ORF is present in an expressible format. Said coding sequence of ORF is bounded by a 5' translation start codon and a 3' translation stop codon. A coding sequence or ORF can include, but is not limited to RNA, mRNA, cDNA, recombinant nucleotide sequences, synthetically manufactured nucleotide sequences or genomic DNA. Said coding sequence or ORF can be interrupted by intervening nucleic acid sequences.

Genes and coding sequences essentially encoding the same protein but isolated from different sources can consist of substantially divergent nucleic acid sequences. Reciprocally, substantially divergent nucleic acid sequences can be designed to effect expression of essentially the same protein. Said nucleic acid sequences are the result of e.g. the existence of different alleles of a given gene, of the degeneracy of the genetic code or of differences in codon usage. Thus, as indicated in Table 2, amino acids such as methionine and tryptophan are encoded by a single codon whereas other amino acids such as arginine, leucine and seine can each be translated from up to six different codons. Differences in preferred codon usage are illustrated below for *Agrobacterium tumefaciens* (a bacterium), *A. thaliana, M sativa* (two dicotyledonous plants) and *Oryza sativa* (a monocotyledonous plant). These examples were extracted from. To give one example, the codon GGC (for glycine) is the most frequently used codon in *A. tumefaciens* (36.2%), is the second most frequently used codon in *O. sativa* but is used at much lower frequencies in *A. thaliana* and *M. sativa* (9% and 8.4%, respectively). Of the four possible codons encoding glycine (see Table 2), said GGC codon is most preferably used in *A. tumefaciens* and *O. sativa*. However, in *A. thaliana* this is the GGA (and GGU) codon whereas in *M. sativa* this is the GGU (and GGA) codon.

TABLE 2

Degeneracy of the genetic code.

| Amino Acid | Three-letter code | One-letter code | Possible codons | | | | | |
|---|---|---|---|---|---|---|---|---|
| Alanine | Ala | A | GCA | GCC | GCG | GCU | | |
| Arginine | Arg | R | AGA | AGG | CGA | CGC | CGG | CGU |
| Asparagine | Asn | N | AAC | AAU | | | | |
| Aspartic Acid | Asp | D | GAC | GAU | | | | |
| Cysteine | Cys | C | UGC | UGU | | | | |
| Glutamic Acid | Glu | E | GAA | GAG | | | | |
| Glutamine | Gln | Q | CAA | CAG | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Leucine | Leu | L | UUA | UUG | CUA | CUC | CUG | CUU |
| Lysine | Lys | K | AAA | AAG | | | | |
| Methionine | Met | M | AUG | | | | | |
| Phenylalanine | Phe | F | UUC | UUU | | | | |
| Proline | Pro | P | CCA | CCC | CCG | CCU | | |
| Serine | Ser | S | AGC | AGU | UCA | UCC | UCG | UCU |
| Threonine | Thr | T | ACA | ACC | ACG | ACU | | |
| Tryptophan | Trp | W | UGG | | | | | |
| Tyrosine | Tyr | Y | UAC | UAU | | | | |
| Valine | Val | V | GUA | GUC | GUG | GUU | | |
| Possible "STOP" codons | | | | | | | | |
| | | | UAA | UAG | UGA | | | |

"Hybridisation" is the process wherein substantially homologous complementary nucleotide sequences anneal to each other. The hybridisation process can occur entirely In solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process can also occur with one of the complementary nucleic acids immobilised to a matrix such as magnetic beads, Sepharose beads or any other resin. Tools in molecular biology relying on such a process include the isolation of poly (A+) mRNA. The hybridisation process can furthermore occur with one of the complementary nucleic acids immobilised to a solid support such as a nitro-cellulose or nylon membrane or immobilised by e.g. photolithography to e.g. a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. High stingency conditions for hybridization include high temperature and/or low salt concentration (salts include NaCl and $Na_3$-citrate) and/or the inclusion of formamide in the hybridisation buffer and/or lowering the concentration of compounds such as SDS (detergent) in the hybridisation buffer and/or exclusion of compounds such as dextran sulphate or polyethylene glycol (promoting molecular crowding) from the hybridisation buffer. Specific conditions for "specifically hybridizing" are for example: hybridising under stringent conditions such as a temperature of 60° C. followed by washes in 2×SSC, 0.1×SDS, and 1×SSC, 0.1×SDS. Conventional hybridisation conditions are described e.g. (Sambrook et. al. 1989) but the skilled craftsman will appreciate, that numerous different hybridisation conditions can be designed in function of the known or the expected homology and/or length of the nucleic acid sequence. Sufficiently low stringency hybridisation conditions are particularly preferred to isolate nucleic acids heterologous to the DNA sequences of the invention defined supra. Elements contributing to said heterology include allelism, degeneration of the genetic code and differences in preferred codon usage as discussed supra.

Clearly, the current invention embodies the use of the inventive DNA sequences encoding a DRE-binding factor DBF1, homologue, derivative and/or immunologically fragment thereof as defined higher in any method of hybridisation. The current invention furthermore also related to DNA sequences hybridising to said inventive DNA sequences.

DNA sequences as defined in the current invention can be interrupted by intervening sequences. With "intervening sequences" is meant any nucleic acid sequence which disrupts a coding sequence comprising said inventive DNA sequence or which disrupts the expressible format of a DNA sequence comprising said inventive DNA sequence. Removal of the intervening sequence restores said coding sequence or said expressible format. Examples of intervening sequences include introns, mobilizable DNA sequences such as transposons and DNA tags such as e.g. a T-DNA. With "mobilizable DNA sequence" is meant any DNA sequence that can be mobilised as the result of a recombination event.

To effect expression of a protein in a cell, tissue or organ, preferably of plant origin, either the protein may be introduced directly to said cell, such as by microinjection or ballistic means or alternatively, an isolated nucleic acid molecule encoding said protein may be introduced into said cell, tissue or organ in an expressible format.

Preferably, the DNA sequence of the invention comprises a coding sequence or open reading frame (ORF) encoding a DRE-binding factor DBF1 or a homologue or derivative thereof or an immunologically active thereof as defined supra. The preferred protein of the invention comprises the amino acid sequence of said AP2/EREBP domain transcription factor.

With "vector" or "vector sequence" is meant a DNA sequence, which can be introduced in an organism by transformation and can be stably maintained in said organism. Vector maintenance is possible in e.g. cultures of *Escherichia coli, A. tumefaciens, Saccharomyces cerevisiae* or *Schizosaccharomyces pombe*. Other vectors such as phagemids and cosmid vectors can be maintained and multiplied in bacteria and/or viruses. Vector sequences generally comprise a set of unique sites recognised by restriction enzymes, the multiple cloning site (MCS), wherein one or more non-vector sequence(s) can be inserted.

With "non-vector sequence" is accordingly meant a DNA sequence which is integrated in one or more of the sites of the MCS comprised within a vector.

"Expression vectors" form a subset of vectors which, by virtue of comprising the appropriate regulatory sequences enabling the creation of an expressible format for the inserted non-vector sequence(s), thus allowing expression of the protein encoded by said non-vector sequence(s). Expression vectors are known in the art enabling protein expression in organisms including bacteria (e.g. *E. coli*), fungi (e.g. *S. cerevisiae, S. pombe, Pichia pastoris*), insect cells (e.g. baculoviral expression vectors), animal cells (e.g. COS or CHO cells) and plant cells (e.g. potato virus X-based expression vectors, see e.g. Vance et al. 1998—WO9844097).

The current invention clearly includes any vector or expression vector comprising a non-vector DNA sequence comprising the promoter sequence according to the present invention or a non-vector sequence encoding a DRE-binding factor DBF1, homologue, derivative and/or immunologically active fragment thereof as defined supra.

As an alternative to expression vector-mediated protein production in biological systems, chemical protein synthesis can be applied. Synthetic peptides can be manufactured in solution phase or in solid phase. Solid phase peptide synthesis (Merrifield 1963) is, however, the most common way and involves the sequential addition of amino acids to create a linear peptide chain. Solid phase peptide synthesis includes cycles consisting of three steps: (i) immobilisation of the carboxy-terminal amino acid of the growing peptide chain to a solid support for resin; (ii) chain assembly, a process consisting of activation, coupling and deprotection of the amino acid to be added to the growing peptide chain; and (iii) cleavage involving removal of the completed peptide chain from the resin and removal of the protecting groups from the amino acid side chains. Common approaches in solid phase peptide synthesis include Fmoc/tBu (9-fluorenylmethyloxycarbonyl/t-butyl) and Boc (t-butyloxycarbonyl) as the amino-terminal protecting groups of amino acids. Amino acid side chain protecting groups include methyl (Me), formyl (CHO), ethyl (Et), acetyl (Ac), t-butyl (t-Bu), anisyl, benzyl (Bzl), trifluoroacetyl (Tfa), N-hydroxysuccinimide (ONSu, OSu), benzoyl (Bz), 4-methylbenzyl (Meb), thioanizyl, thiocresyl, benzyloxymethyl (Bom), 4-nitrophenyl (ONp), benzyloxycarbonyl (Z), 2-nitrobenzoyl (NBz), 2-nitrophenylsulphenyl (Nps), 4-toluenesulphonyl (Tosyl, Tos), pentafluorophenyl (Pfp), diphenylmethyl (Dpm), 2-chlorobenzyloxycarbonyl (Cl-Z), 2,4,5-trichlorophenyl, 2-bromobenzyloxycarbonyl (Br-Z), tripheylmethyl (Trityl, Trt), and 2,5,7,8-pentamethyl-chroman-6-sulphonyl (Pmc). During chain assembly, Fmoc or Boc are, removed resulting in an activated amino-terminus of the amino acid residue bound to the growing chain. The carboxy-terminus of the incoming amino acid is activated by conversion into a highly reactive ester, e.g. by HBTU. With current technologies (e.g. PerSeptive Biosystems 9050 synthesizer, Applied Biosystems Model 431 A Peptide Synthesizer), linear peptides of up to 50 residues can be manufactured. A number of guidelines is available to produce peptides that are suitable for use in biological systems including (i) limiting the use of difficult amino acids such as cys, met, trp (easily oxidised and/or degraded during peptide synthesis) or arg; (ii) minimize hydrophobic amino acids (can impair peptide solubility); and (iii) prevent an amino-terminal glutamic acid (can cyclize to pyroglutamate).

By "expressible format" is meant that the isolated nucleic acid molecule is in a form suitable for being transcribed into mRNA and/or translated to produce a protein, either constitutively or following induction by an intracellular or extracellular signal, such as an environmental stimulus or stress (mitogens, anoxia, hypoxia, temperature, salt, light, dehydration, etc) or a chemicals compound such as IPTG (isopropyl-β-D-thiogalactopyranoside) or such as an antibiotic (tetracycline, ampicillin, rifampicin, kanamycin), hormone (e.g. gibberellin, auxin, cytokinin, glucocorticoid, brassinosteroid, ethylene, abscisic acid etc), hormone analogue (iodoacetic acid (IAA), 2,4-D, etc), metal (zinc, copper, iron, etc), or dexamethasone, amongst others. As will be known to those skilled in the art, expression of a functional protein may also require one or more post-translational modifications, such as glycosylation, phosphorylation, dephosphorylation, or one or more protein-protein interactions, amongst others. All such processes are included within the scope of the term "expressible format".

Preferably, expression of a protein in a specific cell, tissue, or organ, preferably of plant origin, is effected by introducing and expressing an isolated nucleic acid molecule encoding said protein, such as a cDNA molecule, genomic gene, synthetic oligonucleotide molecule, mRNA molecule or open reading frame, to said cell, tissue or organ, wherein said nucleic acid molecule is placed operably in connection with suitable regulatory sequences including a promoter, preferably a plant-expressible promoter, and a terminator sequence.

"Regulatory sequence" refers to control DNA sequences, which are necessary to affect the expression of coding sequences to which they are ligated. The nature of such control sequences differs depending upon the host organism. In prokaryotes, control sequences generally include promoters, ribosomal binding sites, and terminators. In eukaryotes generally control sequences include promoters, terminators and enhancers or silencers. The term "control sequence" is intended to include, at a minimum, all components the presence of which are necessary for expression, and may also include additional advantageous components and which determines when, how much and where a specific gene is expressed.

Reference herein to a "promoter" is to be taken in its broadest context and includes the transcriptional regulatory sequences derived from a classical eukaryotic genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner.

The term "promoter" also includes the transcriptional regulatory sequences of a classical prokaryotic gene, in which case it may include a −35 box sequence and/or a −10 box transcriptional regulatory sequences.

The term "promoter" is also used to describe a synthetic or fusion molecule or derivative, which confers, activates or enhances expression of a nucleic acid molecule in a cell, tissue or organ.

Promoters may contain additional copies of one or more specific regulatory elements, to further enhance expression and/or to alter the spatial expression and/or temporal expression of a nucleic acid molecule to which it is operably connected. Such regulatory elements may be placed adjacent to a heterologous promoter sequence to drive expression of a nucleic acid molecule in response to e.g. copper, glucocorticoids, dexamethasone, tetracycline, gibberellin, cAMP, abscisic acid, auxin, wounding, ethylene, jasmonate or salicylic acid or to confer expression of a nucleic acid molecule to specific cells, tissues or organs such as meristems, leaves, roots, embryo, flowers, seeds or fruits.

In the context of the present invention, the promoter preferably is a plant-expressible promoter sequence. Promoters, however, that also function or solely function in non-plant cells such as bacteria, yeast cells, insect cells and animal cells are not excluded from the invention. By "plant-expressible" is meant that the promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ.

The terms "plant-operable" and "operable in a plant" when used herein, in respect of a promoter sequence, shall be taken to be equivalent to a plant-expressible promoter sequence.

In the present context, a "regulated promoter" or "regulatable promoter sequence" is a promoter that is capable of conferring expression on a structural gene in a particular cell, tissue, or organ or group of cells, tissues or organs of a plant, optionally under specific conditions, however does generally not confer expression throughout the plant under all conditions. Accordingly, a regulatable promoter sequence may be a promoter sequence that confers expression on a gene to which it is operably connected in a particular location within the plant or alternatively, throughout the plant under a specific set of conditions, such as following induction of gene expression by a chemical compound or other elicitor.

Preferably, the regulatable promoter used in the performance of the present invention confers expression in a specific location within the plant, either constitutively or following induction, however not in the whole plant under any circumstances. Included within the scope of such promoters are cell-specific promoter sequences, tissue-specific promoter sequences, organ-specific promoter sequences, cell cycle specific gene promoter sequences, inducible promoter sequences and constitutive promoter sequences that have been modified to confer expression in a particular part of the plant at any one time, such as by integration of said constitutive promoter within a transposable genetic element (Ac, Ds, Spm, En, or other transposon). Those skilled in the art will be aware that an "inducible promoter" is a promoter the transcriptional activity of which is increased or induced in response to a developmental, chemical, environmental, or physical stimulus. Similarly, the skilled craftsman will understand that a "constitutive promoter" is a promoter that is transcriptionally active throughout most, but not necessarily all parts of an organism, preferably a plant, during most, but not necessarily all phases of its growth and development. Contrarely the term "ubiquitous promoter" is taken to indicate a promoter that is transcriptionally active throughout most, but not necessarily all parts of an organism, preferably a plant.

Generally by "weak promoter" is intended a promoter that drives expression of a coding sequence at a low level. By "low level" is intended at levels of about 1/10,000 transcripts to about 1/100,000 transcripts, to about 1/500,0000 transcripts. Conversely, a "strong promoter" drives expression of a coding sequence at high level, or at about 1/10 transcripts to about 1/100 transcripts to about 1/1,000 transcripts.

The term "cell-specific" shall be taken to indicate that expression is predominantly in a particular cell or cell-type, preferably of plant origin, albeit not necessarily exclusively in said cell or cell-type.

Similarly, the term "tissue-specific" shall be taken to indicate that expression is predominantly in a particular tissue or tissue-type, preferably of plant origin, albeit not necessarily exclusively in said tissue or tissue-type.

Similarly, the term "organ-specific" shall be taken to indicate that expression is predominantly in a particular organ, preferably of plant origin, albeit not necessarily exclusively in said organ. "Root-specific" means that the promoter is expressed in the root only and not in other tissues of the plant.

By "root-preferred" it is intended that expression of the heterologous nucleotide sequence is most abundant root, but could also have low expression levels elsewhere in the plant. While some level of expression of the heterologous nucleotide sequence occurs in other plant tissue types, expression occurs most abundantly in the root including primary, lateral and adventitious roots.

By "root" is intended any part of the root structure, comprising the root cap, apical meristem, protoderm, ground meristem, procambium, endodermis, cortex, vascular cortex, epidermis, and the like.

Those skilled in the art will readily be capable of selecting appropriate promoter sequences for use in regulating appropriate expression of the DRE-binding factor DBF1 described supra from publicly-available or readily-available sources, without undue experimentation.

Placing a nucleic acid molecule under the regulatory control of a promoter sequence, or in operable connection with a promoter sequence means positioning said nucleic acid molecule such that expression is controlled by the promoter sequence. A promoter is usually, but not necessarily, positioned upstream, or at the 5'end, and within 2 kb of the start site of transcription, of the nucleic acid molecule which it regulates. In the construction of heterologous promoter/structural gene combinations it is generally preferred to position the promoter at a distance from the gene transcription start site that is approximately the same as the distance between that promoter and the gene it controls in its natural setting (i.e., the gene from which the promoter is derived). As is known in the art, some variation in this distance can be accommodated without loss of promoter function. Similarly, the preferred positioning of a regulatory sequence element with respect to a heterologous gene to be placed under its control is defined by the positioning of the element in its natural setting (i.e., the gene from which it is derived).

Again, as is known in the art, some variation in this distance can also occur. "Expression" means the production of a protein or nucleotide sequence in the cell itself or in a cell-free system. It includes transcription into an RNA product, post-transcriptional modification and/or translation to a protein product or polypeptide from a DNA encoding that product, as well as possible post-translational modifications.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

Examples of promoters suitable for use in gene constructs of the present invention include those listed in Table 3, amongst others. The promoters listed in Table 3 are provided for the purposes of exemplification only and the present invention is not to be limited by the list provided therein. Those skilled in the art will readily be in a position to provide additional promoters that are useful in performing the present invention.

In the case of constitutive promoters or promoters that induce expression throughout the entire plant, it is preferred that such sequences are modified by the addition of nucleotide sequences derived from one or more of the tissue-specific promoters listed in Table 3, or alternatively, nucleotide sequences derived from one or more of the above-mentioned tissue-specific inducible promoters, to confer tissue-specificity thereon. For example, the CaMV 35S prompter may be modified by the addition of maize Adh1 promoter sequence, to confer anaerobically-regulated root-specific expression thereon, as described previously (Ellis et al. 1987). Another example describes conferring root specific or root abundant gene expression by fusing the CaMV35S promoter to elements of the maize glycine-rich protein GRP3 gene (Feix and Wulff 2000-WO0015662). Such modifications can be achieved by routine experimentation by those skilled in the art.

The term "terminator" refers to a DNA sequence at the end of a transcriptional unit which signal termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants.

Examples of terminators particularly suitable for use in the gene constructs of the present invention include the *Agrobacterium tumefaciens* nopaline synthase (NOS) gene terminator, the *Agrobacterium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3'Bt2), the *Zea mays* zein gene terminator sequence, the rbcs-1A gene terminator, and the rbcs-3A gene terminator sequences, amongst others.

Those skilled in the art will be aware of additional promoter sequences and terminator sequences which may be suitable for use in performing the invention. Such sequences may readily be used without any undue experimentation.

In the context of the current invention, "ectopic expression" or "ectopic overexpression" of a gene or a protein are conferring to expression patterns and/or expression levels of said gene or protein normally not occurring under natural conditions. Ectopic expression can be achieved in a number of ways including operably linking of a coding sequence encoding said protein to an isolated homologous or heterologous promoter in order to create a chimeric gene and/or operably linking said coding sequence to its own isolated promoter (i.e. the unisolated promoter naturally driving expression of said protein) in order to create a recombinant gene duplication or gene multiplication effect. With "ectopic co-expression" is meant the ectopic expression or ectopic overexpression of two or more genes or proteins. The same or, more preferably, different promoters are used to confer expression of said genes or proteins.

TABLE 3

Exemplary plant-expressible promoters for use in the performance of the present invention

I: CELL-SPECIFIC, TISSUE-SPECIFIC, AND ORGAN-SPECIFIC PROMOTERS

| GENE SOURCE | EXPRESSION PATTERN | REFERENCE |
|---|---|---|
| α-amylase (Amy32b) | aleurone | Lanahan et al, Plant Cell 4: 203-211, 1992; Skriver et al, Proc Natl Acad Sci USA 88: 7266-7270, 1991 |
| cathepsin β-like gene | aleurone | Cejudo et al, Plant Mol Biol 20: 849-856, 1992 |
| *Agrobacterium rhizogenes* rolB | cambium | Nilsson et al, Physiol Plant 100: 456-462, 1997 |
| AtPRP4 | flowers | |
| chalcone synthase (chsA) | flowers | Van der Meer et al, Plant Mol Biol 15: 95-109, 1990 |
| LAT52 | anther | Twell et al, Mol Gen Genet 217: 240-245, 1989 |
| apetala-3 | flowers | |
| chitinase | fruit (berries, grapes, etc) | Thomas et al. CSIRO Plant Industry, Urrbrae, South Australia, Australia; |
| rbcs-3A | green tissue (eg leaf) | Lam et al, Plant Cell 2: 857-866, 1990; Tucker et al., Plant Physiol 113: 1303-1308, 1992 |
| leaf-specific genes | leaf | Baszczynski et al, Nucl Acid Res 16: 4732, 1988 |
| AtPRP4 | leaf | |
| chlorella virus adenine methyltransferase gene promoter | leaf | Mitra and Higgins, Plant Mol Biol 26: 85-93, 1994 |
| aldP gene promoter | leaf | Kagaya et al, Mol Gen Genet 248: 668-674, |

TABLE 3-continued

Exemplary plant-expressible promoters for use in the performance of the present invention

| | | |
|---|---|---|
| from rice | | 1995 |
| rbcs promoter from rice or tomato | leaf | Kyozuka et al, Plant Physiol 102: 991-1000, 1993 |
| Pinus cab-6 | leaf | Yamamoto et al, Plant Cell Physiol 35: 773-778, 1994 |
| rubisco promoter | leaf | |
| cab (chlorophyll a/b/binding protein | leaf | |
| pea Blec4 gene | vegetative and floral epidermal tissues | Mandaci and Dobres, Plant Mol Biol 34: 961-965 |
| SAM22 | senescent leaf | Crowell et al, Plant Mol Biol 18: 459-466, 1992 |
| ltp gene (lipid transfer gene) | | Fleming et al, Plant J 2: 855-862, 1992 |
| *R. japonicum* nif gene | nodule | U.S. Pat. No. 4 803165 |
| *B. japonicum* nifH gene | nodule | U.S. Pat. No. 5008194 |
| GmENOD40 | nodule | Yang et al, Plant J 3: 573-585, 1993 |
| PEP carboxylase (PEPC) | nodule | Pathirana et al, Plant Mol Biol 20: 437-450, 1992 |
| leghaemoglobin (Lb) | nodule | Gordon et al, J Exp Bot 44: 1453-1465, 1993 |
| *Tungro bacilliform* virus gene | phloem | Bhattacharyya-Pakrasi et al, Plant J 4: 71-79, 1992 |
| pollen-specific genes | pollen; microspore | Albani et al, Plant Mol Biol 15: 605, 1990; Albani et al, Plant Mol Biol 16: 501, 1991 |
| Zm13 | pollen | Guerrero et al, Mol Gen Genet 224: 161-168, 1993 |
| apg gene | microspore | Twell et al, Sex Plant Reprod 6: 217-224, 1993 |
| maize pollen-specific gene | pollen | Hamilton et al, Plant Mol Biol 18: 211-218, 1992 |
| sunflower pollen-expressed gene | pollen | Baltz et al, Plant J 2: 713-721, 1992 |
| *B. napus* pollen-specific gene | pollen; anther; tapetum | Arnoldo et al, J Cell Biochem, Abstract No. Y101, 204, 1992 |
| root-expressible genes | roots | Tingey et al, EMBO J 6: 1, 1987 |
| tobacco auxin-inducible gene | root tip | Van der Zaal et al, Plant Mol Biol 16: 983, 1991 |
| β-tubulin | root | Oppenheimer et al, Gene 63: 87, 1988 |
| tobacco root-specific genes | root | Conkling et al, Plant Physiol 93: 1203, 1990 |
| *B. napus* G1-3b gene | root | U.S. Pat. No. 5401836 |
| SbPRP1 | roots | Suzuki et al, Plant Mol Biol 21: 109-119, 1993 |
| AtPRP1; AtPRP3 | roots; root hairs | |
| RD2 gene | root cortex | |
| TobRB7 gene | root vasculature | |
| AtPRP4 | leaves; flowers; lateral root primordia | |
| seed-specific genes | seed | Simon et al, Plant Mol Biol 5: 191, 1985; Scofield et al, J Biol Chem 262: 12202, 1987; Baszczynski et al, Plant Mol Biol 14: 633, 1990 |
| Brazil Nut albumin | seed | Pearson et al, Plant Mol Biol 18: 235-245, 1992 |
| legumin | seed | Ellis et al, Plant Mol Biol 10: 203-214, 1988 |
| glutelin (rice) | seed | Takaiwa et al, Mol Gen Genet 208: 15-22, 1986; Takaiwa et al, FEBS Lett 221: 43-47, 1987 |
| zein | seed | Matzke et al, Plant Mol Biol 14: 323-32 1990 |
| napA | seed | Stalberg et al, Planta 199: 515-519, 1996 |
| wheat LMW and HMW glutenin-1 | endosperm | Mol Gen Genet 216: 81-90, 1989; Nucl Acids Res 17: 461-462, 1989 |
| wheat SPA | seed | Albani et al, Plant Cell 9: 171-184, 1997 |
| cZ19B1, maize 19 kDa zein | seed | WO0011177 |
| milps, maize myoinositol-1-Pi synthase | seed | WO0011177 |
| wheat α,β,γ-gliadins | endosperm | EMBO J 3: 1409-1415, 1984 |
| barley ltr1 promoter | endosperm | |
| barley B1, C, D, hordein | endosperm | Theor Appl Gen 98: 1253-1262, 1999; Plant J 4: 343-355, 1993; Mol Gen Genet 250: 750-60, 1996 |
| barley DOF | endosperm | Mena et al, Plant J 116: 53-62, 1998 |
| blz2 | endosperm | EP99106056.7 |
| synthetic promoter | endosperm | Vicente-Carbajosa et al, Plant J 13: 629-640, 1998 |

TABLE 3-continued

Exemplary plant-expressible promoters for use in the performance of the present invention

| | | |
|---|---|---|
| rice prolamin NRP33 | endosperm | Wu et al, Plant Cell Physiol 39: 885-889, 1998 |
| rice α-globulin Glb-1 | endosperm | Wu et al, Plant Cell Physiol 39: 885-889, 1998 |
| maize END genes | endosperm | WO0012733 |
| barley END1 | endosperm | WO9808961 |
| barley NUC1 | nucellus | WO9808961 |
| rice OSH1 | embryo | Sato et al, Proc Natl Acad Sci USA 93: 8117-8122, 1996 |
| rice α-globulin REB/OHP-1 | endosperm | Nakase et al, Plant Mol Biol 33: 513-522, 1997 |
| rice ADP-glucose PP | endosperm | Trans Res 6: 157-168, 1997 |
| maize ESR gene family | endosperm | Plant J 12: 235-246, 1997 |
| sorgum γ-kafirin | endosperm | Plant Mol Biol 32: 1029-1035, 1996 |
| KNOX | embryo | Postma-Haarsma et al, Plant Mol Biol 39: 257-271, 1999 |
| rice oleosin | embryo and aleuron | Wu et al, J Biochem 123: 386, 1998 |
| sunflower oleosin | seed (embryo and dry seed) | Cummins et al, Plant Mol Biol 19: 873-876, 1992 |
| LEAFY | shoot meristem | Weigel et al, Cell 69: 843-859, 1992 |
| *Arabidopsis thaliana* knat1 | shoot meristem | Accession number AJ131822 |
| *Malus domestica* kn1 | shoot meristem | Accession number Z71981 |
| CLAVATA1 | shoot meristem | Accession number AF049870 |
| stigma-specific genes | stigma | Nasrallah et al, Proc Natl Acad Sci USA 85: 5551, 1988; Trick et al, Plant Mol Biol 15: 203, 1990 |
| class I patatin gene | tuber | Liu et al, Plant Mol Biol 153: 386-395, 1991 |
| PCNA rice | meristem | Kosugi et al, Nucl Acids Res 19: 1571-1576, 1991; Kosugi and Ohashi, Plant Cell 9: 1607-1619, 1997 |
| Pea TubA1 tubulin | Dividing cells | Stotz and Long, Plant Mol Biol 41: 601-614, 1999 |
| *Arabidopsis* cdc2a | cycling cells | Chung and Parish, FEBS Lett 362: 215-219, 1995 |
| *Arabidopsis* Rop1A | Anthers; mature pollen + pollen tubes | Li et al, Plant Physiol 118: 407-417, 1998 |
| *Arabidopsis* AtDMC1 | Meiosis-associated | Klimyuk and Jones, Plant J 11: 1-14, 1997 |
| Pea PS-IAA4/5 and PS-IAA6 | Auxin-inducible | Wong et al, Plant J 9: 587-599, 1996 |
| Pea farnesyltransferase | Meristematic tissues; phloem near growing tissues; light- and sugar-repressed | Zhou et al, Plant J 12: 921-930, 1997 |
| Tobacco (*N. sylvestris*) cyclin B1; 1 | Dividing cells/ meristematic tissue | Trehin et al, Plant Mol. Biol. 35: 667-672, 1997 |
| *Catharanthus roseus* Mitotic cyclins CYS (A-type) and CYM (B-type) | Dividing cells/ meristematic tissue | Ito et al, Plant J 11: 983-992, 1997 |
| *Arabidopsis* cyc1At (=cyc B1; 1) and cyc3aAt (A-type) | Dividing cells/ meristematic tissue | Shaul et al, Proc Natl Acad Sci USA 93: 4868-4872, 1996 |
| *Arabidopsis* tef1 promoter box | Dividing cells/ meristematic tissue | Regad et al, Mol Gen Genet 248: 703-711, 1995 |
| *Catharanthus roseus* cyc07 | Dividing cells/ meristematic tissue | Ito et al, Plant Mol Biol 24: 863-878, 1994 |

II: EXEMPLARY CONSTITUTIVE PROMOTERS

| GENE SOURCE | EXPRESSION PATTERN | REFERENCE |
|---|---|---|
| Actin | constitutive | McElroy et al, Plant Cell 2: 163-171, 1990 |
| CAMV 35S | constitutive | Odell et al, Nature 313: 810-812, 1985 |
| CaMV 19S | constitutive | Nilsson et al, Physiol Plant 100: 456-462, 1997 |
| GOS2 | constitutive | de Pater et al, Plant J 2: 837-844, 1992 |
| ubiquitin | constitutive | Christensen et al, Plant Mol Biol 18: 675-689, 1992 |
| rice cyclophilin | constitutive | Buchholz et al, Plant Mol Biol 25: 837-843, 1994 |
| maize histone H3 | constitutive | Lepetit et al, Mol Gen Genet 231: 276-285, 1992 |

TABLE 3-continued

Exemplary plant-expressible promoters for use in the performance of the present invention

| | | |
|---|---|---|
| alfalfa histone H3 | constitutive | Wu et al, Nucleic Acids Res 17: 3057-3063, 1989; Wu et al, Plant Mol Biol 11: 641-649, 1988 |
| actin 2 | constitutive | An et al, Plant J 10: 107-121, 1996 |

III: EXEMPLARY STRESS-INDUCIBLE PROMOTERS

| NAME | STRESS | REFERENCE |
|---|---|---|
| P5CS (delta(1)-pyrroline-5-carboxylate syntase) | salt, water | Zhang et al, Plant Sci 129: 81-89, 1997 |
| cor15a | cold | Hajela et al, Plant Physiol 93: 1246-1252, 1990 |
| cor15b | cold | Wlihelm et al, Plant Mol Biol 23: 1073-1077, 1993 |
| cor15a (−305 to +78 nt) | cold, drought | Baker et al, Plant Mol Biol 24: 01-713, 1994 |
| rd29 | salt, drought, cold | Kasuga et al, Nature Biotechnol 18: 287-291, 1999 |
| heat shock proteins, including artificial promoters containing the heat shock element (HSE) | heat | Barros et al, Plant Mol Biol 19 665-75, 1992. Marrs et al, Dev Genet14: 27-41, 1993. Schoffl et al, Mol Gen Genet 217: 246-53, 1989. |
| smHSP (small heat shock proteins) | heat | Waters et al, J Exp Bot 47: 325-338, 1996 |
| wcs120 | cold | Ouellete et al, FEBS Lett 423: 324-328, 1998 |
| ci7 | cold | Kirch et al, Plant Mol Biol 33: 897-909, 1997 |
| Adh | cold, drought, hypoxia | Dolferus et al, Plant Physiol 105: 1075-87, 1994 |
| pwsi18 | salt and drought | Joshee et al, Plant Cell Physiol 39: 64-72, 1998 |
| ci21A | cold | Schneider et al, Plant Physiol 113: 335-45, 1997 |
| Trg-31 | drought | Chaudhary et al, Plant Mol Biol 30: 1247-57, 1996 |
| osmotin | osmotic | Raghothama et al, Plant Mol Biol 23: 1117-28, 1993 |
| lapA | wounding, enviromental | WO99/03977 University of California/INRA |

IV: EXEMPLARY PATHOGEN-INDUCIBLE PROMOTERS

| NAME | PATHOGEN | REFERENCE |
|---|---|---|
| RB7 | Root-knot nematodes (*Meloidogyne* spp.) | U.S. Pat. No. 5760386 - North Carolina State University; Opperman et al, Science 263: 221-23, 1994 |
| PR-1, 2, 3, 4, 5, 8, 11 | fungal, viral, bacterial | Ward et al, Plant Cell 3: 1085-1094, 1991; Reiss et al 1996; Lebel et al, Plant J 16: 223-233, 1998; Melchers et al, Plant J 5: 469-480, 1994; Lawton et al, Plant Mol Biol, 19: 735-743, 1992 |
| HMG2 | nematodes | WO9503690 - Virginia Tech Intellectual Properties Inc. |
| Abi3 | Cyst nematodes (*Heterodera* spp.) | unpublished |
| ARM1 | nematodes | Barthels et al, Plant Cell 9: 2119-2134, 1997 WO 98/31822 - Plant Genetic Systems |
| Att0728 | nematodes | Barthels et al, Plant Cell 9: 2119-2134, 1997 PCT/EP98/07761 |
| Att1712 | nematodes | Barthels et al, Plant Cell 9, 2119-2134, 1997 PCT/EP98/07761 |
| Gst1 | Different types of pathogens | Strittmatter et al, Mol Plant-Microbe Interact 9: 68-73, 1996 |
| LEMMI | nematodes | WO 92/21757 - Plant Genetic Systems |
| CLE | geminivirus | PCT/EP99/03445 - CINESTAV |
| PDF1.2 | Fungal including *Alternaria brassicicola* and *Botrytis cinerea* | Manners et al, Plant Mol Biol, 38: 1071-1080, 1998 |
| Thi2.1 | Fungal - *Fusarium oxysporum f* sp. matthiolae | Vignutelli et al, Plant J 14: 285-295, 1998 |
| DB#226 | nematodes | Bird and Wilson, Mol Plant-Microbe Interact 7: 419-442, 1994 WO 95.322888 |

TABLE 3-continued

Exemplary plant-expressible promoters for use in the performance of the present invention

| | | |
|---|---|---|
| DB#280 | nematodes | Bird and Wilson, Mol Plant-Microbe Interact 7: 419-442, 1994<br>WO 95.322888 |
| Cat2 | nematodes | Niebel et al, Mol Plant-Microbe Interact 8: 371-378, 1995 |
| ☐Tub | nematodes | Aristizabal et al (1996), 8th International Congress on Plant-Microbe Interaction, Knoxville US B-29 |
| sHSP | nematodes | Fenoll et al (1997) In: Cellular and molecular aspects of plant-nematode interactions. Kluwer Academic, C. Fenoll, F. M. W. Grundler and S. A. Ohl (Eds.), |
| Tsw12 | nematodes | Fenoll et al (1997) In: Cellular and molecular aspects of plant-nematode interactions. Kluwer Academic, C. Fenoll, F. M. W. Grundler and S. A. Ohl (Eds.) |
| Hs1(pro1) | nematodes | WO 98/122335 - Jung |
| nsLTP | viral, fungal, bacterial | Molina and Garcia-Olmedo FEBS Lett, 316: 119-122, 1993 |
| RIP | viral, fungal | Turner et al, Proc Natl Acad Sci USA 94: 3866-3871, 1997 |

Preferably, the promoter sequence used in the context of the present invention is operably linked to a coding sequence or open reading frame (ORF) encoding a DRE-binding factor DBF1 or a homologue, derivative and/or an immunologically active fragment thereof as defined supra.

"Dominant negative version or variant" refers to a mutant protein, which interferes with the activity of the corresponding wild-type protein.

"Downregulation of expression" as used herein means lowering levels of gene expression and/or levels of active gene product and/or levels of gene product activity. Decreases in expression may be accomplished by e.g. the addition of coding sequences or parts thereof in a sense orientation (if resulting in co-suppression) or in an antisense orientation relative to a promoter sequence and furthermore by e.g. insertion mutagenesis (e.g. T-DNA, insertion or transposon insertion) or by gene silencing Strategies as described by e.g. Angell and Baulcombe 1998 (WO9836083), Lowe et al. 1989 (WO9985083), Lederer et al 1999 (WO9915682) or Wang et al. 1999 (WO9953050). Genetic constructs aimed at silencing gene expression may have the nucleotide sequence of said gene (or one or more parts thereof) contained therein in a sense and/or antisense orientation relative to the promoter sequence. Another method to downregulate gene expression comprises the use of ribozymes, e.g. as described in Atkins et al. 1994 (WO9400012), Lenee et al. 1995 (WO9503404), Lutziger et al. 2000 (WO0000619), Prinsen et al. 1997 (WO9713865) and Scott et al. 1997 (WO9738116).

Modulating, including lowering, the level of active gene products or of gene product activity can be achieved by administering or exposing cells, tissues, organs or organisms to said gene product, a homologue, analogue, derivative and/or immunologically active fragment thereof. Immunomodulation is another example of a technique capable of downregulation levels of active gene product and/or of gene product activity and comprises administration of or exposing to or expressing antibodies to said gene product to or in cells, tissues, organs or organisms wherein levels of said gene product and/or gene product activity are to be modulated. Such antibodies comprise "plantibodies", single chain antibodies, IgG antibodies and heavy chain camel antibodies as well as fragments thereof.

Modulating, including lowering, the level of active gene products or of gene product activity can furthermore be achieved by administering or exposing cells, tissues, organs or organisms to an inhibitor or activator of said gene product or the activity thereof. Such inhibitors or activators include proteins (comprising e.g. proteinases and kinases) and chemical compounds identified according to the current invention as described supra.

In the context of the invention the term "agonist" refers to a substance that can be either a protagonist or an antagonist, i.e. can have either positive or negative effects, can be an enhancer or an inhibitor or a modulator as well.

By "cell fate and/or plant development and/or plant morphology and/or biochemistry and/or physiology" is meant that one or more developmental and/or morphological and/or biochemical and/or physiological characteristics of a plant is altered by the performance of one or more steps pertaining to the invention described herein.

"Cell fate" refers to the cell-type or cellular characteristics of a particular cell that are produced during plant development or a cellular process therefor, "Plant development" or the term "plant developmental characteristic" or similar term shall, when used herein, be taken to mean any cellular process of a plant that is involved in determining the developmental fate of a plant cell, in particular the specific tissue or organ type into which a progenitor cell will develop. Cellular processes relevant to plant development will be known to those skilled in the art. Such processes include, for example, morphogenesis, photomorphogenesis, shoot development, root development, vegetative development, reproductive development, stem elongation, flowering, and regulatory mechanisms involved in determining cell fate, in particular a process or regulatory process involving the cell cycle.

"Plant morphology" or the term "plant morphological characteristic" or similar term will, when used herein, be understood by those skilled in the art to refer to the external appearance of a plant, including any one or more structural features or combination of structural features thereof. Such structural features include the shape, size, number, position, colour, texture, arrangement, and patternation of any cell, tissue or organ or groups of cells, tissues or organs of a plant, including the root, stem, leaf, shoot, petiole, trichome, flower, petal, stigma, style, stamen, pollen, ovule, seed, embryo, endosperm, seed coat, aleurone, fibre, fruit, cambium, wood, heartwood, parenchyma, aerenchyma, sieve element, phloem or vascular tissue, amongst others.

"Plant biochemistry" or the term "plant biochemical characteristic" or similar term will, when used herein, be understood by those skilled in the art to refer to the metabolic and catalytic processes of a plant, including primary and secondary metabolism and the products thereof, including any small molecules, macromolecules or chemical compounds, such as but not limited to starches, sugars, proteins, peptides, enzymes, hormones, growth factors, nucleic acid molecules, celluloses, hemicelluloses, calloses, lectins, fibres, pigments such as anthocyanins, vitamins, minerals, micronutrients, or macronutrients, that are produced by plants.

"Plant physiology" or the term "plant physiological characteristic" or similar term will, when used herein, be understood to refer to the functional processes of a plant, including developmental processes such as growth, expansion and differentiation, sexual development, sexual reproduction, seed set, seed development, grain filling, asexual reproduction, cell division, dormancy, germination, light adaptation, photosynthesis, leaf expansion, fiber production, secondary growth or wood production, amongst others; responses of a plant to externally-applied factors such as metals, chemicals, hormones, growth factors, environment and environmental stress factors (eg. anoxia, hypoxia, high temperature, low temperature, dehydration, light, daylength, flooding, salt, heavy metals, amongst others), including adaptive responses of plants to said externally-applied factors.

"Environmental stress" is a circumstance caused by elements present in the environment which may include but are not limited to drought, salt, dehydration, heat, cold, freezing, water logging, wounding, mechanical stress, oxidative stress, ozone, high light heavy metals, nutrient deprivation, toxic chemicals, pathogen (including viruses, bacteria, fungi, insects and nematodes) and combinations of these.

The term "environmental stress" has been defined in different ways in the prior art and largely overlaps with the term "osmotic stress". (Holmberg & Bülow, 1998, Trends plant sci. 3, 61-66) for instance define different environmental stress factors which result in abiotic stress. Salinity, drought, heat, chilling and freezing are all described as examples of conditions which induce osmotic stress. The term "environmental stress" as used in the present invention refers to any adverse effect on metabolism, growth or viability of the cell, tissue, seed, organ or whole plant which is produced by an non-living or non-biological environmental stressor. More particularly, it also encompasses environmental factors such as water stress (flooding, water logging, drought, dehydration), anaerobic (low level of oxygen, $CO_2$ etc.), aerobic stress, osmotic stress, salt stress, temperature stress (hot/heat, cold, freezing, frost) or nutrients deprivation, pollutants stress (heavy metals, toxic chemicals), ozone, high light, pathogen (including viruses, bacteria, fungi, insects and nematodes) and combinations of these.

The term "anaerobic stress" means any reduction in oxygen levels sufficient to produce a stress as hereinbefore defined, including hypoxia and anoxia.

The term "flooding stress" refers to any stress which is associated with or induced by prolonged or transient immersion of a plant, plant part, tissue or isolated cell in a liquid medium such as occurs during monsoon, wet season, flash flooding or excessive irrigation of plants, etc.

"Cold stress" and "heat stress" are stresses induced by temperatures that are respectively, below or above, the optimum range of growth temperatures for a particular plant species. Such optimum growth temperature ranges are readily determined or known to those skilled in the art.

"Dehydration stress" is any stress which is associated with or induced by the loss of water, reduced turgor or reduced water content of a cell, tissue, organ or whole plant.

"Drought stress" refers to any stress, which is induced by or associated with the deprivation of water or reduced supply of water to a cell, tissue, organ or organism.

"Oxidative stress" refers to any stress, which increases the intracellular level of reactive oxygen species.

The terms "salinity-induced stress", "salt-stress" or similar term refer to any stress which is associated with or induced by elevated concentrations of salt and which result in a perturbation in the osmotic potential of the intracellular or extracellular environment of a cell.

The transgenic plants obtained in accordance with the method of the present invention, upon the presence of the polynucleic acid and/or regulatory sequence introduced into said plant, attain resistance, tolerance or improved tolerance or resistance against environmental stress which the corresponding wild-type plant was susceptible to.

The terms "tolerance" and "resistance" cover the range of protection from a delay to complete inhibition of alteration in cellular metabolism, reduced cell growth and/or cell death caused by the environmental stress conditions defined herein before. Preferably, the transgenic plant obtained in accordance with the method of the present invention is tolerant or resistant to environmental stress conditions in the sense that said plant is capable of growing substantially normal under environmental conditions where the corresponding wild-type plant shows reduced growth, metabolism, viability, productivity and/or male or female sterility. As used herein, "stress tolerance" refers to the capacity to grow and produce biomass during stress, the capacity to reinitiate growth and biomass production after stress, and the capacity to survive stress. The term "stress tolerance" also covers the capacity of the plant to undergo its developmental program during stress similarly to under non-stressed conditions, e.g. to switch from dormancy to germination and from vegetative to reproductive phase under stressed conditions similarly as under non-stressed conditions. Methodologies to determine plant growth or response to stress include, but are not limited to height measurements, leaf area, plant water relations, ability to flower, ability to generate progeny and yield or any other methodology known to those skilled in the art.

"Growth" refers to the capacity of the plant or of plant parts to grow and increase in biomass while "yield" refers to the harvestable biomass of plants or plant parts, particularly those parts of commercial value. "Growth and/or yield under stressed and non-stressed conditions" refers to the fact that field-grown plants almost always will experience some form of stress, albeit mild. It is therefore preferred not to distinguish non-stressed from mild-stressed conditions. As certain beneficial effects of the invention on growth and yield are expected to occur under both severe and mild stress conditions, they are thus described as increasing growth and/or yield under stressed and non-stressed conditions.

Means for introducing recombinant DNA into plant tissue or cells include, but are not limited to, transformation using $CaCl_2$ and variations thereof, in particular the method described previously (Hanahan 1983), direct DNA uptake into protoplasts (Krens et al. 1982; Paszkowski et al. 1984), PEG-mediated uptake to protoplasts (Armstrong et al. 1990) microparticle bombardment, electroporation (Fromm et al. 1985), microinjection of DNA (Crossway et al. 1986; Fromm et al. 1985), microparticle bombardment of tissue explants or cells (Christou et al. 1988), vacuum-infiltration of tissue with nucleic acid, or in the case of plants, T-DNA-mediated transfer from *Agrobacterium* to the plant tissue as described essentially (An et al. 1985; Dodds 1985; Herrera-Estrella et al. 1983a; Herrera-Estrella et al. 1983b). Methods for transformation of monocotyledonous plants are well known in the art and include *Agrobacterium*-mediated transformation (Cheng et al. 1997—WO9748814; Hansen 1998—WO9854961, Hiei et al. 1994—WO9400977; Hiei et al. 1998—WO9817813; Rikiishi et al. 1999—WO09904618; Saito et al. 1995—WO9506722), microprojectile bombardment (Adams et al. 1999—U.S. Pat. No. 5,969,213; Bowen et al. 1998—U.S. Pat. No. 5,736,369; Chang et al. 1994—WO9413822; Lundquist et al. 1999—U.S. Pat. Nos. 5,874,265/5,990,390; Vasil and Vasil 1995—U.S. Pat. No. 5,405,765; Walker et al. 1999—U.S. Pat. No. 5,955,362), DNA uptake (Eyal et al. 1993—WO9318168), microinjection of *Agrobacterium* cells (von Holt 1994—DE4309203) and sonication (Finer et al. 1997—U.S. Pat. No. 5,693,512).

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the gene construct may incorporate a plasmid capable of replicating in the cell to be transformed. Examples of microparticles suitable for use in such systems include 1 to 5 μm gold spheres. The DNA construct may be deposited on the microparticle by any suitable technique, such as by precipitation.

A whole plant may be regenerated from the transformed or transfected cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The term "organogenesis", as used herein, means a process by which shoots and roots are developed sequentially from meristematic centers.

The term "embryogenesis", as used herein, means a process by which shoots and roots develop together in a concerted fashion (not sequentially), whether from somatic cells or gametes.

Preferably, the plant is produced according to the inventive method is transfected or transformed with a genetic sequence, or amenable to the introduction of a protein, by any art-recognized means, such as microprojectile bombardment, microinjection, *Agrobacterium*-mediated transformation (including the flower dip transformation method; (Bechtold & Pelletier 1998; Trieu et al. 2000)), protoplast fusion, or electroporation, amongst others. Most preferably staid plant is produced by *Agrobacterium*-mediated transformation.

The "seedling" is the juvenile plant that arises from the mature embryo after seed germination.

With "differeritiation of a cell" it is understood that the cell develops unique features to be engaged for a specific function. Mostly differentiation is irreversible.

*Agrobacterium*-mediated transformation or agrolistic transformation of plants, yeast, moulds or filamentous fungi is based on the transfer of part of the transformation vector sequences, called the T-DNA, to the nucleus and on integration of said T-DNA in the genome of said eukaryote.

With "*Agrobacterium*" is meant a member of the Agrobacteriaceae, more preferably *Agrobacterium* or *Rhizobacterium* and most preferably *Agrobacterium tumefaciens*.

With "T-DNA", or transferred DNA, is meant that part of the transformation vector flanked by T-DNA borders which is, after activation of the *Agrobacterium* vir genes, nicked at the T-DNA borders and is transferred as a single stranded DNA to the nucleus of an eukaryotic cell.

When used herein, with "T-DNA borders", "T-DNA border region", or "border region" are meant either right T-DNA border (RB) or left T-DNA border (LB). Such a border comprises a core sequence flanked by a border inner region as part of the T-DNA flanking the border and/or a border outer region as part of the vector backbone flanking the border. The core sequences comprise 22 bp in case of octopine-type vectors and 25 bp in case of nopaline-type vectors. The core sequences in the right border region and left border region form imperfect repeats. Border core sequences are indispensable for recognition and processing by the *Agrobacterium* nicking complex consisting of at least VirD1 and VirD2. Core sequences flanking a T-DNA are sufficient to promote transfer of said T-DNA. However, efficiency of transformation using transformation vectors carrying said T-DNA solely flanked by said core sequences is low. Border inner and outer regions are known to modulate efficiency of T-DNA transfer (Wang et al. 1987). One element enhancing T-DNA transfer has been characterised and resides in the right border outer region and is called overdrive (Peralta et al. 1986; van Haaren et al. 1987).

With "T-DNA transformation vector" or "T-DNA vector" is meant any vector encompassing a T-DNA sequence flanked by a right and left T-DNA border consisting of at least the right and left border core sequences, respectively, and used for transformation of any eukaryotic cell.

With "T-DNA vector backbone sequence" or "T-DNA vector backbone sequences" is meant all DNA of a T-DNA containing vector that lies outside of the T-DNA borders and, more specifically, outside the nicking sites of the border core imperfect repeats.

The current invention includes optimised T-DNA vectors such that vector backbone integration in the genome of a eukaryotic cell is minimised or absent. With "optimised T-DNA vector" is meant a T-DNA vector designed either to decrease or abolish transfer of vector backbone sequences to the genome of a eukaryotic cell. Such T-DNA vectors are known to the one familiar with the art and include those described previously (Hanson et al. 1999), Stuiver et al. (1999-WO9901563).

The current invention clearly considers the inclusion of a DNA sequence of the present invention encoding a DRE-binding factor DBF1, homologue, derivative or immunologically active fragment thereof as defined supra, in any T-DNA vector comprising binary transformation vectors, super-binary transformation vectors, co-integrate transformation vectors, Ri-derived transformation vectors as well as in T-DNA carrying vectors used in agrolistic transformation.

With "binary transformation vector" is meant a T-DNA transformation vector comprising: a T-DNA region comprising at least one gene of interest and/or at least one selectable marker active in the eukaryotic cell to be transformed; and a vector backbone region comprising at least origins of replication active in *E. coli* and *Agrobacterium* and markers for selection in *E. coli* and *Agrobacterium*. Alternatively, replication of the binary transformation vector in *Agrobacterium* is dependent on the presence of a separate helper plasmid. The binary vector pGreen and the helper plasmid pSoup form an example of such a system as described in e.g. (Hellens et al. 2000) or as available on the internet site.

The T-DNA borders of a binary transformation vector can be derived from octopine-type or nopaline-type Ti plasmids or from both. The T-DNA of a binary vector is only transferred to a eukaryotic cell in conjunction with a helper plasmid. Also known in the art are multiple binary vector *Agrobacterium* strains for efficient co-transformation of plants (Bidney and Scelonge 2000—WO0018939).

With "helper plasmid" is meant a plasmid that is stably maintained in *Agrobacterium* and is at least carrying the set of vir genes necessary far enabling transfer of the T-DNA. Said set of vir genes can be derived from either octopine-type or nopaline-type Ti plasmids or from both.

With "super-binary transformation vector" is meant a binary transformation vector additionally carrying in the vector backbone region a vir region of the Ti plasmid pTiBo542 of the super-virulent *A. tumefaciens* strain A281 (Hiei et al. 1994-EP0604662, Hiei et al. 1995—EP0687730). Super-binary transformation vectors are used in conjunction with a helper plasmid.

With "co-integrate transformation vector" is meant a T-DNA vector at least comprising:
a T-DNA region comprising at least one gene of interest and/or at least one selectable marker active in plants; and
a vector backbone region comprising at least origins of replication active in *Escherichia coli* and *Agrobacterium*, and markers for selection in *E. coli* and *Agrobacterium*, and a set of vir genes necessary for enabling transfer of the T-DNA.

The T-DNA borders and said set of vir genes of a said T-DNA vector can be derived from either octopine-type or nopaline-type Ti plasmids or from both.

With "Ri-derived plant transformation vector" is meant a binary transformation vector in which the T-DNA borders are derived from a Ti plasmid and said binary transformation vector being used in conjunction with a 'helper' Ri-plasmid carrying the necessary set of vir genes.

As used herein, the term "selectable marker gene" or "selectable marker" or "marker for selection" includes any gene which confers a phenotype on a cell in which it is expressed to facilitate the identification and/or selection of cells which are transfected or transformed with a gene construct of the invention or a derivative thereof. Suitable selectable marker genes contemplated herein include the ampicillin resistance (Amp$^r$), tetracycline resistance gene (Tc$^r$), bacterial kanamycin resistance gene (Kan$^r$), phosphinothricin resistance gene, neomycin phosphotransferase gene (nptII), hygromycin resistance gene, β-glucuronidase (GUS) gene, chloramphenicol acetyltransferase (CAT) gene, green fluorescent protein (gfp) gene (Haseloff et al. 1997), and luciferase gene, amongst others.

With "agrolistics", "agrolistic transformation" or "agrolistic transfer" is meant here a transformation method combining features of *Agrobacterium*-mediated transformation and of biolistic DNA delivery. As such, a T-DNA containing target plasmid is co-delivered with DNA/RNA enabling in planta production of VirD1 and VirD2 with or without VirE2 (Hansen & Chilton 1996; Hansen et al. 1997), (Hansen and Chilton 1997—WO9712046).

The present invention further describes an approach to remove from transformed cells a stably integrated foreign DNA sequence by recombination involving a recombinase and recombination sites.

With "foreign DNA" is meant any DNA sequence that is introduced in the host s genome by recombinant techniques. Said foreign DNA includes e.g. a T-DNA sequence or a part thereof such as the T-DNA sequence comprising the selectable marker in an expressible format. Foreign DNA furthermore includes intervening DNA sequences as defined supra.

With "recombination event" is meant either a site-specific recombination event or a recombination event effected by transposon jumping.

With "recombinase" is meant either a site-specific recombinase or a transposase.

With "recombination site" is meant either site-specific recombination sites or transposon border sequences.

With "site specific recombination event" is meant an event catalysed by a system generally consisting of three elements: a pair of DNA sequences (the site-specific recombination sequences or sites) and a specific enzyme (the site-specific recombinase). The site-specific recombinase catalyzes a recombination reaction only between two site-specific recombination sequences depending on the orientation of the site-specific recombination sequences. Sequences intervening between two site-specific recombination sites will be inverted in the presence of the site-specific recombinase when the site-specific recombination sequences are oriented in opposite directions relative to one another (i.e. inverted repeats). If the site-specific recombination sequences are oriented in the same direction relative to one another (i.e. direct repeats), then any intervening sequences will be deleted upon interaction with the site-specific recombinase. Thus, if the site-specific recombination sequences are present as direct repeats at both ends of a foreign DNA sequence integrated into a eukaryotic genome, such integration of said sequences can subsequently be reversed by interaction of the site-specific recombination sequences with the corresponding site specific recombinase. A number of different site specific recombinase systems can be used including but not limited to the Cre/lox system of bacteriophage P1, the FLP/FRT system of yeast, the Gin recombinase of phage Mu, the Pin recombinase of *E. coli*, the PinB, PinD. and PinF from *Shigella*, and the R/RS system of *Zygosaccharomyces rouxii*. Recombinases generally are integrases, resolvases or flippases. Also dual-specific recombinases can be used in conjunction with direct or indirect repeats of two different site-specific recombination sites corresponding to the dual-specific recombinase. (Baszczynski et al. 1999—WO9925840). The preferred site-specific recombinase systems are the bacteriophage P1 Cre/lox, the yeast FLP/FRT and the *Z. rouxii* R/RS systems. In these systems a recombinase (Cre, FLP or R) interact specifically with its respective site-specific recombination sequence (lox, FRT, or RS respectively) to invert or excise the intervening sequences. The site-specific recombination sequences for each of these two systems are relatively short (34 bp for lox and 47 bp for FRT). Some of these systems have already been used with high efficiency in plants such as tobacco (Dale & Ow 1990; Onouchi et al 1991; Sugita et al. 2000) and *Arabidopsis* (Onouchi et al 1995; Osborne et al. 1995). Site-specific recombination systems have many applications in plant molecular biology including methods for control of homologous recombination (e.g. Hodges et al. 1996—U.S. Pat. No. 5,527,695), for targeted insertion, gene stacking, etc. (Baszczynski et al. 1999—WO9925821) and for resolution of complex T-DNA integration patterns or for excision of a selectable marker (Ow et al. 1999—WO9923202);

Although the site-specific recombination sequences must be linked to the ends of the DNA to be excised or to be inverted, the gene encoding the site-specific recombinase may be located elsewhere. For example, the recombinase gene could already be present in the eukaryote's DNA or could be supplied by a later introduced DNA fragment either introduced directly into cells, through crossing or through cross-pollination. Alternatively, a substantially purified recombinase protein could be introduced directly into the eukaryotic cell, e.g. by microinjection or particle bombardment. Typically, the site-specific recombinase coding region will be operably linked to regulatory sequences enabling expression of the site-specific recombinase in the eukaryotic cell.

With "recombination event effected by transposon jumping" or "transposase-mediated recombination" is meant a recombination event catalysed by a system consisting of three elements: a pair of DNA sequences (the transposon border sequences) and a specific enzyme (the transposase). The transposase catalyses a recombination reaction only between two transposon border sequences which are arranged as inverted repeats. A number of different transposon/transposase systems can be used including but not limited to the Ds/Ac system, the Spm system and the Mu system. These systems originate from corn but it has been shown that at least the Ds/Ac and the Spm system also function in other plants (Fedoroff & Smith 1993; Schlappi et al. 1993; Van Sluys et al. 1987). Preferred are the: Ds- and the Spm-type transposons which are delineated by 11 bp- and 13 bp-border sequences, respectively.

Although the transposon border sequences must be linked to the ends of the DNA to be excised, the gene encoding the transposase may be located elsewhere. For example, the recombinase gene could already be present in the eukaryote's DNA or could be supplied by a later introduced DNA fragment either introduced directly into cells, through crossing or through cross-pollination. Alternatively, a substantially purified transposase protein could be introduced directly into cells, e.g. by microinjection or by particle bombardment.

As part of the current invention, transposon border sequences are included in a foreign DNA sequence such that they lie outside said DNA sequence and transform said DNA into a transposon-like entity that can move by the action of a transposase.

As transposons often reintegrate at another locus of the host's genome, segregation of the progeny of the hosts in which the transposase was allowed to act might be necessary to separate transformed hosts containing e.g. only the transposon footprint and transformed hosts still containing the foreign DNA.

In performing the present invention, the genetic element is preferably induced to mobilise, such as, for example, by the expression of a recombinase protein in the cell which contacts the integration site of the genetic element and facilitates a recombination event therein, excising the genetic element completely, or alternatively, leaving a "footprint", generally of about 20 nucleotides in length or greater, at the original integration site. Those hosts and host parts that have been produced according to the inventive method can be identified by standard nucleic acid hybridization and/or amplification techniques to detect the presence of the mobilizable genetic element or a gene construct comprising the same. Alternatively, in the case of transformed host cells, tissues, and hosts wherein the mobilizable genetic element has been excised, it is possible to detect a footprint in the genome of the host which has been left following the excision event, using such techniques. As used herein, the term "footprint" shall be taken to refer to any derivative of a mobilizable genetic element or gene construct comprising the same as described herein which is produced by excision, deletion or other removal of the mobilizable genetic element from the genome of a cell transformed previously with said gene construct. A footprint generally comprises at least a single copy of the recombination loci or transposon used to promote excision. However, a footprint may comprise additional sequences derived from the gene construct, for example nucleotide sequences derived from the left border sequence, right border sequence, origin of replication, recombinase-encoding or transposase-encoding sequence if used, or other vector-derived nucleotide sequences. Accordingly, a footprint is identifiable according to the nucleotide sequence of the recombination locus or transposon of the gene construct used, such as, for example, a sequence of nucleotides corresponding or complementary to a lox site, fit site or RS site.

With "pathogen" is meant those organisms that have a negative effect on the physiological state of the plant or a part thereof. Some pathogens are for instance viruses, bacteria, fungi, and parasitic plants. With plant "pests" is meant the group of nematodes as well as insects, which are able to exert a negative effect on the physiological state of the plant or a part thereof.

"Plant cell" comprises any cell derived from any plant and existing in culture as a single cell, a group of cells or a callus. A plant cell may also be any cell in a developing or mature plant in culture or growing in nature.

"Plants" comprises all plants, including monocotyledonous and dicotyledonous plants.

"Cereal" comprises crop plants with edible grain for example plants belonging to the grass family that is cultivated for its nutritious grains such as oats, barley, rye, wheat, rice, and corn etc.

With "yeast two-hybrid assay" is meant an assay that is based on the observation that many eukaryotic transcription factors comprise two domains, a DNA-binding domain (DB) and an activation domain (AD) which, when physically separated (i.e. disruption of the covalent linkage) do not effectuate target gene expression. Two proteins able to interact physically with one of said proteins fused to DB and the other of said proteins fused to AD will re-unite the DB and AD domains of the transcription factor resulting in target gene expression. The target gene in the yeast two-hybrid assay is usually a reporter gene such as the β-galactosidase gene. Interaction between protein partners in the yeast two-hybrid assay can thus be quantified by measuring the activity of the reporter gene product (Bartel & Fields 1997). Alternatively, a mammalian two-hybrid system can be used which includes e.g. a chimeric green fluorescent protein encoding reporter gene (Shioda et al. 2000). Yet another alternative consists of a bacterial two-hybrid system using e.g. HIS as reporter gene (Joung et al. 2000).

The term "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity or the original sequence referred to while the maximum size is not critical. In some applications, the maximum size usually is not substantially greater than that required to provide the desired activity and/or function(s) of the original sequence. Typically, the truncated amino acid or nucleotide sequence will range from about 5 to about 60 amino acids in length. More typically, however, the sequence will at least be about 50 amino acids in lenght, preferably a maximum of (or at least) about 60, 80,100, 120,150, 200 or 220 amino acids. It is usually desirable to select sequences of at least about 10, 12 or 15 amino acids, up to a maximum of about 20 or 25 amino acids.

"Part of a nucleic acid sequence" refers to a sequence which has at least about 20 nucleotides in lenght, preferably a maximum of (or at least) about 25, 50, 60, 80, 100, 200, 250, 300, 400, 500, 600, 700, 750, 800, 900, or 1000 nucleotides.

Furthermore, folding simulations and computer redesign of structural motifs of the protein of the invention can be performed using appropriate computer programs (Hoffman et al. 1995; Olszewski et al. 1996). Computer modeling of protein folding can be used for the conformational and energetic analysis of detailed peptide and protein models (Monge et al. 1995; Renouf & Hounsell 1995). In particular, the appropriate programs can be used for the identification of interactive sites of the DRE binding protein (DBF1) of the present invention by computer assistant searches for complementary peptide sequences (Fassina & Melli 1994). Further appropriate computer systems for the design of protein and peptides are described in the prior art e.g. (Berry & Brenner 1994; Pabo & Suchanek 1986; Wodak 1987). The results obtained form the above-described computer analysis can be used for, e.g. the preparation of peptidomimetics of the protein of the invention or fragments thereof. Such pseudopeptide analogues of the natural amino acid sequence of the protein may very efficiently mimic the parent protein (Benkirane et al 1996). For example, incorporation of easily available achiralω-amino acid residues into a protein of the invention or a fragment thereof results in the substitution of amino bonds by polymethylene units of an aliphatic chain, thereby providing a convenient strategy for constructing a peptidomimetic (Banerjee et al. 1996). Superactive peptidomimetic analogues of small peptide hormones in other systems are described in the prior art (Zhang et al. 1996). Appropriate peptidomimetics of the protein of the present invention can also be identified by the synthesis of peptidomimetic combinatorial libraries through successive amine alkylation and testing the resulting compounds, e.g., for their binding, kinase inhibitory and/or immunlogical properties. Methods for the generation and use of peptidomimetic combinatorial libraries are described in the prior art e.g. (Dorner et al. 1996; Ostresh et al. 1996).

Furthermore, a three-dimensional and/or crystallographic structure of the protein of the invention can be used for the design of peptidomimetic inhibitors of the biological activity of the protein of the invention (Rose et al. 1996; Rutenber et at 1996).

The compounds to be obtained or identified in the methods of the invention can be compounds that are able to bind to any of the nucleic acids, peptides or proteins of the invention. Other interesting compounds to be identified are compounds that modulate the expression of the genes or the proteins of the invention in such a way that either the expression of said gene or protein is enhanced or decreased by the action of, said compound. Alternatively the compound can exert his action by directly or indirectly enhancing or decreasing the activity of any of the proteins of the invention.

Said compound or plurality of compounds may be comprised in, for example, samples, e.g., cell extracts from, e.g., plants, animals or microorganisms. Furthermore, said compound(s) may be known in the art but hitherto not known to be capable of suppressing or activating cell cycle interacting proteins. The reaction mixture may be a cell free extract of may comprise a cell or tissue culture. Suitable set ups for the method of the invention are known to the person skilled in the art and are, for example, generally described previously (Alberts et al. 1994), in particular Chapter 17. The plurality of compounds may be, e.g., added to the reaction mixture, culture medium or injected into the cell.

If a sample containing a compound or a plurality of compounds is identified in the method of the invention, then it is either possible to isolate the compound form the original sample identified as containing the compound capable of acting as an agonist, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances or similar chemical and/or physical properties, and most preferably said substances are identical. Preferably, the compound identified according to the above-described method or its derivative is further formulated in a form suitable for the application in plant breeding or plant cell and tissue culture.

AP2/EREBP domain-containing transcription factor is the widely accepted denomination of a family of DNA binding proteins that contain a DNA binding domain of approximately 60 amino acids which is rather well-conserved in sequence among the different family members. Examples of such sequences are described in Ohme-Takagi and Shinshi (Plant Cell 1995; 7: 173-182), Weigel (Plant Cell 1995; 7: 388-389), and Mushegian and Koonin (Genetics 1996; 144: 817-828). This domain is generally referred to as apetala, AP2, EREBP or AP2/EREBP domain. Those skilled in the art can readily identify the presence of an AP2/EREBP domain in polypeptide and protein sequences, for example through publicly accessible sites on Internet. For example, the Pfam 5.5 program of the Washington University at St-Louis allows to screen for AP2/EREBP domains in given polypeptide or protein sequences.

The expression "DRE element" as used herein relates to "drought responsive element". This is a cis element known in the art, with the general consensus sequence DRE: TACCGA-CAT (Busk et al, The Plant Journal (1997) 11 (6); 1285-1295). DRE elements are frequently found in the promoters of genes that are involved in stress tolerance. The terms DRE1 and DRE2 as used herein refer to the DRE elements found in the rab17 promoter of Maize that have the sequences "ACCGA" and "ACCGACG" respectively (see also Busk et al, 1997).

Also DRE-related motifs have been reported in the promoter regions of cold and drought inducible genes such as lin1, cor6.6, rd17 (reviewed in Liu et al., The plant cell (1998) 10, 1391-1406). A similar motif was also reported (C repeat; "TGGCCGAC" in the promoter regions of the cold-inducible cor 15 a. The "CCGAC" core sequence was found in the promoter regions of cold-inducible oil-seed rape gene BN115 and designated the low temperature-responsive element.

The expression "DRE element" as used herein relates to the particular DRE element sequences as mentioned above, as well as to these elements in the context of a natural promoter for example, in the context of at least a part of the rab17 promoter of maize or at least part of a promoter of a homologous gene and/or other stress genes (e.g. dehydrins, Lea D-11, COR etc.) and/or any other gene. Also, when the expression "DRE element" is used herein we refer to a DRE element in the context of a synthetic promoter or a chimeric promoter, to one copy of the DRE element or to, multiple copies of the DRE element (such as in SEQ ID NO 1).

The present invention is further described by reference to the following non-limiting figures and examples.

BRIEF DESCRIPTION OF THE FIGURES

FIG. 1B contains the following sequences: RAPLDPAVDAKLQAIC (SEQ ID NO: 23). YKPLHSSVNAKLEAIC (SEQ ID NO: 24), YQPLQSSVDAKLEAIC (SEQ ID NO: 25). FNPLHSSVDAKLQEIC (SEQ ID NO: 26), OSSSSKLLSATLIAKL (SEQ ID NO: 27), RLRIPESTCAKDIQKA (SEQ ID NO: 28).

FIG. 8: List of sequences and corresponding SEQ ID NOs.

EXAMPLES

Example 1

Figure 1:
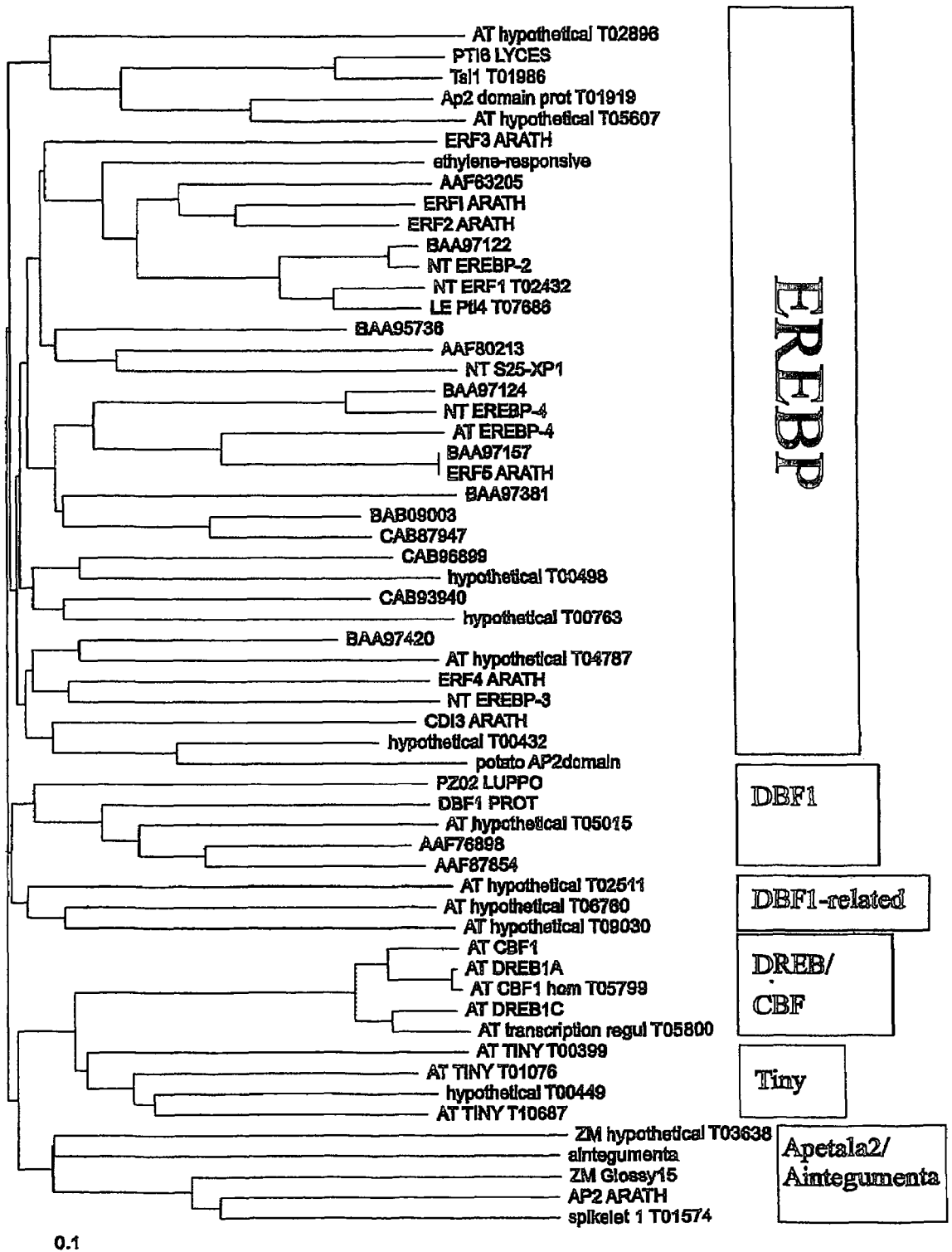
FIG. 1:
A. Tree representation of sequence similarities between various members of the AP2 domain-containing superfamily of putative transcription factors. Please note that not all sequences with AP2 domains were incorporated. Alignments were made with the CLUSTALW program (Blosum 32 series, Gap penalty 10.00 and Gap extension 0.05). The names at the right side of the tree refer to AP2 domain proteins of known function that are representative for each class of AP2 domain proteins.
B. Partial amino acid alignment of DBF1 and most closely related sequences, showing sequence conservation outside the AP2 domain. The DREB1A and CBF1 sequences are given to illustrate the specificity of the sequence conservation to DBF1 and closely related sequences. A tentative consensus sequence is given in bold. Numbers on top of the figure refer to the amino acid position in the DBF1 sequence.

Isolation of cDNAs Encoding DRE2 Binding Proteins Using the Yeast One-hybrid Screen The yeast one-hybrid screening system (Clontech®) was used in order to isolate cDNA clones that encode DNA binding proteins that interact with the DRE2 cis-element of the rab17 promoter. To this aim, a dual reporter yeast strain was generated. A synthetic oligonucleotide containing three tandem repeats of the cis-element DRE2 from the rab17 promoter (Busk et al., Plant J. 11:1285-1295, 1997) with EcoRI and XbaI or EcoRI and SalI restriction sites at its 5' and 3' ends was cloned in the corresponding restriction enzyme sites in the multilinkers of the pHISi-1 and pLacZi plasmids respectively. The double reporter yeast strain was obtained by transforming the yeast strain YM4271 with the above placZi and pHISi-1 plasmid constructs sequentially. The yeast transformants were subjected to β-galactosidase and 3-AT control tests for determination of the background expression activity. The yeast transformants that did not show lacZ activity and were not able to grow in the presence of 40 mM 3-aminotriazol (3-AT) were selected for subsequent use in the cDNA library screening with the one-hybrid system.

An expression cDNA fusion library was constructed from leaves of five day old maize plantlets that were previously water stressed for three hours. Total RNA was extracted as described previously (Vilardell et al., Plant Mol Biol 17:985-993, 1991). Poly(A)⁺mRNA was obtained by using the polyATtract® mRNA kit (Promega). The cDNA was prepared using the Stratagene cDNA synthesis-kit and was subsequently cloned to the HybriZap phagemid vector (Stratagene). The cDNA library was transformed into the dual reporter yeast strain and approximately $1.4 \times 10^6$ yeast transformants were screened in the presence of 40 mM 3-AT. A large number of 3-AT resistant clones were selected and subsequently tested for lacZ activity by using an X-gal filter assay. Fourteen of the clones induced lacZ activity and formed blue colonies. The corresponding cDNAs were further analysed by restriction enzyme digestion and DNA sequencing, resulting in two groups which consisted of six and eight clones with cDNA inserts of 1 and 1.2 kb respectively.

Example 2

Nucleotide and Amino Acid Sequence of a DRE2 Binding Protein According to the Invention DBF1 is an example of cDNA that encodes a protein which binds to the DRE2 cis element. The nucleotide and amino acid sequence of DBF1 are given as SEQ ID NO 2 and SEQ ID NO 3, respectively. The DBF1 cDNA contains an open reading frame of 222 amino acids and encodes a putative protein with a theoretical molecular mass of 24 kD.

Example 3

Database Blast Analysis with the DBF1 Amino Acid Sequence

The DBF1 amino acid sequence was blasted against the nr (All non-redundant GenBank CDS translations+PDB+SwissProt+PIR) (using BLASTP program) and GPT_DNA (Rijksunoversiteit Gent—Vlaams Interuniverisair Instituut voor biotechnologie, K. L. Ledegenkstraat 35, B-9000 Gent; (using TBLASTN program) databases. Results from both blast searches showed essentially the same picture, namely:

1. DBF1 shows the highest similarity to a class of AP2 domain-containing proteins of unknown function. E values of DBF1 with this class of proteins range between $e^{-39}$ and $e^{-46}$. Examples are the proteins encoded by the sequences with accession numbers AC009243, AC024228, AC021666, AC006228, AC012680, AL161595, AC007168 and AB013395.

2. DBF1 shows high similarity to a class of AP2 domain-containing proteins of unknown function. E values of DBF1 with this class of proteins range between $e^{-27}$ and $e^{-29}$. Examples are the proteins with accession numbers AC066689, AL161537, and AC006234.

3. DBF1 shows less homology to AP2 domain-containing proteins of known function such as ABI4, CBF1, DREB1A, proteins of the EREB family, aintegumenta, and AP2. E values of DBF1 with this AP2 containing proteins of known function are in all cases higher than $e^{-20}$.

It is concluded therefore that DBF1 represents a separate class of AP2 domain-containing proteins, of which the function was hitherto unknown.

The top hits with the TBLASTN program against the GPT_DNA database are shown below:

| Sequences producing significant alignments: | Score (bits) | E Value |
|---|---|---|
| AC009243_gene25strand + L = 1005 UTR = 30bp (108054 . . . 109058) | 179 | 2e-45 |
| AC024228_gene3strand − L = 786 UTR = 30bp (7956 . . . 8741) | 176 | 2e-44 |
| AC021666_gene4strand + L = 945 UTR = 30bp (19304 . . . 20248) | 174 | 9e-44 |
| AC006228_gene4strand − L = 945 UTR = 30bp (15461 . . . 16405) | 174 | 9e-44 |
| AC012680_gene1strand + incomplete CDS L = 547 UTR = 30bp (12 . . . | 165 | 4e-41 |
| AL161595_gene48strand − L = 819 UTR = 30bp (178386 . . . 179204) | 163 | 2e-40 |
| AC007168_gene13strand + L = 786 UTR = 30bp (48835 . . . 49620) | 161 | 5e-40 |
| AB013395_gene5strand + L = 834 UTR = 30bp (15366 . . . 16199) | 161 | 5e-40 |
| AC066689_gene10strand + L = 1008 UTR = 30bp (56636 . . . 57643) | 127 | 1e-29 |
| AL161537_gene5strand + L = 1032 UTR = 30bp (24381 . . . 25412) | 120 | 1e-27 |
| AC006234_gene16strand − L = 1011 UTR = 30bp (44635 . . . 45645) | 118 | 5e-27 |
| AL161572_gene26strand − L = 879 UTR = 30bp (90388 . . . 91266) | 107 | 1e-23 |
| AL049803_gene2strand − L = 879 UTR = 30bp (1668 . . . 2546) | 107 | 1e-23 |
| AB025637_gene7strand + L = 966 UTR = 30bp (28869 . . . 29097, 29900 . . . | 103 | 2e-22 |
| AB013388_gene9strand − L = 1065 UTR = 30bp (32150 . . . 33214) | 98 | 1e-20 |
| AB018117_gene7strand − L = 732 UTR = 30bp (20365 . . . 21096) | 98 | 1e-20 |
| AL163912_gene4strand + L = 792 UTR = 30bp (20853 . . . 21105, 21291 . . . | 97 | 2e-20 |
| AF085279_gene10strand − L = 987 UTR = 30bp (41637 . . . 42623) | 96 | 2e-20 |
| AB022212_gene1strand − L = 2266 UTR = 30bp (915 . . . 1325, 1685 . . . 19 . . . | 95 | 6e-20 |
| AC016163_gene16strand − L = 552 UTR = 30bp (48434 . . . 48985) | 94 | 9e-20 |
| AC016162_gene8strand − L = 552 UTR = 30bp (15218 . . . 15769) | 94 | 9e-20 |
| U78721_gene3strand − L = 660 UTR = 30bp (12017 . . . 12091, 12359 . . . 1 . . . | 94 | 1e-19 |
| AB026650_gene8strand + L = 1170 UTR = 30bp (23043 . . . 23094, 24382 . . . | 94 | 1e-19 |
| AB022217_gene21strand + L = 747 UTR = 30bp (71834 . . . 71993, 72232 . . . | 94 | 2e-19 |
| AC005405_gene4strand − L = 657 UTR = 30bp (19886 . . . 20542) | 94 | 2e-19 |
| AC004260_gene8strand − L = 657 UTR = 30bp (32878 . . . 32944, 33023 . . . | 93 | 3e-19 |
| AL161560_gene6strand + L = 1032 UTR = 30bp (36135 . . . 37166) | 93 | 3e-19 |
| AL163491_gene13strand + L = 2430 UTR = 30bp (65703 . . . 65986, 6607 . . . | 92 | 4e-19 |
| AC025813_gene6strand + L = 558 UTR = 30bp (22457 . . . 23014) | 92 | 4e-19 |
| AB022220_gene1strand − L = 1125 UTR = 30bp (1520 . . . 1570, 1768 . . . 2 . . . | 92 | 6e-19 |
| AC007591_gene29strand + L = 1176 UTR = 30bp (99139 . . . 99218, 9951 . . . | 92 | 6e-19 |

-continued

| Sequences producing significant alignments: | Score (bits) | E Value |
|---|---|---|
| AL163815_gene18strand – L = 711 UTR = 30bp (89595 . . . 90305) | 91 | 8e-19 |
| AL163814_gene1strand – L = 711 UTR = 30bp (6771 . . . 7481) | 91 | 8e-19 |

This finding was confirmed when a sequence alignment was done with the CLUSTALW program (Blosum 32 series, Gap penalty 10.00 and Gap extension 0.05). A tree representation of this alignment is shown in FIG. 1A. This tree representation again nicely illustrates that DBF1 represents a novel class of AP2 domain transcription factors, that is different from the DREB/CBF class of sequences, the EREBP class of sequences, the TINY class of sequences and the apetala2 and integumenta type sequences.

Furthermore, the sequence alignment shows high sequence conservation between DBF1 and its closest relatives, downstream of the AP2 domain (see FIG. 1B). This sequence is conserved amongst DBF1, T05015, AAF76898, and AAF87854, but not with PZ02_LUPPO, which may indicate that the latter already belongs to a different class of AP2 domain proteins (see also FIG. 1A).

Similar results are obtained with overall sequence similarity calculated with the program GAP. The GAP program aligns two sequences globally (BLOSUM62 amino acid substitution matrix, Gap Weight: 8, Length Weight: 2, Reference: Henikoff, S. and Henikoff, J. G. (1992). Amino acid substitution matrices from protein blocks. Proc. Natl. Acad. Sci. USA 89: 10915-10919). This is illustrated in Table 4 where also the closest homologues of DBF 1 are included. Sequence AB013395 (corresponding protein BAB11649) is shown as an example of a class of sequences with E value of $5e^{-40}$ or less whereas sequence AC006234 (corresponding protein AAD20907) was taken as example of a class of sequence with E value of approximately $e^{-27}$. CBF1 is taken as example of a sequence with E value of approximately $e^{-20}$ or more. As mentioned above, all AP2/EREBP proteins of known function show E values of approximately $e^{-20}$ or more. Also a newly identified Oryza sativa homologue of DBF1 was isolated (see example 8) and was aligned with ZmDBF1.

TABLE 4

% amino acid sequence identity and similarity between DBF1 and other AP2/EREBP proteins

| | % Identity to ZmDBF1 | % similarity to ZmDBF1 |
|---|---|---|
| BAB11649 (AB013395) | 49.8 | 58.2 |
| AAD20907 (AC006234) | 40.3 | 48.9 |
| CBF1 | 33.5 | 38.5 |
| PZ02 LUPPO | 37.9 | 44.4 |
| T05015 | 52.4 | 58.4 |
| AAF76898, | 45.8 | 51.8 |
| AAF87854 | 50 | 55.8 |
| OsDBF1 | 35.3 | 38.4 |

Figure 7:
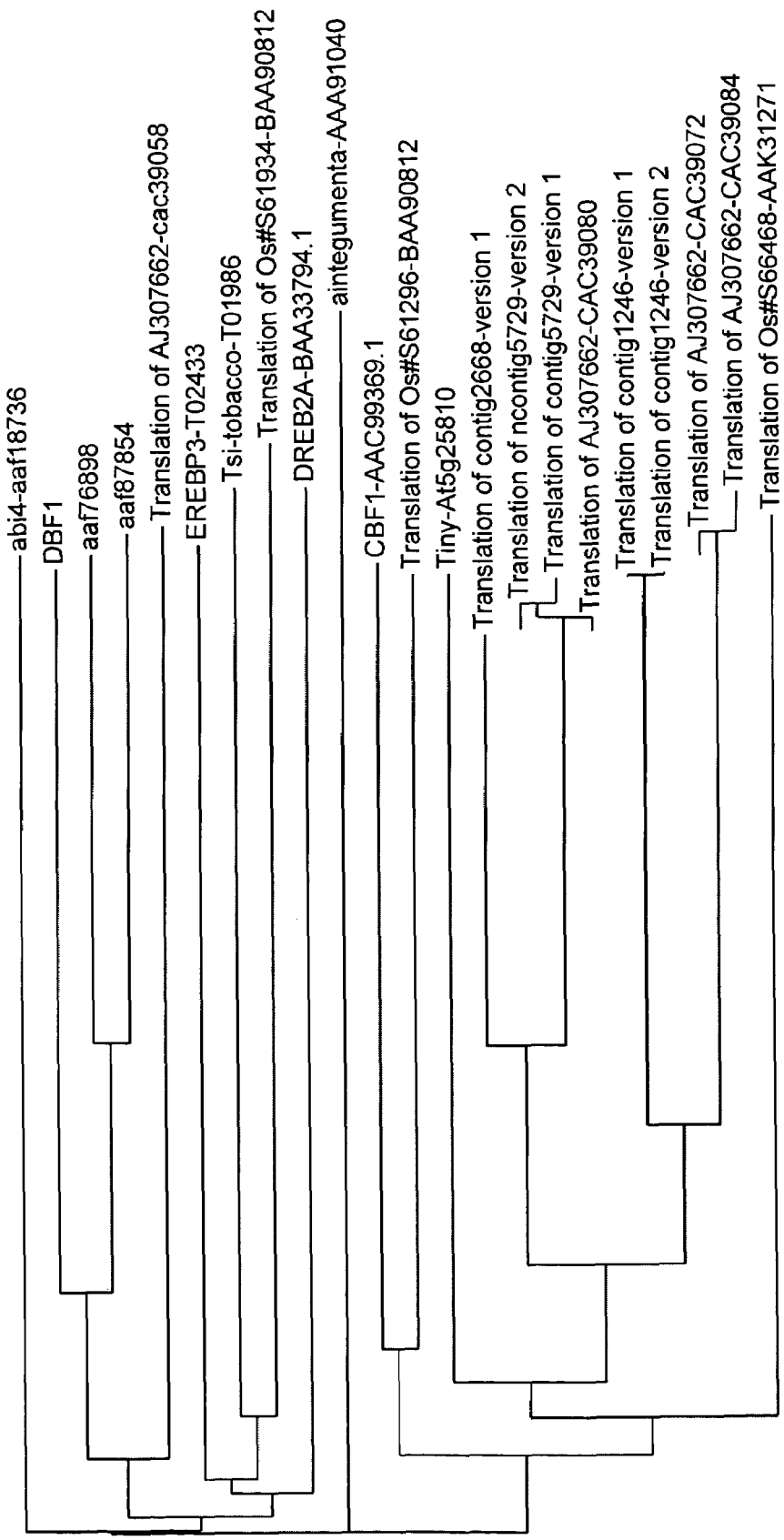
FIG. 7:
A. Tree representation of sequence similarities between various members of the AP2 domain-containing family from rice in comparison with other AP2 proteins from various plant species such as Tobacco and *Arabidopsis*. Alignments were made with the CLUSTALW program (Blosum 32 series, Gap penalty 10.00 and Gap extension 0.05). Previously described DRE binding proteins such as CBF1 or DREB2A from *Arabidopsis* are included, as well as other functionally different AP2 proteins such as ABI4, EREBP or aintegumenta.
B. Pairwise comparison of ZmDBF1 with CAC39058 protein from *Oryza sativa* (OsDBF1, SEQ ID NO 16). The pairwise alignment was made with the CLUSTALW program as described in A.

From this similarity analysis, one can deduce that sequences with 35%, 37%, 40%, and preferentially 50% amino acid sequence identity are closely related to DBF1, while sequences with 33.5% or less amino acid identity are belonging to different classes of AP2/EREBP proteins. The minimum amount of sequence identity that is discriminatory for DBF1 related sequences is therefore between 33.5% and 35%. In accordance, the OsDBF1 and the PZ02 LUPPO protein, which are in the same class as DBF1 in a tree representation (see FIG. 1A and FIG. 7A), but located on a distant branch, shows 35.3% and 37.9% amino acid identity to DBF1 respectively.

Example 4

DBF1 mRNA and Protein Expression is Inducible by ABA and Dehydration Stress

Northern blot hybridizations were performed to study the pattern of mRNA expression of the DBF1 in vegetative tissues of five day old maize plantlets subjected to ABA and various abiotic stress treatments as well as during maize embryogenesis. Total RNA was prepared as described previously (Vilardell et al., Plant Mol Biol 17:985-993, 1991). Total cDNAs were used as probes for all Northern blot hybridisations. Hybridisations for this particular experiment were performed at 42° C. with washes at 65° C. as described previously (Amasino et al., Anal Biochem 152:304-307, 1986).

Figure 2:
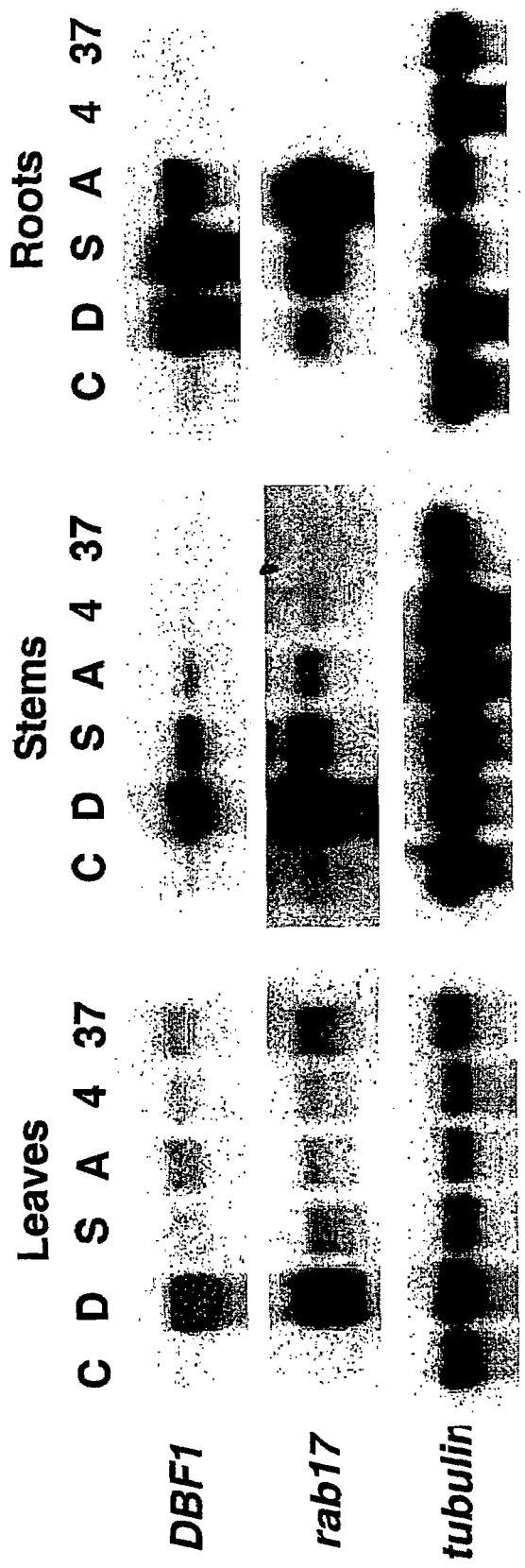
FIG. 2:
Northern analysis showing induction of DBF1 expression by dehydration stress and ABA treatment. The rab17 and tubulin subunit α cDNAs were used as positive and constitutive controls, respectively. Total cDNAs were used as probes for all hybridizations. The total RNA extracts were obtained from 5-day-old plants and are indicated as follows. C: control, 5-day-old plants without additional treatment. D: water stressed plants. S: Plants stressed in a liquid medium of NaCl 250 mM. A: Plants treated with 100 µM ABA. 4: Plants stressed with cold (4° C.). 37: Plants stressed with heat (37° C.).

The DBF1 gene was strongly induced after dehydration stress in all vegetative parts and was also induced by salt and ABA, showing an exeptionally high level of expression in roots (FIG. 2). Cold and heat shock treatments seemed to have a very low to no effect on the mRNA abundance of the DBF1 gene whereas a basal level of transcription was detected in non treated control plants in all cases.

Figure 3:
FIG. 3:
Study of the kinetics of DBF1 induction in vegetative tissues during water stress treatment of maize plantlets. The rab17 and tubulin subunit α cDNAs were used as controls. Total RNA was obtained in different times indicated as follows. The numbers above each lane indicate the time in minutes of water stress treatment that was applied to the plants.

The kinetics of mRNA accumulation of DBF1 and Rab17 were followed during the first hours of dehydration stress (FIG. 3). There is already an increase in DBF1 mRNA levels during the first hour of water stress treatment followed by a further increase afterwards.

In maize embryos, DBF1 mRNA was detected at all stages of embryogenesis and was further induced by ABA treatment in young embryos rab17 mRNA was not observed in young embryos; however, it accumulated to high levels in embryos at later stages of embryogenesis, as well as in young embryos after ABA treatment. These results indicate that the DBF1 gene is highly transcribed in all vegetative tissues after waterstress, salt or ABA treatment as well as in maize embryos during all stages of embryogenesis and after ABA application.

Polyclonal antibodies were raised against total and partial, DBF1 proteins that were expressed and purified from E. coli. The total cDNA as well as a partial fragment of the DBF1 cDNA excluding the fragment that contained the AP2 domain, were cloned as EcoRI, XhoI-fragments into the pET28a and pET28b vectors of the pET overexpression system (PROMEGA). Overexpression and purification of the corresponding proteins was done as described by manufacturers. Rabbit immunization was carried out by three successive injections of 100 μg of purified protein in 500 μl phosphate buffered saline (PBS) emulsified in equal volume of Freund's incomplete adjuvant, as described (Goday et al., Electrophoresis 9:738-741, 1988).

These antibodies were used for DBF1 detection by Western blot analysis of maize plant and embryo protein extracts.

Figure 4:
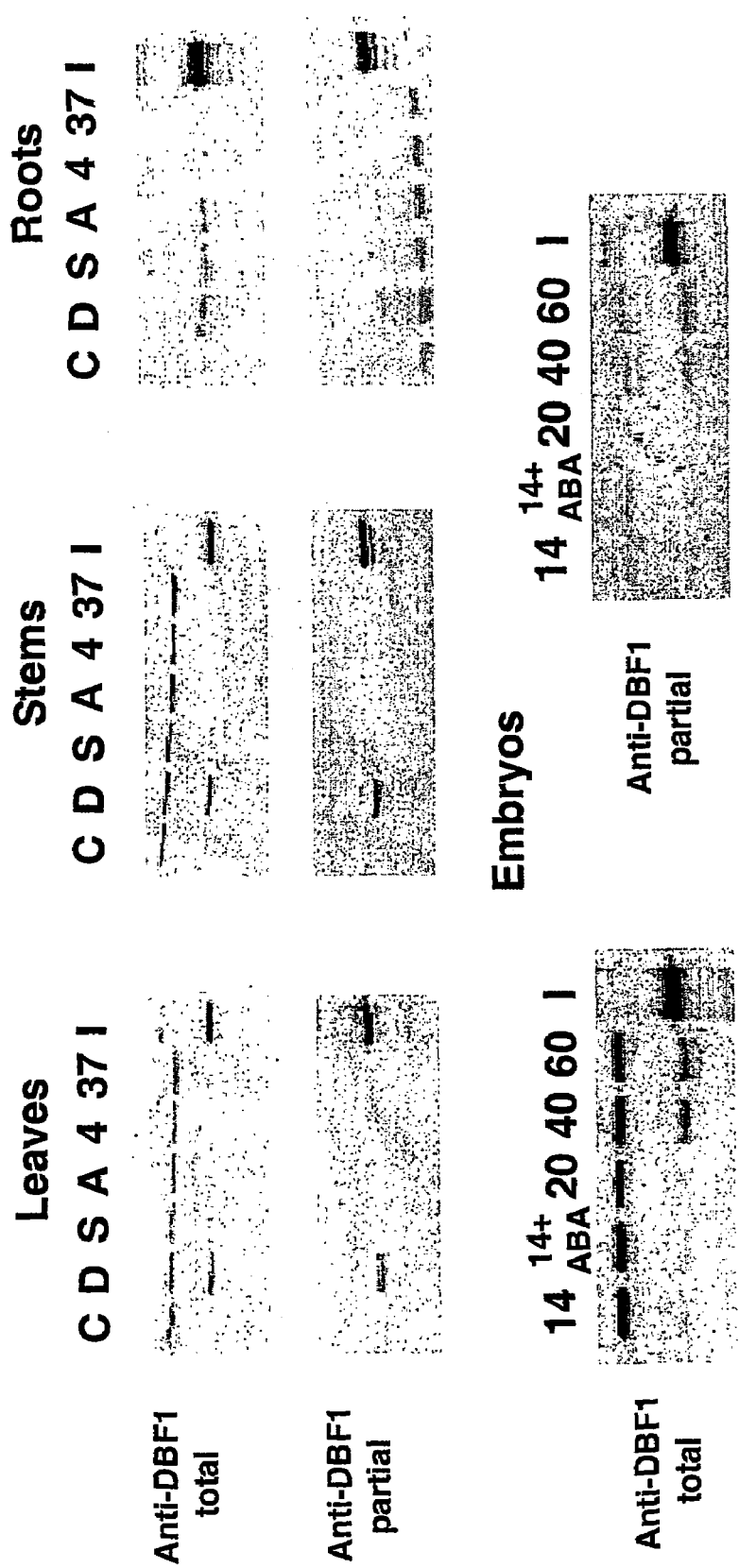
FIG. 4:
Western blot analysis using the anti-DBF1 total protein and anti-DBF1 partial protein antibodies with protein extracts from different parts of maize 5 day old plantlets treated with various types of stresses, and in maize embryos. C: control, 5-day-old plants without additional treatment. D: water stressed plants. S: Plants stressed in a liquid medium of NaCl 250 mM. A: ABA 100 µM treated plants. 4: Plants stressed with cold (4° C.). 37: Plants stressed with heat (37° C.). I: E.coli overexpressed DBF1 total protein. Numbers 14, 20, A40 and 60 indicate days after pollination.

Protein extracts were obtained from five day old plantlets that were previously treated similarly as described for the Northern analysis, and from maize embryos at different stages of embryogenesis. Proteins were extracted by grinding the samples in liquid nitrogen and resuspending the powder in a buffer of 100 mM Tris-HCl pH 7.4, 50 mM NaCl, 5 mM EDTA, 1 mM phenylmethanosulphonyl fluoride (PMSF). Concentration for each extract was determined by using the Bradford assay. Relevant volumes that contained 7 µg of protein were mixed with 2× loading buffer (Tris-HCl 100 mM pH 6.8, SDS 2%, Glycerol 10%, Bromophenol blue 0.003%, mercaptoethanol 10%) and loaded to a 15% acrylamide-bis acrylamide gel. Western blot hybridisations were made as described (Niogret et al., Plant J 9:549-557, 1996). Two sets of western blots were incubated separately with the anti-DBF1 obtained against the total protein (anti-DBF1) or the anti-DBF1 obtained against the partial protein (panti-DBF1) antibodies. FIG. 4 shows that the anti-DBF1 antibody detected a band with an approximate molecular mass of 35 kD in all tissues of water stressed plants. Moreover two bands of the same molecular mass were detected in root extracts of salt and ABA treated plants. The same bands but with a much lower intensity were detected in protein extracts from leaves and stem of plants treated with salt and ABA. The molecular mass of the bands correlates with the predicted molecular mass of the DBF1 protein and it is slightly lower than the *E.coli* expressed protein because of the additional 31 amino acid tag fused to it. Another band with an estimated molecular mass of 70-75 kD was detected as constitutive in protein extracts of all vegetative tissues. However, this protein has a much higher molecular mass than the DBF1 protein. The antibody against the partial DBF1 exhibited more specificity since it does not recognize this protein s of higher molecular weight.

In embryos, the protein is detected during the later stages of embryogenesis and with a lower intensity in the first stages of embryo formation and in young embryos treated with ABA. Our results also showed the expression of the DBF1 in all vegetative tissues after desiccation, salt or ABA treatment.

Example 5

Transient Expression of DBF1 in Maize Callus Enhances Basic and ABA-inducible Activity of the Rab17 Promoter To determine the function of the DRE-DBF1 interaction in the in vivo induction of ABA-regulated promoters, such as rab17, the rab17 promoter activity was monitored in maize callus cells through-transient expression of a reporter protein, beta-glucuronidase (GUS), under control of the rab17 promoter. Callus was made from the maize line Black Mexican Sweet and was maintained as described (Vilardell et al., Plant Mol Biol 14:423-432, 1990) with 3 mg/ml 2,4 dichlorophenoxyacetic acid in the medium. Approximately 1 g of callus was spread on filter paper one day before bombardment and incubated overnight at 26° C. in the dark. Four hours before bombardment the callus was moved to a medium with 200 mM manitol. The callus was transformed by particle bombardment with 2 µg of the rab17prom-GUS plasmid, 1.5 µg pRT-ex/s-int/s-LUC as an internal standard and 1 µg of either pJIT-2×35S-DBF1-nosT or the same construct without insert as described (Klein et al., Nature 327:70-73, 1987). Each sample was divided in two after transformation and incubated in medium with or without 100 µM ABA for 22 hours in the dark at 26° C. before freezing in liquid nitrogen. Luciferase and GUS assays were done as previously described (Busk et al., Plant J. 11:1285-1295, 1997). Relative GUS activity is the reading of the GUS assay divided by the reading of the luciferase assay.

The constructs used consisted either of GUS reporter gene under control of the wild type rab17 promoter (promoter fragment −350/+30 relative to the start of transcription) or of a promoter with mutated DRE2 element. These reporter constructs were cotransformed with an effector plasmid, consisting of the DBF1 cDNA under control of the double 35S promoter. Each combination of effector plasmid with wild type or mutant reporter plasmids was transformed via microprojectile bombardment in maize callus cells. After bombardment half of the samples were incubated with ABA and the other half was kept in MS medium.

Figure 5:
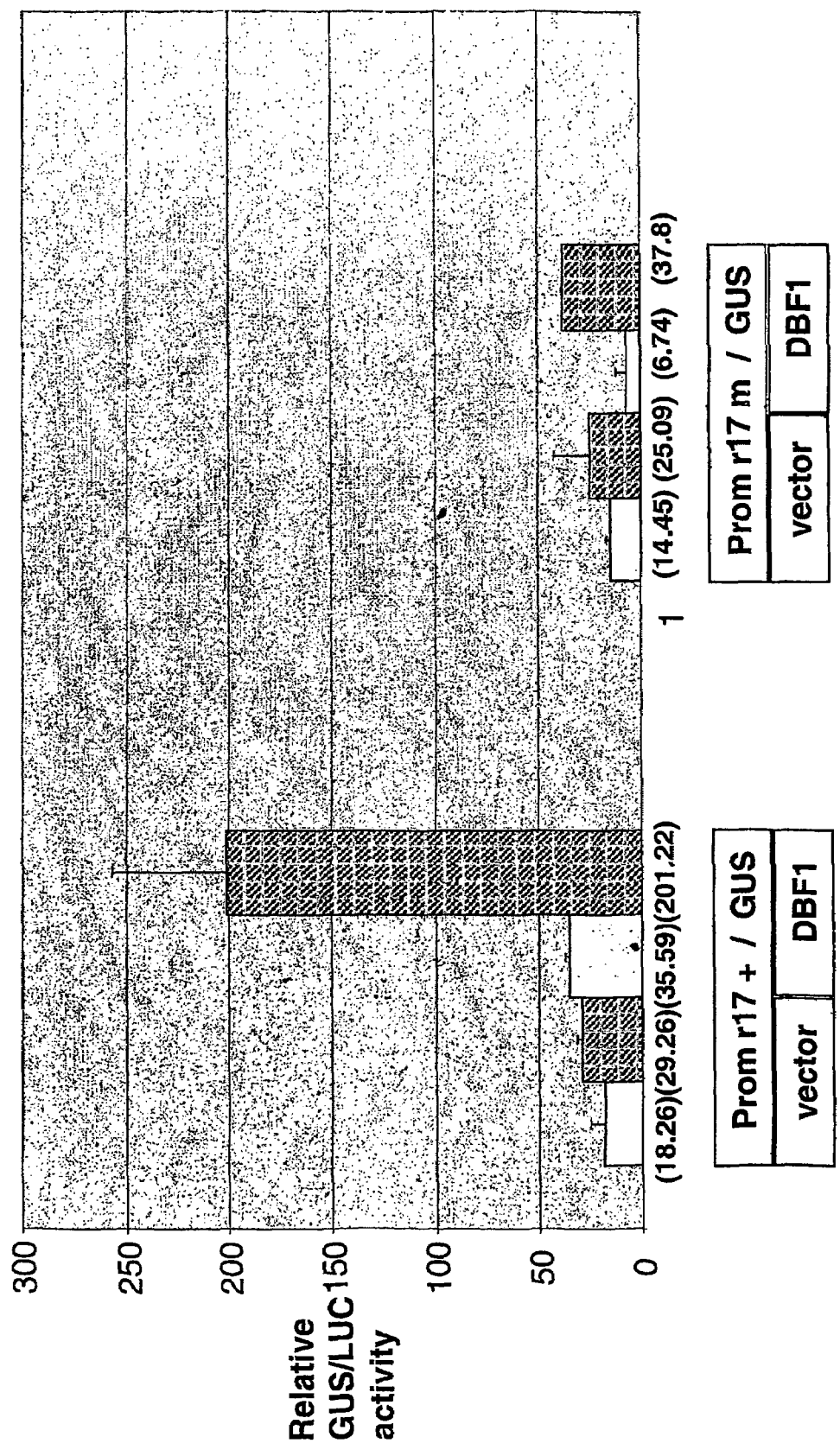
FIG. 5:
Values and histogram of relative GUS/LUC expression, showing induction of Rab17 promoter activity in maize callus cells by transient expression of DBF1. The GUS gene is under control of the, 350 bp wild-type rab 17 promoter (r17+) or of a mutant form carrying a modified DRE2 cis element (r17 m). The mutation in DRE2 is the same as in the oligonucleotide probe used for EMSA (see materials and methods). The effector plasmid consists of the DBF1 cDNA under control of a double CaMV 35S promoter (DBF1). An empty vector is used as control (vector). White bars: without 100 µM ABA. Striped bars: with 100 µM ABA.

As seen in FIG. 5, DBF1 protein was able to induce expression of the rab17 promoter, resulting in a two-fold increase of the GUS activity. Treatment with ABA had an additional effect on the GUS expression since it resulted in a nearly three fold increase of the relative GUS activity. The mutation on the DRE2 cis-element reduced significantly the ability of the rab 17 promoter to induce expression in control conditions as well as after treatment with ABA.

Example 6

DBF1 Interacts With DRE2, But Not with DRE1 and ABRE Cis-elements

DBF1 was expressed in *E. coli* using the pET overexpression system in order to study its DNA binding properties. The purified DBF1 protein was used in electrophoretic mobility shift assays in order to determine its ability to bind to different oligonucleotide probes.

The following DNA oligonucleotides were used in electrophoretic mobility shift assays: DRE2 (SEQ ID NO 4 and 5), DRE2 m (SEQ ID NOs 6 and 7), DRE1 (SEQ ID NO 8 and 9), DRE1/ABRE1 (SEQ ID NOs 10 and 11), ABRE A (SEQ ID Nos12 and 13). The full-length oligonucleotides were purified by denaturing PAGE. Complementary oligonucleotides were annealed and purified in nondenaturing polyacrylamide gel. The double-stranded oligonucleotides were labelled with $\alpha^{32}$P-dATP (3000 Ci/mmol, Amersham) by filling in with the Klenow fragment of the DNA polymerase I (Sambrook et al., 1989) and purified on a NAP5 column (Pharmacia), according to the manufacturers instructions. Unlabeled competitor DNA was filled in with nonradioactive nucleotides.

The radioactive probe was incubated with 400 ng of protein in 20 µl of 1× binding buffer (25 mM HEPES, pH 7.8, 75 mM KCl, 5 mM $MgCl_2$, 0.5 mM EDTA, 0.2 mM DTT and 10% glycerol) and 700 ng poly(dl-dC) for 20 min on ice before loading on a 1× Tris-borate-EDTA, 5% (30:0.8 acrylamide-bis) polyacrylamide gel. Electrophoresis was at at 10 V/cm at 4° C. In competition assays the protein was incubated with non-radioactive oligonucleotides in 1× binding buffer, on ice for 10 min prior to adding the radioactive probe and continuing with incubation for 20 min more.

Figure 6:
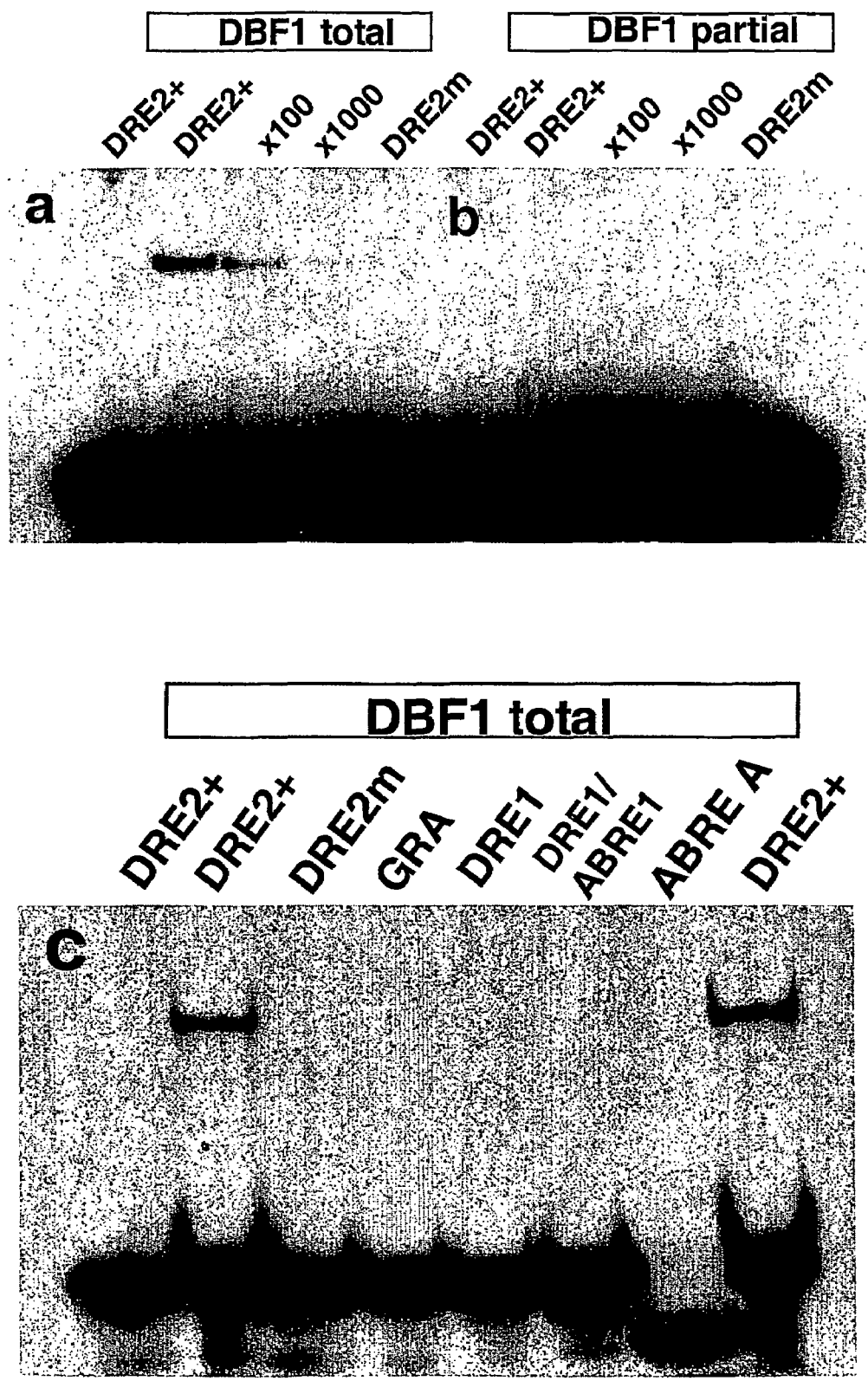
FIG. 6:
Electrophoretic Mobility Shift Assay (EMSA) of total and partial DBF1.
a) EMSA of the DBF1 total protein using oligonucleotides containing the wild type (lanes 1-4) and mutant DRE2 (lane 5) cis-element as probes. Lane 1: free probe only. Lanes 2-5: +200 ng of DBF1 total protein. Lane 3: 100× competition with the DRE2 wt cis-element. 4: 1000× competition with the DRE2 wt cis element.
b) same as a), but using the DBF1 partial protein which lacks the AP2 domain, for all reactions.
c) EMSA of the DBF1 total protein with different oligonucleotide probes.
Lane 1: free probe containing the DRE2 wt cis-element only. Lanes 2-5: +200 ng of DBF1 total protein. 2 and 7: probe containing the DRE2 wt cis-element. 3: probe containing the DRE1 mutant cis-element. 4: probe containing the GRA wt cis-element 5: probe containing the DRE1/ABRE1 wt cis-element. 6: probe containing the ABRE A cis-element from the rab28 gene promoter.

DBF1 bound successfully to the oligonucleotide containing the wild type DRE2, cis-element but not to the oligonucleotide harbouring the mutant version of DRE2 (FIG. 6). The specificity of the DBF1-DRE2 binding was confirmed by competition assays as well as with the use of different oligonucleotide probes. In the promoter of the rab17gene the DRE1 and ABRE1 cis-elements are putative targets for transcription factors. The DRE1 overlaps partially with the ABRE1 and contains a sequence motif that differs only in one nucleotide when compared with to the DRE2 sequence. As shown in, FIG. 6, DBF1 was unable to bind to any of these elements or to their combination. Furthermore, no mobility shift was detected when a partial DBF1 protein lacking the DNA binding domain was used with either wild type or mutated DRE2 oligonucleotides. These results indicate that DBF1 bind specifically to the DRE2 cis-element.

Example 7

Transgenic Plants Expressing DBF1 Under Control of a Constitutive or Regulatable Promoter Show Enhanced Tolerance to Dehydration Stress The maize DBF1 cDNA is cloned in a plant transformation vector, once under control of the constitutive GOS2 promoter and once under control of, the rab17 promoter, which is induced in leaves and seeds by ABA and dehydration stress. Empty vectors (i.e. without DBF1) are used as controls. All four constructs are introduced into rice by *Agrobacterium* mediated transformation (Hiei et al., Plant J: 6 271-282, 1994). Transgenic lines are selected in tissue culture medium supplemented with the appropriate antibiotic. Selected lines are transferred to pots in the greenhouse and the presence of the T-DNA construct in these lines is confirmed by PCR amplification on genomic DNA of a fragment of the T-DNA construct. Expression of the DBF1 transgene is analyzed in leaves and seeds under non-stressed conditions as well as after ABA and drought treatment, both at the mRNA level (Northern analysis and RT-PCR) and at the protein level (Western analysis using anti-DBF1 antibodies). Transgenic lines with different levels of DBF1 expression are selected for self-pollination and seed production. Expression of the DBF1 transgene is analyzed again in the progeny. Furthermore, the functionality of the DBF1 transgene is analyzed: expression of rab17 and other DRE2 element containing genes in plants with and without the DBF1 transgene is compared by Northern analysis, both in non-stressed and drought treated plants. Plants with functional DBF1 transgenes are subsequently compared for tolerance to drought and salt stress against plants that do not contain the DBF1 transgene. Parameters for stress tolerance are growth & seed yield during mild stress, regrowth & seed yield after release from mild stress, growth, seed yield and survival during severe stress, regrowth & seed yield after release from severe stress. Plants expressing transgenic DBF1 are more tolerant to dehydration stress than plants without a DBF1 transgene.

Example 8

Identification of the Rice Homologue of ZmDBF1

The inventors screened the TIGR database, the Genbank database and the Rice Indica genome sequences published by The Beijing Genomics Institute, an operating arm of the Chinese Academy of Sciences. A prediction of the putative ORF's corresponding to the DNA sequences in this database was available to the inventors. This screening of the 3 databases was done with the protein sequence of ZmDBF1 using the TBLASTN program. The inventors identified a rice gene which was annotated in the Genbank database as a putative AP2-related transcription factor (Genbank accession number CAC39058), but the inventors show for the first time that this protein clusters perfectly in the group of the DBF1 protein, when doing an alignment with the program ClustalW (Blosum 32 series, Gap penalty 10.00 and Gap extension 0.05, see FIG. 7A). This rice DNA sequence is herein identified as SEQ ID NO 15 and the corresponding amino acid as SEQ ID NO 16. This rice sequence does not comprise SEQ ID NO 14 (also PZ02_LUPPO does not contain SEQ ID. NO 14), but this is the closest homologue of ZmDBF1 in the rice genome of *Oryza sative Nipponbare*. Other rice genes which are retrieved in this TBlastN search cluster in a separate group that diverged from DBF1 earlier than the other homologue SEQ ID NO 15. The relationship with the DBF1 protein is further illustrated in FIG. 7. The figure shows that only one of rice sequences (corresponding to the protein CAC39058) clusters with DBF1 and to other related sequences from *Arabidopsis* (AAF87854) and Atriplex (AAF76898).

In FIG. 7B a pairwise alignment between the ZmDBF1 and the OsDBF1 protein is shown. The percentage similarity between the two sequences was calculated with the program GAP and was determined to be 38.4% and the percentage identity: 35.3% (see also Table 4). The GAP program aligns two sequences globally (BLOSUM62 amino acid substitution matrix, Gap Weight: 8, Length Weight: 2, Reference: Henikoff, S. and Henikoff, J. G. (1992). Amino acid substitution matrices from protein blocks. Proc. Natl. Acad. Sci. USA 89: 10915-10919).

REFERENCES

Alberts B., Bray D., Lewis J., Raff M., Roberts K., & Watson J. D. (1994) Molecular Biology of the Cell. Garland Publishing Inc.

An G., Watson B. D., Stachel S., Gordon M. P., & Nester E. W. (1985) New cloning vehicles for transformation of higher plants. *EMBO J.* 4, 277-284.

Armstrong C. L., Petersen W. P., Buchholz W. G., Bowen B. A., & Sulc S. L. (1990) Factors affecting PEG-mediated stable transformation of maize protoplasts. *Plant Cell Reports* 9, 335-339.

Banerjee A., Pramanik A., Bhattacharjya S. & Balaram P. (1996) Omega amino acids in peptide design: incorporation into helices. *Biopolymers* 39, 769-777.

Baron M. H. & Baltimore D. (1982) Antibodies against the chemically synthesized genome-linked protein of poliovirus react with native virus-specific proteins. *Cell* 28, 395-404.

Bartel P. L. & Fields S. (1997) The Yeast Two-Hybrid. System. Oxford University Press.

Bechtold N. & Pelletier G. (1998) In planta *Agrobacterium*-mediated transformation of adult *Arabidopsis thaliana* plants by vacuum infiltration. *Methods Mol. Biol.* 82, 259-266.

Bell M. H., Halford N. G., Ormrod J. C., & Francis D. (1993)-Tobacco plants transformed with cdc25, a mitotic inducer gene from fission yeast. *Plant Mol. Biol.* 23, 445-451.

Benkirane N., Guichard G., Briand J. P., & Muller S. (1996) Exploration of requirements for peptidomimetic immune recognition. Antigenic and immunogenic properties of reduced peptide bond pseudopeptide analogues of a histone hexapeptide. *J. Biol Chem.* 271, 33218-33224.

Berry A. & Brenner S. E. (1994) A prototype computer system for de novo protein design. *Biochem. Soc. Trans.* 22, 1033-1036.

Binarova P., Dolezel J., Draber P., Heberle-Bors E., Strnad M., & Bogre L. (1998) Treatment of Vicia faba root tip cells with specific inhibitors to cyclin-dependent kinases leads to abnormal spindle formation. *Plant J.* 16, 697-707.

Bogre L., Zwerger K., Meskiene I., Binarova P., Csizmadia V., Planck C., Wagner E., Hirt H., & Heberle-Bors E. (1997) The cdc2Ms kinase is differently regulated in the cytoplasm and in the nucleus. *Plant Physiol* 113, 841-852.

Bögre L., Calderini O., Binarova P., Mattauch M., Till S., Kiegerl S., Jonak C., Pollaschek C., Barker P., Huskisson N. S., Hirt H., & Heberle-Bors E. (1999) A MAP Kinase Is Activated Late in Plant Mitosis and Becomes Localized to the Plane of Cell Division. *Plant Cell* 11, 101-114.

Calderini O., Bogre L., Vicente O., Binarova P., Heberle-Bors E., & Wilson C. (1998) A cell cycle regulated MAP kinase with a possible role in cytokinesis in tobacco cells. *J. Cell Sci.* 111 (Pt 20), 3091-3100.

Christou P., McCabe D. E., & Swain W. F. (1988) Stable transformation of soybean callus by DNA-coated gold particles. *Plant Physiol.* 87, 671-674.

Cohen-Fix O. & Koshland D. (1997) The metaphase-to-anaphase transition: avoiding a mid-life crisis. *Curr. Opin. Cell Biol.* 9, 800-806.

Colasanti J., Tyers M., & Sundaresan V. (1991) Isolation and characterization of cDNA clones encoding a functional p34cdc2 homologue from *Zea mays*. *Proc. Natl. Acad. Sci.*U.S.A 88, 3377-3381.

Crossway A., Oakes J. V., Irvine J. M., Ward B., Knauf V. C., & Shewmaker C. K. (1986) Integration of foreign DNA following microinjection of tobacco mesophyll protoplasts. *Mol. Gen. Genet.* 202,179-185.

Dale E. C. & Ow D. W. (1990) Intra- and intermolecular site-specific recombination in plant cells mediated by bacteriophage P1 recombinase. *Gene* 91, 79-85.

De Veylder L., Segers G., Glab N., Casteels P., Van Montagu M., & Inze D. (1997) The *Arabidopsis* Cks1At protein binds the cyclin-dependent kinases Cdc2aAt and Cdc2bAt. *FEBS Lett.* 412, 446-452.

Dodds J. H. (1985) Plant genetic engineering. Cambridge University Press.

Doerner P., Jorgensen J. E., You R., Steppuhn J., & Lamb C. (1996) Control of root growth and development by cyclin expression [see comments]. *Nature* 380, 520-523.

Dorner B., Husar G. M., Ostresh J. M., & Houghten R. A. (1996) The synthesis of peptidomimetic combinatorial libraries through successive amide alkylations. *Bioorg. Med. Chem.* 4,709-715.

Elledge S. J. (1996) Cell cycle checkpoints: preventing an identity crisis. *Science* 274, 1664-1672.

Ellis J. G., Llewellyn D. J., Dennis E. S., & Peacock W. J. (1987) Maize Adh-1 promoter sequences control anaerobic-regulation: addition of upstream promoter elements from constitutive genes is necessary for expression in tobacco. *EMBO J.* 6, 11-16.

Evans T., Rosenthal E. T., Youngblom J., Distel D., & Hunt T. (1983) Cyclin: a protein specified by maternal mRNA in sea urchin eggs that is destroyed at each cleavage division. *Cell* 33, 389-396.

Fantes P. (1989) Yeast cell cycle. *Curr. Opin. Cell Biol* 1, 250-255.

Fassina G. & Melli M. (1994) Identification of interactive sites of proteins and protein receptors by computer-assisted searches for complementary peptide sequences. *Immunomethods.* 5, 114-120.

Fedoroff N. V. & Smith D. L. (1993) A versatile system for detecting transposition in *Arabidopsis*. *Plant J.* 3, 273-289.

Feiler H. S. & Jacobs T. W. (1990a) Cell division in higher plants: a cdc2 gene, its 34-kDa product, and histone H1 kinase-activity in pea. *Proc. Natl. Acad. Sci.*U.S.A 87, 5397-5401.

Feiler H. S. & Jacobs T. W. (1990b) Cell division in higher plants: a cdc2 gene, its 34-kDa product, and histone H1 kinase activity in pea. *Proc. Natl. Acad. Sci.*U.S.A 87, 5397-5401.

Fesquet D., Labbe J. C., Derancourt J., Capony J. P., Galas S., Girard F., Lorca T., Shuttleworth J., Doree M., & Cavadore J. C. (1993) The MO15 gene encodes the catalytic subunit of a protein kinase that activates cdc2 and other cyclin-dependent kinases (CDKs) through phosphorylation of Thr161 and its homologues. *EMBO J.* 12, 3111-3121.

Francis D., Dudits D. é., & Inzé D. (1998) Plant cell division. Portland, London.

Francis D. & Halford N. G. (1995) The plant cell cycle. *Physiol. Plant.* 93, 365-374.

Fromm M., Taylor L. P., & Walbot V. (1985) Expression of genes transferred into monocot and dicot plant cells by electroporation. *Proc. Natl. Acad. Sci.*U.S.A 82, 5824-5828.

Hanahan D. (1983) Studies on transformation of *Escherichia coli* with plasmids. *J. Mol. Biol* 166, 557-580.

Hansen G. & Chilton M. D. (1996) "Agrolistic" transformation of plant cells: Integration of T-strands generated in planta. *Proc. Natl. Acad. Sci.*U.S.A 93,14978-14983.

Hansen G., Shillito R. D., & Chilton M. D. (1997) T-strand integration in maize protoplasts after codelivery of a T-DNA substrate and virulence genes. *Proc. Natl. Acad. Sci.*U.S.A 94, 11726-11730.

Hanson B., Engler D., Moy Y., Newman B., Ralston E., & Gutterson N. (1999) A simple method to enrich an *Agrobacterium*-transformed population for plants containing only T-DNA sequences. *Plant J.* 19, 727-734.

Harlow E. & Lane D. (1988) Antibodies: A Laboratory Manual. Cold Spring Harbor Laboratory Press.

Haseloff J., Siemering K. R., Prasher D. C., & Hodge S. (1997) Removal of a cryptic intron and subcellular localization of green fluorescent protein are required to mark transgenic *Arabidopsis* plants brightly. *Proc. Natl. Acad. Sci.*U.S.A 94, 2122-2127.

Hayles J. & Nurse P. (1986) Cell cycle regulation in yeast *J. Cell Sci. Suppl* 4, 155-170.

Henlens R. P., Edwards E. A., Leyland N. R., Bean S., & Mullineaux P. M. (2000) pGreen: a versatile and flexible binary Ti vector for *Agrobacterium*-mediated plant transformation. *Plant Mol. Biol.* 42, 819-832.

Hemerly A. S., Ferreira P., de Almeida E. J., Van Montagu M., Engler G., & Inze D. (1993) cdc2a expression in *Arabidopsis* is linked with competence for cell division. *Plant Cell* 5, 1711-1723.

Herrera-Estrella L., De Block M., Messens E. H. J. P., Van Montagu M., & Schell J. (1983a) Chimeric genes as dominant selectable markers in plant cells. *EMBO J.* 2, 987-995.

Herrera-Estrella L., Depicker A., Van Montagu M., & Schell J. (1983b) Expression of chimaeric genes transferred into plant cells using a Ti-plasmid-derived vector. *Nature* 303, 209-213.

Hirt H., Pay A., Bogre L., Meskiene I., & Heberle-Bors E. (1993) cdc2MsB, a cognate cdc2 gene from alfalfa, complements the G1/S but not the G2/M transition of budding yeast cdc28 mutants. *Plant J.* 4, 61-69.

Hirt H., Pay A., Gyorgyey J., Bako L., Nemeth K., Bogre L., Schweyen R. J., Heberle-Bors E., & Dudits D. (1991) Complementation of a yeast cell cycle mutant by an alfalfa cDNA encoding a protein kinase homologous to p34cdc2. *Proc. Natl. Acad. Sci.*U.S.A 88, 1636-1640.

Hochstrasser M. (1998) There's the rub: a novel ubiquitin-like modification linked to cell cycle regulation. *Genes Dev.* 12, 901-907.

Hoffman D. L., Laiter S., Singh R. K., Vaisman I. I., & Tropsha A. (1995) Rapid protein structure classification using one-dimensional structure profiles on the bioSCAN parallel computer. *Comput. Appl. Biosci.* 1.1 675-679.

Huntley R., Healy S., Freeman D., Lavender P., de Jager S., Greenwood J., Makker J., Walker E., Jackman M., Xie Q., Bannister A. J., Kouzarides T., Gutierrez C., Doonan J. H. & Murray J. A. (1998) The maize retinoblastoma protein homologue ZmRb-1 is regulated during leaf development and displays conserved interactions with G1/S regulators and plant cyclin D (CycD) proteins. *Plant Mol. Biol.* 37,155-169.

John P. C., Sek F. J., & Lee M. G. (1989) A homolog of the cell cycle control protein p34cdc2 participates in the division cycle of Chlamydomonas, and a similar protein is detectable in higher plants and remote taxa. *Plant Cell* 1, 1185-1193.

John P. C. L. (1981) The Cell cycle. Cambridge University Press, Cambridge Cambridgeshire.

Joung J. K., Ramm E. I., & Pabo G. O. (2000) A bacterial two-hybrid selection system for studying protein-bNA and protein-protein interactions. *Proc. Natl. Acad. Sci.* U.S.A 97, 7382-7387.

Krek W. (1998) Proteolysis and the G1-S transition: the SCF connection. *Curr. Opin. Genet. Dev.* 8, 36-42.

Krens F. A., Molendijk L., Wullems G. J., & Schilperoort R. A. (1982) In vitro transformation of plant protoplasts with Ti-plasmid DNA. *Nature* 296, 72-74.

Kumagai A. & Dunphy W. G. (1991) The cdc25 protein controls tyrosine dephosphorylation of the cdc2 protein in a cell-free system. *Cell* 64, 903-914.

Labbe J. C., Capony J. P., Caput D., Cavadore J. C., Derancourt J., Kaghad M., Lelias J. M., Picard A., & Doree M. (1989) MPF from starfish oocytes at first meiotic metaphase is a heterodimer containing one molecule of cdc2 and one molecule of cyclin B. *EMBO J.* 8, 3053-3058.

Lake R. S. & Salzman N. P. (1972) Occurrence and properties of a chromatin-associated F1-histone phosphokinase in mitotic Chinese hamster cells. *Biochemistry* 11, 4817-4826.

Langan T. A. (1978) Methods for the assessment of site-specific histone phosphorylation. *Methods Cell Biol.* 19, 127-142.

Lee M. G. & Nurse P. (1987) Complementation used to clone a human homologue of the fission yeast cell cycle control gene cdc2. *Nature* 327, 31-35.

Lerner R. A. (1982) Tapping the immunological repertoire to produce antibodies of predetermined specificity. *Nature* 299, 593-596.

Lerner R. A., Green N., Alexander H., Liu F. T., Sutcliffe J. G., & Shinnick T. M. (1981) Chemically synthesized peptides predicted from the nucleotide sequence of the hepatitis B virus genome elicit antibodies reactive with the native envelope protein of Dane particles. *Proc. Natl. Acad. Sci.* U.S.A 78, 3403-3407.

Liddle J. E. & Cryer A. (1991) A Practical Guide to Monoclonal Antibodies. Wiley New York.

Lisztwan J., Marti A., Sutterluty H., Gstaiger M., Wirbelauer C., & Krek W. (1998) Association of human CUL-1 and ubiquitin-conjugating enzyme CDC34 with the F-box protein p45(SKP2): evidence for evolutionary conservation in the subunit composition of the CDC34-SCF pathway. *EMBO J.* 17, 368-383.

Loffler J., Langui D., Probst A., & Huber G. (1994) Accumulation of a 50 kDa N-terminal fragment of beta-APP695 in Alzheimer's disease hippocampus and neocortex. *Neurochem. Int.* 24, 281-288.

Lundgren K., Walworth N., Booher R., Dembski M., Kirschner M., & Beach D. (1991) mik1 and wee1 cooperate in the inhibitory tyrosine phosphorylation of cdc2. *Cell* 64, 1111-1122.

Magyar Z., Meszaros T., Miskolczi P., Deak M., Feher A., Brown S., Kondorosi E., Athanasiadis A., Pongor S., Bilgin M., Bako L., Koncz C., & Dudits D. (1997) Cell cycle phase specificity of putative cyclin-dependent kinase variants in synchronized alfalfa cells. *Plant Cell* 9, 223-235.

Merrifield R. B. (1963) Solid phase peptide synthesis. I. The synthesis of a tetrapeptide *J. Amer. Chem. Soc.* 85,2149-2154.

Mironov V., De Veylder L., Van Montagu M., & Inze D. (1999) Cyclin-dependent kinases and cell division in plants-The Nexus. *Plant Cell* 11, 509-522.

Monge A., Lathrop E. J., Gunn J. R., Shenkin P. S., & Friesner R. A. (1995) Computer modeling of protein folding: conformational and energetic analysis of reduced and detailed protein models. *J. Mol. Biol* 247, 995-1012.

Murakami T., Simonds W. F., & Spiegel A. M. (1992) Site-specific antibodies directed against G protein beta and gamma subunits: effects on alpha and beta gamma subunit interaction. *Biochemistry* 31, 2905-2911.

Murray A. W. & Kirschner M. W. (1989) Dominoes and clocks: the union of two views of the cell cycle. *Science* 246, 614-621.

Nasmyth K. (1993) Control of the yeast cell cycle by the Cdc28 protein kinase. *Curr. Opin. Cell Biol* 5, 166-179.

Norbury C. & Nurse P. (1992) Animal cell cycles and their control. *Annu. Rev. Biochem.* 61, 441-470.

Nurse P. (1990) Universal control mechanism regulating onset of M-phase. *Nature* 344, 503-508.

Nurse P. & Bissett Y. (1981) Gene required in G1 for commitment to cell cycle and in G2 for control of mitosis in fission yeast. *Nature* 292, 558-560.

Olszewski K. A., Kolinski A., & Skolnick J. (1996) Folding simulations and computer redesign of protein A three-helix bundle motifs. *Proteins* 25, 286-299.

Onouchi H., Nishihama R., Kudo M., Machida Y., & Machida C. (1995) Visualization of site-specific recombination catalyzed by a recombinase from *Zygosaccharomyces rouxii* in *Arabidopsis thaliana*. *Mol. Gen. Genet.* 247, 653-660.

Onouchi H., Yokoi K., Machida C., Matsuzaki H., Oshima Y., Matsuoka K., Nakamura K., & Machida Y. (1991) Operation of an efficient site-specific recombination system of *Zygosaccharomyces rouxii* in tobacco cells. *Nucleic Acids Res.* 19, 6373-6378.

Ormrod & Francis (1993b) Molecular and cell biology of the plant cell cycle proceedings of a meeting held at Lancaster University, 9-10 April 1992. Kluwer Academic, Dordrecht.

Ormrod & Francis (1993a) Molecular and cell biology of the plant cell cycle proceedings of a meeting held at Lancaster University, 9-10 April 1992. Kluwer Academic, Dordrecht.

Osborne B. I., Wirtz U., & Baker, B. (1995) A system for insertional mutagenesis and chromosomal rearrangement using the Ds transposon and Cre-lox. *Plant J.* 7, 687-701.

Ostresh J. M., Blondelle S. E., Dorner B., & Houghten R. A. (1996) Generation and use of nonsupport-bound peptide and peptidomimetic combinatorial libraries. *Methods Enzymol.* 267, 220-234.

Pabo C. O. & Suchanek E. G. (1986) Computer-aided model-building strategies for protein design. *Biochemistry* 25, 5987-5991.

Palmgren G. (1997) Transgenic plants: environmentally safe factories of the future. *Trends Genet.* 13, 348.

Paszkowski J., Shillito R. D., Saul M., Mandak V., & Hohn T. H. B. P. I. (1984) Direct gene transfer to plants. *EMBO J.* 3, 2717-2722.

Peralta E. G., Hellrmiss R., & Ream W. (1986) Overdrive, a T-DNA transmission enhancer on the *A. tumefaciens* tumour-inducing plasmid. *EMBO J.* 5, 1137-1142.

Pines J. (1995) Cyclins and cyclin-dependent kinases: a biochemical view. *Biochem. J.* 308 (Pt 3), 697-711.

Poon R. Y., Yamashita K., Adamczewski J. P., Hunt T., & Shuttleworth J. (1993) The cdc2-related protein p40MO15 is the catalytic subunit of a protein kinase that can activate p33cdk2 and p34cdc2. *EMBO J.* 12, 3123-3132.

Reed S. I., Hadwiger J. A., & Lorincz A. T. (1985) Protein kinase activity associated with the product of the yeast cell division cycle gene CDC28. *Proc. Natl. Acad. Sci.*U.S.A 82, 4055-4059.

Renaudin J. P., Doonan J. H., Freeman D., Hashimoto J., Hirt H., Inze D., Jacobs T., Kouchi H., Rouze P., Sauter M., Savoure A., Sorrell D. A., Sundaresan V., & Murray J. A. (1996) Plant cyclins: a unified nomenclature for plant A-, B- and D-type cyclins based on sequence organization. *Plant Mol. Biol.* 32, 1003-1018.

Renouf D. V. & Hounsell E. F. (1995) Molecular modelling of glycoproteins by homology with non-glycosylated protein domains, computer simulated glycosylation and molecular dynamics. *Adv. Exp. Med. Biol* 376, 37-45.

Rose R. B., Craik C. S., Douglas N. L., & Stroud R. M. (1996) Three-dimensional structures of HIV-1 and SIV protease product complexes. *Biochemistry* 35, 12933-12944.

Russell P. & Nurse P. (1986) cdc25+functions as an inducer in the mitotic control of fission yeast. *Cell* 45, 145-153.

Russell P. & Nurse P. (1987a) Negative regulation of mitosis by wee1+, a gene encoding a protein kinase homolog. *Cell* 49, 559-567.

Russell P. & Nurse P. (1987b) The mitotic inducer nim1+ functions in a regulatory network of protein kinase homologs controlling the initiation of mitosis. *Cell* 49, 569-576.

Rutenber E. E., McPhee F., Kaplan A. P., Gallion S. L., Hogan J. C., Jr., Craik C. S., & Stroud R. M. (1996). A new class of HIV-1 protease inhibitor: the crystallographic structure, inhibition and chemical synthesis of an aminimide peptide isostere. *Bioorg. Med. Chem.* 4, 1545-1558.

Sambrook J., Fritsch E. F., & Maniatis T. (1989) Molecular Cloning: A Laboratory Manual. Cold Spring Harbor Laboratory Press.

Schlappi M., Smith D., & Fedoroff N. (1993) TnpA trans-activates methylated maize Suppressor-mutator transposable elements in transgenic tobacco. *Genetics* 133, 1009-1021.

Semler B. L., Anderson C. W., Hanecak R., Dorner L. F., & Wimmer E. (1982) A membrane-associated precursor to poliovirus VPg identified by immunoprecipitation with antibodies directed against a synthetic heptapeptide. *Cell* 28, 405-412.

Shioda T., Andriole S., Yahata T., & Isselbacher K. J. (2000) A green fluorescent protein-reporter mammalian two-hybrid system with extrachromosomal maintenance of a prey expression plasmid: Application to interaction screening. *Proc. Natl. Acad. Sci.*U.S.A 97, 5220-5224.

Soni R., Carmichael J. P., Shah Z. H., & Murray J. A. (1995) A family of cyclin D homologs from plants differentially controlled by growth regulators and containing the conserved retinoblastoma protein interaction motif. *Plant Cell* 7, 85-103.

Sorrell D. A., Combettes B., Chaubet-Gigot N., Gigot C., & Murray J. A. (1999) Distinct cyclin D genes show mitotic accumulation or constant levels of transcripts in tobacco bright yellow-2 cells. *Plant Physiol* 119, 343-352.

Sugita K., Kasahara T., Matsunaga E., & Ebinuma H. (2000) Technical advance: A transformation vector for the production of marker-free transgenic plants containing a single copy transgene at high frequency [In Process Citation]. *Plant J.* 22, 461-469.

Sun Y., Dilkes B. P., Zhang C., Dante R. A., Carneiro N. P., Lowe K. S., Jung R., Gordon-Kamm W. J. &.Larkins B. A. (1999) Characterization of maize (Zea mays L.) Wee1 and its activity in developing endosperm. *Proc. Natl. Acad. Sci.*U.S.A 96, 4180-4185.

Swenson K. I., Farrell K. M., & Ruderman J. V. (1986) The clam embryo protein cyclin A induces entry into M phase and the resumption of meiosis in Xenopus oocytes. *Cell* 47, 861-870.

Tamura R. N., Cooper H. M., Collo G., & Quaranta V. (1991) Cell type-specific integrin variants with alternative alpha chain cytoplasmic domains. *Proc. Natl. Acad. Sci.*U.S.A 88, 10183-10187.

Trieu A. T., Burleigh S. H., Kardailsky I. V., Maldonado-Mendoza I. E., Versaw W. K., Blaylock L. A., Shin H., Chiou T. J., Katagi H., Dewbre G. R., Weigel D., & Harrison M. J. (2000) Technical Advance: Transformation of Medicago truncatula via infiltration of seedlings or flowering plants with *Agrobacterium*. *Plant J.* 22, 531-541.

van Haaren M. J., Sedee N. J., Schilperoort R. A., & Hooykaas P. J. (1987) Overdrive is a T-region transfer enhancer which stimulates T-strand production in *Agrobacterium tumefaciens*. *Nucleic Acids Res.* 15, 8983-8997.

Van Sluys M. A., Tempe J., & Fedoroff N. (1987) Studies on the introduction and mobility of the maize Activator element in *Arabidopsis thaliana* and *Daucus carota*. *EMBO J.* 6, 3881-3889.

Wang K., Genetello C., Van Montagu M., & Zambryski P. C. (1987) Sequence context of the T-DNA border repeat element determines its relative activity during T-DNA transfer to plant cells. *Mol. Gen. Genet.* 210, 338-346.

Wang Y., Dimitrov K., Garrity L. K., Sazer S., & Beverley S. M. (1998) Stage-specific activity of the Leishmania major CRK3 kinase and functional rescue of a *Schizosaccharomyces pombe* cdc2 mutant. *Mol. Biochem. Parasitol.* 96, 139-150.

Wilson A., Pfosser M., Jonak C., Hirt H., Heberle-Bors E., & Vicente O. (1999) Evidence for the activation of a MAP kinase upon phosphate-induced cell cycle re-entry in tobacco cells. *Physiol. Plant* 102, 532-538.

Wodak S. J. (1987) Computer-aided design in protein engineering. *Ann. N. Y. Acad. Sci.* 501, 1-13.

Woulfe J., Lafortune L., de Nadai F., Kitabgi P., & Beaudet A. (1994) Post-translational processing of the neurotensin/neuromedin N precursor in the central nervous system of the rat—II. Immunohistochemical localization of maturation products. *Neuroscience* 60, 167-181.

Xie Q., Sanz-Burgos. A. P., Hannon G. J., & Gutierrez C. (1996) Plant cells contain a novel member of the retinoblastoma family of growth regulatory proteins. *EMBO J.* 15, 4900-4908.

Yoon K., Cole-Strauss A., & Kmiec E. B. (1996) Targeted gene correction of episomal DNA in mammalian cells mediated by a chimeric RNA. DNA oligonucleotide. *Proc. Natl. Acad. Sci. U.S.A* 93, 2071-2076.

Zeng Y., Forbes K. C., Wu Z., Moreno S., Piwnica-Worms H., & Enoch T. (1998) Replication checkpoint requires phosphorylation of the phosphatase Cdc25 by Cds1 or Chk1. *Nature* 395, 507-510.

Zhang Y. L., Dawe A. L., Jiang Y., Becker J. M., & Naider F. (1996) A superactive peptidomimetic analog of a farnesylated dodecapeptide yeast pheromone. *Biochem. Biophys. Res. Commun.* 224, 327-331.

The invention claimed is:

1. An isolated polynucleotide selected from the group consisting of (a) an isolated polynucleotide of SEQ ID NO 2 and (b) an isolated polynucleotide coding for the amino acid sequence of SEQ ID NO 3.

2. The isolated polynucleotide according to claim 1, encoding a polypeptide that binds to a dehydration responsive element cis regulatory DNA sequence.

3. The isolated polynucleotide according to claim 2, for which intensity of said binding is regulated by abscisic acid.

4. The isolated polynucleotide according to claim 2, which activates transcription of nucleic acid sequences increased by said cis regulatory DNA sequence in response to abscisic acid.

5. The isolated polynucleotide according to claim 1, which is cDNA, DNA, genomic DNA or synthetic DNA, or RNA wherein T is replaced by U.

6. A vector comprising the isolated polynucleotide according to claim 1.

7. The vector of claim 6, which is an expression vector, wherein said isolated polynucleotide is operably linked to one or more control sequences allowing the expression in prokaryotic and/or eukaryotic host cells.

8. A bacterial or plant host cell comprising the isolated polynucleotide of claim 1 or a vector comprising the isolated polynucleotide.

9. A transgenic plant cell comprising the isolated polynucleotide of claim 1 or a vector comprising the isolated polynucleotide.

10. The transgenic plant cell of claim 9, wherein said isolated polynucleotide or said vector is stably integrated into the genome of the plant cell.

11. A transgenic plant or a plant tissue comprising the plant cell of claim 9.

12. A method for the production of a transgenic plant, plant cell or plant tissue, comprising introducing the isolated polynucleotide of claim 1, or a vector comprising the isolated polynucleotide into the plant, plant cell or plant tissue.

13. The method of claim 12, further comprising regenerating a plant from said plant cell or plant tissue.

14. A method for increasing growth and/or yield of a plant under stressed and/or non-stressed conditions, said method comprising introducing the isolated polynucleotide of claim 1, or a vector comprising the isolated polynucleotide, into a plant cell, plant tissue or plant, and expressing the introduced polynucleotide.

15. A transgenic plant obtained by the method of claim 12.

16. The transgenic plant cell according to claim 9, wherein said plant cell is a monocotyledonous or a dicotyledonous plant cell.

17. A plant tissue obtained from the plant cell of claim 9, wherein said tissue comprises the isolated polynucleotide.

18. A harvestable part or propagule obtained from the plant cell of claim 9, wherein the harvestable part or propagule comprises the isolated polynucleotide.

19. The harvestable part according to claim 18, which is selected from the group consisting of seeds, leaves, roots, flowers, fruits, stems, rhizomes, tubers and bulbs.

20. A progeny obtained from the plant cell plant tissue or of claim 9, wherein the progeny comprises the isolated polynucleotide.

21. A transgenic plant obtained by the method of claim 14.

22. The transgenic plant according to claim 15, wherein said plant is a monocotyledonous plant or a dicotyledonous plant.

23. The transgenic plant according to claim 21, wherein said plant is a monocotyledonous plant or a dicotyledonous plant.

24. A plant tissue isolated from the plant of claim 15, wherein said tissue comprises the isolated polynucleotide.

25. A plant tissue isolated from the plant of claim 21, wherein said tissue comprises the isolated polynucleotide.

26. A harvestable part or propagule obtained from the plant of claim 15, wherein the harvestable part or propagule comprises the isolated polynucleotide.

27. A harvestable part or propagule obtained from the plant of claim 21, wherein the harvestable part or propagule comprises the isolated polynucleotide.

28. The harvestable part according to claim 26, which is selected from the group consisting of seeds, leaves, roots, flowers, fruits, stems, rhizomes, tubers and bulbs.

29. The harvestable part according to claim 27, which is selected from the group consisting of seeds, leaves, roots, flowers, fruits, stems, rhizomes, tubers and bulbs.

30. A progeny of the plant of claim 15, wherein the progeny comprises the isolated polynucleotide.

31. A progeny of the plant of claim 21, wherein the progeny comprises the isolated polynucleotide.

\* \* \* \* \*

SEQUENCE LISTING

<160> NUMBER OF SEQ ID NOS: 28

<210> SEQ ID NO 1
<211> LENGTH: 59
<212> TYPE: DNA
<213> ORGANISM: Artificial Sequence
<220> FEATURE:
<223> OTHER INFORMATION: Synthetic DNA

<400> SEQUENCE: 1
aattcccggg ccaccgacgc acggccgcac cgacgcacgg ccgggccacc gacgcacgg      59

<210> SEQ ID NO 2
<211> LENGTH: 1043
<212> TYPE: DNA
<213> ORGANISM: Zea mays

<400> SEQUENCE: 2
gcacgagcaa tccccttcaa caaacgcacc gcactccacg gcagccagaa acacatccc      60 acggggccca gacccggcga cccacctgag cccggcgcag atgcagttca tccaggccca     120
gctccacctg cagcggaacc cggggctggg cccgcgggcg cagcccatga agcccgccgt     180
cccagtgccg ccggcgccgg cgccgcagcg gcctgtgaag ctgtaccgcg gcgtgcggca     240
gcgtcactgg ggcaagtggg tggccgagat ccggctcccc cggaaccgca cccgcctgtg     300
gctcgggacc ttcgacaccg ccgagcaggc agcgctggcc tacgaccagg cggcgtaccg     360
cctccgcggg gacgcggcgc ggctcaactt ccccgacaac gcggagtcca gggcgccgct     420
cgaccccgcc gtggacgcca agctgcaggc catctgcgcc accatcgccg ccgcgtcgtc     480
gtcatccaag aattccaagg ccaagagcaa ggcgatgcca atcaacgcgt ccgttctgga     540
agcggcagcg cgtctccga gcaacagctc ctccgacgaa ggttccggct ccgggttcgg     600
gtcggacgac gagatgtcct cgtcttcccc gacgccggtg gtggcgccgc cggtggcgga     660
catgggacag ttggatttca gcgaggttcc gtgggacgag gacgagagct tcgtgctccg     720
caagtacccg tcctacgaga tcgactggga cgcgctgctc tccaactagt cgcccttcgc     780
cgacagatgt gctgttgtag ttcagtagtg gcagtatctc tggccgccgc agatgaggtt     840
ttaggcaatc tgcaggccgc cggcccatgt gtattaagta ggttttgctc agttgttggc     900
cccggacttc gccggcgttt ttgtgaccgg cgtccccgag tgcactgcat tggtgtactg     960
gtctgtctgt aaaaaaaaat ggatctgtgt acttctatag tgtgtattca accattgttc    1020
ttaaaaaaaa aaaaaaaaa aaa                                            1043

<210> SEQ ID NO 3
<211> LENGTH: 222
<212> TYPE: PRT
<213> ORGANISM: Zea mays

<400> SEQUENCE: 3

Met Gln Phe Ile Gln Ala Gln Leu His Leu Gln Arg Asn Pro Gly Leu
1               5                   10                  15

Gly Pro Arg Ala Gln Pro Met Lys Pro Ala Val Pro Val Pro Pro Ala
            20                  25                  30

Pro Ala Pro Gln Arg Pro Val Lys Leu Tyr Arg Gly Val Arg Gln Arg
        35                  40                  45

His Trp Gly Lys Trp Val Ala Glu Ile Arg Leu Pro Arg Asn Arg Thr
    50                  55                  60

```
Arg Leu Trp Leu Gly Thr Phe Asp Thr Ala Glu Gln Ala Ala Leu Ala
 65                  70                  75                  80

Tyr Asp Gln Ala Ala Tyr Arg Leu Arg Gly Asp Ala Ala Arg Leu Asn
                 85                  90                  95

Phe Pro Asp Asn Ala Glu Ser Arg Ala Pro Leu Asp Pro Ala Val Asp
            100                 105                 110

Ala Lys Leu Gln Ala Ile Cys Ala Thr Ile Ala Ala Ser Ser Ser
        115                 120                 125

Ser Lys Asn Ser Lys Ala Lys Ser Lys Ala Met Pro Ile Asn Ala Ser
    130                 135                 140

Val Leu Glu Ala Ala Ala Ala Ser Pro Ser Asn Ser Ser Ser Asp Glu
145                 150                 155                 160

Gly Ser Gly Ser Gly Phe Gly Ser Asp Asp Glu Met Ser Ser Ser Ser
                165                 170                 175

Pro Thr Pro Val Val Ala Pro Pro Val Ala Asp Met Gly Gln Leu Asp
            180                 185                 190

Phe Ser Glu Val Pro Trp Asp Glu Asp Glu Ser Phe Val Leu Arg Lys
        195                 200                 205

Tyr Pro Ser Tyr Glu Ile Asp Trp Asp Ala Leu Leu Ser Asn
210                 215                 220
```

```
<210> SEQ ID NO 4
<211> LENGTH: 34
<212> TYPE: DNA
<213> ORGANISM: Artificial Sequence
<220> FEATURE:
<223> OTHER INFORMATION: Synthetic DNA

<400> SEQUENCE: 4
ggggtcgacc gggccaccga cgcaccggct cgag                       34

<210> SEQ ID NO 5
<211> LENGTH: 33
<212> TYPE: DNA
<213> ORGANISM: Artificial Sequence
<220> FEATURE:
<223> OTHER INFORMATION: Synthetic DNA

<400> SEQUENCE: 5
ggggctcgag ccgtgcgtcg gtggcccggt cga                        33

<210> SEQ ID NO 6
<211> LENGTH: 34
<212> TYPE: DNA
<213> ORGANISM: Artificial Sequence
<220> FEATURE:
<223> OTHER INFORMATION: Synthetic DNA

<400> SEQUENCE: 6
ggggtcgacc gggccagaat tccaccggct cgag                       34

<210> SEQ ID NO 7
<211> LENGTH: 33
<212> TYPE: DNA
<213> ORGANISM: Artificial Sequence
<220> FEATURE:
<223> OTHER INFORMATION: Synthetic DNA

<400> SEQUENCE: 7
ggggctcgag ccgtggaatt ctggcccggt cga                        33
```

<210> SEQ ID NO 8
<211> LENGTH: 33
<212> TYPE: DNA
<213> ORGANISM: Artificial Sequence
<220> FEATURE:
<223> OTHER INFORMATION: Synthetic DNA

<400> SEQUENCE: 8
ggggtcgaga agaaccgaga cgaagcggtc gag                         33

<210> SEQ ID NO 9
<211> LENGTH: 33
<212> TYPE: DNA
<213> ORGANISM: Artificial Sequence
<220> FEATURE:
<223> OTHER INFORMATION: Synthetic DNA

<400> SEQUENCE: 9
ggggctcgac cgcttcgtct cggttcttct cga                         33

<210> SEQ ID NO 10
<211> LENGTH: 31
<212> TYPE: DNA
<213> ORGANISM: Artificial Sequence
<220> FEATURE:
<223> OTHER INFORMATION: Synthetic DNA

<400> SEQUENCE: 10
ggggtcgaga agaaccgacg tggcggtcga g                           31

<210> SEQ ID NO 11
<211> LENGTH: 33
<212> TYPE: DNA
<213> ORGANISM: Artificial Sequence
<220> FEATURE:
<223> OTHER INFORMATION: Synthetic DNA

<400> SEQUENCE: 11
ggggctcgac cgccacgtct cggttcttct cga                         33

<210> SEQ ID NO 12
<211> LENGTH: 32
<212> TYPE: DNA
<213> ORGANISM: Artificial Sequence
<220> FEATURE:
<223> OTHER INFORMATION: Synthetic DNA

<400> SEQUENCE: 12
tggaagcttc gcgccacgtg ggcatgagat ct                          32

<210> SEQ ID NO 13
<211> LENGTH: 32
<212> TYPE: DNA
<213> ORGANISM: Artificial Sequence
<220> FEATURE:
<223> OTHER INFORMATION: Synthetic DNA

<400> SEQUENCE: 13
tggagatctc atgcccacgt ggcgcgaagc tt                          32

<210> SEQ ID NO 14
<211> LENGTH: 14
<212> TYPE: PRT
<213> ORGANISM: Artificial Sequence
<220> FEATURE:
<223> OTHER INFORMATION: Synthetic Peptide

```
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Asp or Asn
<220> FEATURE:
<221> NAME/KEY: MISC_FEATURE
<222> LOCATION: (11)..(11)
<223> OTHER INFORMATION: Xaa = Gln or Glu
<220> FEATURE:
<221> NAME/KEY: MISC_FEATURE
<222> LOCATION: (12)..(12)
<223> OTHER INFORMATION: Xaa = any amino acid

<400> SEQUENCE: 14

Pro Leu Xaa Xaa Xaa Val Xaa Ala Lys Leu Xaa Xaa Ile Cys
1               5                   10

<210> SEQ ID NO 15
<211> LENGTH: 912
<212> TYPE: DNA
<213> ORGANISM: Oryza sativa

<400> SEQUENCE: 15
atgctgctta atccggcgtc gagagaggtg gccgcgctgg acagcatccg gcaccacctc      60
ctggaggagg aggaggagac gccggcgacg gcgccggcgc cgacgcggcg gccggtgtac     120
tgccggagct caagcttcgg cagcctcgtg gccgaccagt ggagcgagtc gctgccgttc     180
cggcccaacg acgccgagga catggtcgtg tacgcgcccc tccgcgacgc cttctcctcc     240
ggctggctcc ccgacggctc attcgccgcc gtcaagccgg agtcgcagga ctcctacgac     300
gggtcctcca tcggcagctt cctcgcgtcg tcgtcgtccg aggcggggac gcccggggag     360
gtgacgtcga cggaggcgac ggtgacgccg gggatcaggg agggcgaggg cgaggccgtg     420
gcggtggcgt cgaggggaa gcactaccgc ggggtgaggc agcggccgtg gggcaagttc     480
gcggcggaga tcagggaccc ggccaagaac ggcgcgcgcg tgtggctcgg cacgttcgac     540
tccgccgagg aggccgccgt ggcgtacgac gcgccgccct accgcatgcg cggctcccgc     600
gcgctcctca acttcccgct ccgcatcggc tccgagatcg ccgccgcggc cgccgccgcc     660
gccgcgggca caagcggcc atatcccgac ccggcgagct ccggctcttc ttccccttca     720
tcctcttcct cctcgtcgtc gtcttcctcc tccgggtcac cgaagcggag gaagagaggc     780
gaggccgcgc ccgcgtccat ggccatggca ctggttccac caccgccacc accggcgcag     840
gcaccggtgc agctcgcccct cccggcccag ccatggttcg ccgccggtcc gatccagcag     900
ctggtgagct aa                                                        912

<210> SEQ ID NO 16
<211> LENGTH: 303
<212> TYPE: PRT
<213> ORGANISM: Oryza sativa

<400> SEQUENCE: 16

Met Leu Leu Asn Pro Ala Ser Arg Glu Val Ala Ala Leu Asp Ser Ile
```

```
                1               5                    10                   15
Arg His His Leu Leu Glu Glu Glu Glu Thr Pro Ala Thr Ala Pro
                20                   25                   30

Ala Pro Thr Arg Arg Pro Val Tyr Cys Arg Ser Ser Phe Gly Ser
                35                   40                   45

Leu Val Ala Asp Gln Trp Ser Glu Ser Leu Pro Phe Arg Pro Asn Asp
 50                      55                   60

Ala Glu Asp Met Val Val Tyr Gly Ala Leu Arg Asp Ala Phe Ser Ser
 65                      70                   75                   80

Gly Trp Leu Pro Asp Gly Ser Phe Ala Ala Val Lys Pro Glu Ser Gln
                85                   90                   95

Asp Ser Tyr Asp Gly Ser Ser Ile Gly Ser Phe Leu Ala Ser Ser Ser
                100                  105                  110

Ser Glu Ala Gly Thr Pro Gly Glu Val Thr Ser Thr Glu Ala Thr Val
                115                  120                  125

Thr Pro Gly Ile Arg Glu Gly Gly Glu Ala Val Ala Val Ala Ser
                130                  135                  140

Arg Gly Lys His Tyr Arg Gly Val Arg Gln Arg Pro Trp Gly Lys Phe
145                      150                  155                  160

Ala Ala Glu Ile Arg Asp Pro Ala Lys Asn Gly Ala Arg Val Trp Leu
                165                  170                  175

Gly Thr Phe Asp Ser Ala Glu Ala Ala Val Ala Tyr Asp Arg Ala
                180                  185                  190

Ala Tyr Arg Met Arg Gly Ser Arg Ala Leu Leu Asn Phe Pro Leu Arg
                195                  200                  205

Ile Gly Ser Glu Ile Ala Ala Ala Ala Ala Ala Ala Gly Asn
                210                  215                  220

Lys Arg Pro Tyr Pro Asp Pro Ala Ser Ser Gly Ser Ser Ser Pro Ser
225                      230                  235                  240

Ser Ser Ser Ser Ser Ser Ser Ser Ser Gly Ser Pro Lys Arg
                245                  250                  255

Arg Lys Arg Gly Glu Ala Ala Pro Ala Ser Met Ala Met Ala Leu Val
                260                  265                  270

Pro Pro Pro Pro Pro Ala Gln Ala Pro Val Gln Leu Ala Leu Pro
                275                  280                  285

Ala Gln Pro Trp Phe Ala Ala Gly Pro Ile Gln Gln Leu Val Ser
                290                  295                  300

<210> SEQ ID NO 17
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 17

Glu Glu Thr Ala Arg Phe Gln Pro Gly Tyr Arg Ser
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 18
```

```
Glu Gln Lys Leu Ile Ser Glu Glu Asp Leu
1               5                   10
```

<210> SEQ ID NO 19
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 19

```
Asp Tyr Lys Asp Asp Asp Lys
1               5
```

<210> SEQ ID NO 20
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 20

```
Tyr Pro Tyr Asp Val Pro Asp Tyr Ala
1               5
```

<210> SEQ ID NO 21
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 21

```
Glu Asp Gln Val Asp Pro Arg Leu Ile Asp Gly Lys
1               5                   10
```

<210> SEQ ID NO 22
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 22

```
Tyr Thr Asp Ile Glu Met Asn Arg Leu Gly Lys
1               5                   10
```

<210> SEQ ID NO 23
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 23

```
Arg Ala Pro Leu Asp Pro Ala Val Asp Ala Lys Leu Gln Ala Ile Cys
1               5                   10                  15
```

<210> SEQ ID NO 24
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 24

```
Tyr Lys Pro Leu His Ser Ser Val Asn Ala Lys Leu Glu Ala Ile Cys
```

-continued

```
<210> SEQ ID NO 25
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 25

Tyr Gln Pro Leu Gln Ser Ser Val Asp Ala Lys Leu Glu Ala Ile Cys
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 26

Phe Asn Pro Leu His Ser Ser Val Asp Ala Lys Leu Gln Glu Ile Cys
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 27

Gln Ser Ser Ser Ser Lys Leu Leu Ser Ala Thr Leu Ile Ala Lys Leu
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 28

Arg Leu Arg Ile Pro Glu Ser Thr Cys Ala Lys Asp Ile Gln Lys Ala
1               5                   10                  15
```